(12) United States Patent
Chiusaroli et al.

(10) Patent No.: US 9,631,029 B2
(45) Date of Patent: Apr. 25, 2017

(54) ANTI-ADAMTS-5 ANTIBODY, DERIVATIVES AND USES THEREOF

(71) Applicant: ROTTAPHARM BIOTECH S.R.L., Monza (MB) (IT)

(72) Inventors: Riccardo Chiusaroli, Rogeno (IT); Michela Visintin, Trieste (IT); Gianfranco Caselli, Milan (IT); Lucio Claudio Rovati, Monza (IT)

(73) Assignee: ROTTAPHARM BIOTECH S.R.L., Monza (MB) (IT)

( * ) Notice: Subject to any disclaimer, the term of this patent is extended or adjusted under 35 U.S.C. 154(b) by 145 days.

(21) Appl. No.: 14/390,466

(22) PCT Filed: Apr. 12, 2013

(86) PCT No.: PCT/EP2013/057649
§ 371 (c)(1),
(2) Date: Oct. 3, 2014

(87) PCT Pub. No.: WO2013/153189
PCT Pub. Date: Oct. 17, 2013

(65) Prior Publication Data
US 2015/0056210 A1    Feb. 26, 2015

(30) Foreign Application Priority Data
Apr. 13, 2012 (EP) .................................. 12164107

(51) Int. Cl.
*A61K 39/395*  (2006.01)
*C07K 16/00*   (2006.01)
*C07K 16/40*   (2006.01)
*A61K 39/00*   (2006.01)

(52) U.S. Cl.
CPC ........ *C07K 16/40* (2013.01); *A61K 2039/505* (2013.01); *C07K 2317/21* (2013.01); *C07K 2317/24* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,766,910 A * | 6/1998 | Fukuda | C12N 9/1051 435/193 |
| 5,859,205 A * | 1/1999 | Adair | C07K 16/18 530/387.1 |
| 6,391,610 B1 * | 5/2002 | Apte | C12N 9/6489 435/219 |
| 2002/0110894 A1 * | 8/2002 | Apte | C12N 9/6489 435/226 |
| 2006/0004066 A1 | 1/2006 | Morris | |

FOREIGN PATENT DOCUMENTS

WO    2011/002968 A2    1/2011

OTHER PUBLICATIONS

Paul, Fundamental Immunology, 3rd Edition, 1993, pp. 292-295.*
Casset et al. A peptide mimetic of an anti-CD4 monoclonal antibody by rational design. Biochemical and Biophysical Research Communications, 307:198-205, 2003.*
MacCallum et al. Antibody-antigen interactions: contact analysis and binding site topography. J. Mol. Biol., 262, 732-745, 1996.*
Eduardo Padlan, Anatomy of the antibody molecule. Mol Immunol. Feb. 1994;31(3):169-217.*
Rudikoff et al Single amino acid substitution altering antigen-binding specificity. Proc Natl Acad Sci U S A. Mar. 1982;79(6):1979-83.*
Brown et al. Tolerance of single, but not multiple, amino acid replacements in antibody VH CDR 2: a means of minimizing B cell wastage from somatic hypermutation? J. Immuno. May 1996, 3285-91.*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Rees et al., Sequestration of Pro-And Truncated Isoforms of ADAMTS-4 and ADAMTS-5 in the Extracellular Matrix Formed by Chondrocytes in Agarose Culture: Effects of IL-1 Exposure. 50th Annual Meeting of the Orthopaedic Research Society. Poster No. 0613. Mar. 7-10, 2004.*
Santamaria, Salvatore. Screening, Isolation and Characterisation of Antibodies That Block Aggrecanase Activity of ADAMTS-5. A thesis submitted for the degree of Doctor of Philosophy to Imperial College London. Sep. 2013, pp. 1-236.*
Presentation of Bennett Celsa (Quality Assurance Specialist, TC 1600) entitled "Written Description: Antibodies" presented to the BCP Customer Partnership, Jun. 2, 2009, 49 slides.*
Troeberg, L., et al: "The C-terminal domains of ADAMTS-4 and ADAMTS-5 promote association with N-TIMP-3", Matrix Biology, Elsevier, NL, vol. 28. No. 8, Oct. 1, 2009 (Oct. 1, 2009), pp. 463-469, [retrieved on Jul. 28, 2009].
Fosang, A. J ., et al: "ADAMTS-5: The Story So Far", European Cells and Materials, vol. 15, Feb. 5, 2008 (Feb. 5, 2008), pp. 11-26.
Malfait, A-M., et al: Inhibition of ADAM-TS4 and ADAM-TS5 prevents aggrecan degradation in osteoarthritic cartilage, Journal of Biological Chemistry, The American Society of Biological Chemists, Inc, US, vol. 277, No. 25, Jun. 21, 2002 (Jun. 21, 2002), pp. 22201-22208.
Kintakas, Christopher, et al: "Emerging roles for ADAMTS5 during development and disease", Matrix Biology, Elsevier, NL, vol. 30, No. 5, May 25, 2011 (May 25, 2011), pp. 311-317, [retrieved on Jun. 12, 2011].

* cited by examiner

*Primary Examiner* — Maher Haddad
(74) *Attorney, Agent, or Firm* — Lucas & Mercanti, LLP

(57) ABSTRACT

The present invention relates to an antibody, recombinant or synthetic antigen-binding fragments thereof able to recognize and bind an epitope comprised in the spacer domain of ADAMTS-5, nucleic acid and expression vector encoding the same, method of production and uses thereof.

9 Claims, 12 Drawing Sheets

ANTI-ADAMTS-5 ANTIBODY, DERIVATIVES AND USES THEREOF

CROSS-REFERENCE TO RELATED APPLICATIONS

This application is a 371 of PCT/EP2013/057649, filed Apr. 12, 2013, which claims the benefits of European Patent Application No. 12164107.0, filed Apr. 13, 2012, the contents of each of which are incorporated herein by reference.

FIELD OF THE INVENTION

This invention relates to anti-ADAMTS-5 antibodies useful in the treatment of a condition associated with cartilage degradation.

In particular, such degradation is observed in osteoarthritis and in other forms of arthritides.

BACKGROUND ART

Osteoarthritis (OA) is a group of overlapping distinct diseases, which may have different etiologies but similar biologic, morphologic, and clinical outcomes. The disease process not only affects the articular cartilage, but involves the entire joint, including the subchondral bone, ligaments, capsule, synovial membrane, and periarticular muscles. Ultimately, the articular cartilage degenerates with fibrillation, fissures, ulceration, and full thickness loss of the joint surface. This condition is characterised by focal areas of loss of articular cartilage within synovial joints, associated with hypertrophy of bone (osteophytes and subchondral bone sclerosis) and thickening of the capsule. It may be interpreted as the reaction of synovial joints to injury. This phenomenon can occur in any joint, but is most common in selected joints of the hand, spine, knee, foot and hip. This pathological change, when severe, results in radiological changes (loss of joint space and osteophytes), which have been used in epidemiological studies to estimate the prevalence of OA at different joint sites. The molecular and cellular mechanisms at the basis of the onset of OA are, at present, unknown; it is hypothesised that abnormal load as well as trauma may have a role, but it seems certain that genetics and heritable factors are also involved. Inflammation, when present, is only secondary to a primary event.

OA is the most common form of arthritis. The World Health Organization (WHO) estimates that, worldwide, 9.6% of men and 18% of women aged over 60 years have symptomatic OA, classifying OA as the 4th cause of disability in women and the 8th cause in men. It is considered that the risk of disability is the same for knee OA as for cardiac disease.

Rheumatoid arthritis (RA), another common form of arthritis, is a chronic inflammatory disease characterized by articular synovitis leading to cartilage degradation, bone erosion and pain, leading to severe disability and premature mortality.

Though OA and RA can be triggered by different causes and progress according to different pathways, they share the underlying process which consists of an imbalance in cartilage matrix synthesis and breakdown, leading to the destruction of the articular cartilage which in turn results in restricted joint movement, joint instability, pain and chronic disability. Moreover, in spite of the impressive number of patients affected by OA and RA, relatively little is known regarding their aetiology, pathogenesis, and progression. Even more impressively, very few, disease-modifying agents antirheumatic drugs (DMARD) exist for their treatment, and they are mainly limited to RA.

For OA, in the absence of a cure, treatment can only be palliative, being limited to the use of COX-2 selective inhibitors, such as celecoxib, and traditional non-steroidal anti-inflammatory drugs (NSAIDs), such as naproxen and diclofenac, or even older drugs for pain control, such as acetaminophen. An additional class of drugs, which includes compounds such as chondroitin and glucosamine sulfate, also exists as a treatment option for OA, but many physicians remain unconvinced about their efficacy.

Concerning RA, over the last decade, the optimal use of DMARDs, in particular methotrexate and the availability of new biologic agents, typically supported by NSAIDs and/or corticosteroids to provide pain relief, as well as to control inflammation to some degree have dramatically enhanced the success of its management. However, traditional DMARDs have a slow onset of action and toxicity that mandates frequent monitoring. Moreover, NSAIDs use has been overshadowed by gastrointestinal side-effects, when considering classical NSAIDs drugs, and by cardiovascular and renal side-effects when considering selective COX-2 inhibitors.

Therefore, the research for new therapeutic agents preventing cartilage degradation is of great interest, since OA and RA affect millions of people all over the world with an expected incidence rising with the increase of the average population age.

The degradation of cartilage occurring in OA and RA is the result of enzymatic cleavage of its structural components. Cartilage is mainly constituted by chondrocytes and an extracellular matrix (ECM) that consists of proteoglycans (mainly aggrecan), collagens and water. Within the matrix, the interaction between aggrecan, hyaluronic acid (HA) and Type II collagen provides the cartilage with unique compressibility and elasticity, biomechanical properties for weight bearing and joint motion functions. Aggrecan consists of three globular regions: G1 and G2 near the N-terminus of the protein and G3 at the C-terminus. The G1 and G2 regions are separated by a short interglobular domain (IGD) while the G2 and G3 regions are separated by a long glycosaminoglycan (GAG) attachment region. The G1 domain constitutes, through an ancillary protein, the binding region of aggrecan to HA. The GAG attachment region of aggrecan provides the high anionic charge density needed to bind water and conferring to cartilage its unique osmotic properties necessary to guarantee its functionality. Therefore, understanding the biochemical mechanisms leading to aggrecan cleavage might help in the development of therapeutics suitable to block or control the OA disease. Loss of cartilage integrity in arthritis is associated with impaired aggrecan integrity due to proteolytic cleavage of the protein. Aggrecanases (mainly aggrecanase-2, also named ADAMTS-5 and aggrecanase-1, also named ADAMTS-4), were recently identified as being among the key enzymes for cartilage degradation. In particular, the publications Glasson et al., 2005. Nature. 434:644-648) and Stanton et al., 2005. Nature. 434:648-652), demonstrated that ADAMTS-5 plays a fundamental role in the pathological joint changes associated with two models of OA and of RA in the mouse. Both ADAMTS-4 and -5 are glutamyl endopeptidases and cleave aggrecan at five specific sites: Glu373-Ala374 (interglobular domain-IGD), Glu1545-Gly1546, Glu1714-Gly1715, Glu1819-Ala1820, and Glu1919-Leu1920 bonds (human sequence), resulting in cartilage destruction.

Human ADAMTS-4 (FIG. 1, SEQ. ID NO: 1) and ADAMTS-5 (FIG. 1, SEQ. ID NO: 2) are multidomain metalloproteinases secreted from the cell into the extracellular space. Both enzymes have a similar domain arrangement consisting of a signal sequence (SS), a prodomain (Pro), a catalytic metalloproteinase domain (Cat), a disintegrin (Dis) domain, a thrombospondin type I (TS) domain, a cysteine-rich (CysR) domain, and a spacer (Sp) domain. In addition, ADAMTS-5 contains an extra TS domain after the spacer domain. All the above mentioned domain regions outside the catalytic domain, play significant roles in recognition and processing of natural protein substrates, are termed "exosites".

It was demonstrated, for instance, that the Sp and CysR domains of aggrecanases contain GAG-binding motifs that modulate the affinity of the proteinases for their substrates (Kashiwagi et al., 2004. J Biol Chem. 279:10109-10119); (Gendron et al., 2007. J Biol Chem. 282:18294-18306); (Flannery, Curr. 11:614-619); (Zeng et al., 2006. Biochim Biophys Acta. 1760:517-524).

Thus, interest has been growing in the development of inhibitors for ADAMTS-4 and -5 for the treatment of OA and/or RA. Numerous metalloproteinase inhibitors have been developed, and several were clinically tested in patients with cancer (Zucker et al., 2000. Oncogene. 19:6642-6650) and rheumatoid arthritis (Milner and Cawston, 2005. Curr Drug Targets Inflamm Allergy. 4:363-375), but they failed to show efficacy and exhibited side effects such as musculoskeletal pain and mild thrombocytopenia (Zucker et al., 2000. Oncogene. 19:6642-6650). These failures are thought to be due to the lack of selectivity of the inhibitors and inhibition of biologically important off-target metalloproteinases and other effects. Selectivity is thus a prerequisite for nontoxic therapeutic inhibitors. One way to increase selectivity against specific metalloproteinases is to generate allosteric or exosite binding. Inhibitors that bind to an enzyme exosite could block interaction with natural ECM substrates and could be an attractive alternative to active site-directed inhibitors because they can be highly specific and effectively block hydrolysis only of the target substrate, thus minimizing in vivo side effects (Troeberg et al., 2008. Faseb J. 22:3515-3524).

The application WO 2011/002968 discloses an antibody capable of binding to both the catalytic domain and desintegrin domain of human ADAMTS-5. The documents WO 01/11074 and WO 00/53774 disclose an ADAMTS-5 protein and generally refer to antibody against such protein.

SUMMARY OF THE INVENTION

In the present invention, the authors isolated antibodies recognizing and binding to an epitope comprised in the spacer domain of ADAMTS-5 (named antibodies anti-Sp_ADAMTS-5). The antibodies are useful for therapeutic applications in humans. Typically, the antibodies are fully human or chimeric or humanized to minimize the risk for immune responses against the antibodies when administered to a patient. As described herein, other antigen-binding molecules such as, e.g., antigen-binding antibody fragments, antibody derivatives, and multi-specific molecules, can be designed or derived from such antibodies. The antibodies of the present invention display inhibitory action against cartilage matrix degeneration, they control cartilage matrix degrading enzyme production and they improve cartilage matrix synthesis, thus treat and/or prevent cartilage degradation. Therefore the antibody may be used in the treatment and/or prevention of a condition associated with cartilage degradation. Such condition includes osteoarthritis (OA), rheumatoid arthritis (RA), gout, psoriatic arthritis, systemic lupus erythematosus, septic arthritis, polymyalgia rheumatica, ankylosing spondylitis, pseudogout, polymyositis, fibromyalgia or lyme disease.

In particular, the antibodies of the present invention, may be used for treating and/or preventing the disease classified into the early stage to the advanced stage of OA and RA. Each stage from the initial stage to the advanced stage of OA is classified according to the OARSI and Mankin classification.

In both pathologies, the diseases classified into any of the above-mentioned grades or scores are accompanied with cartilage degeneration as condition of disease. The antibodies of the present invention can be used effectively to treat or prevent the diseases classified into the initial stage to the advanced stage of OA and RA.

Antibody-binding fragments of such antibodies, as well as molecules comprising such antigen-binding fragments, including engineered antibody fragments, antibody derivatives, bispecific antibodies and other multispecific molecules, are also object of the invention. Pharmaceutical compositions and kits or other articles that comprise the antibodies of the invention are also part of the invention.

It is therefore an object of the invention an antibody, recombinant or synthetic antigen-binding fragments thereof able to recognise and bind an epitope comprised in the aa. 732 to aa. 874 region of SEQ ID No. 2 of ADAMTS-5. Preferably the epitope is comprised in aa. 732 to aa 745 of SEQ ID No. 2, preferably in aa 746 to aa 763 of SEQ ID No. 2, preferably in aa 764 to aa 779 of SEQ ID No. 2, preferably in aa 780 to aa 795 of SEQ ID No. 2, preferably in aa 796 to aa 811 of SEQ ID No. 2, preferably in aa 812 to aa 827 of SEQ ID No. 2, preferably in aa 828 to aa 843 of SEQ ID No. 2, preferably in aa 844 to aa 859 of SEQ ID No. 2, preferably in aa 860 to aa 874 of SEQ ID No. 2. Still preferably, the epitope is comprised in the aa. 757 to aa 771 region of SEQ ID No. 2.

Preferably, the antibody, recombinant or synthetic antigen-binding fragments thereof as described above comprises at least one heavy chain complementary determining region (CDRH3) amino acid sequence having at least 80% identity to an amino acid sequence selected from the group consisting of: SEQ. ID NO: 62, 65, 68, 71, 74, 77, 80, 83, 86, 89 and 92.

Preferably, the antibody, recombinant or synthetic antigen-binding fragments thereof further as described above comprises a heavy chain complementary determining region (CDRH2) amino acid sequence having at least 80% identity to an amino acid sequence selected from the group consisting of: SEQ ID No. 61, 64, 67, 70, 73, 76, 79, 82, 85, 88 and 91.

Preferably, the antibody, recombinant or synthetic antigen-binding fragments thereof of the invention further comprises a heavy chain complementary determining region (CDRH1) amino acid sequence having at least 80% identity to an amino acid sequence selected from the group consisting of: SEQ ID No. 60, 63, 66, 69, 72, 75, 78, 81, 84, 87 and 90.

In a preferred embodiment, the antibody, recombinant or synthetic antigen-binding fragments thereof as described above further comprises at least one light chain complementary determining region (CDRL3) amino acid sequence having at least 80% identity to an amino acid sequence selected from the group consisting of: SEQ. ID NO: 29, 32, 35, 38, 41, 44, 47, 50, 53, 56 and 59.

In a preferred embodiment, the antibody, recombinant or synthetic antigen-binding fragments thereof of the invention further comprises one light chain complementary determining region (CDRL2) amino acid sequence having at least 80% identity to an amino acid sequence selected from the group consisting of: 28, 31, 34, 37, 40, 43, 46, 49, 52, 55 and 58.

In a preferred embodiment, the antibody, recombinant or synthetic antigen-binding fragments thereof as described above further comprises one light chain complementary determining region (CDRL1) amino acid sequence having at least 80% identity to an amino acid sequence selected from the group consisting of: 27, 30, 33, 36, 39, 42, 45, 48, 51, 54 and 57.

Preferably, the antibody, recombinant or synthetic antigen-binding fragments thereof of the invention comprises a heavy chain complementary determining regions (CDRH1) amino acid sequence having at least 80% identity to an amino acid sequence selected from the group consisting of: SEQ. ID NO: 60, 63, 66, 69, 72, 75, 78, 81, 84, 87 and 90 and a heavy chain complementary determining regions (CDRH2) amino acid sequence having at least 80% identity to an amino acid sequence selected from the group consisting of: SEQ. ID NO: 61, 64, 67, 70, 73, 76, 79, 82, 85, 88 and 91 and a heavy chain complementary determining regions (CDRH3) amino acid sequence having at least 80% identity to an amino acid sequence selected from the group consisting of: SEQ. ID NO: 62, 65, 68, 71, 74, 77, 80, 83, 86, 89 and 92.

In a preferred embodiment, the antibody, recombinant or synthetic antigen-binding fragments thereof as described above further comprises a light chain complementary determining regions (CDRL1) amino acid sequence having at least 80% identity to an amino acid sequence selected from the group consisting of: SEQ. ID NO: 27, 30, 33, 36, 39, 42, 45, 48, 51, 54 and 57 and a light chain complementary determining regions (CDRL2) amino acid sequence having at least 80% identity to an amino acid sequence selected from the group consisting of: SEQ. ID NO: 28, 31, 34, 37, 40, 43, 46, 49, 52, 55 and 58 and a light chain complementary determining regions (CDRL3) amino acid sequence having at least 80% identity to an amino acid sequence selected from the group consisting of: SEQ. ID NO: 29, 32, 35, 38, 41, 44, 47, 50, 53, 56 and 59.

In a yet preferred embodiment, the antibody, recombinant or synthetic antigen-binding fragments thereof as described above comprises a CDRH1 amino acid sequence having at least 80% identity to SEQ ID No. 60, a CDRH2 amino acid sequence having at least 80% identity to SEQ ID No. 61, a CDRH3 amino acid sequence having at least 80% identity to SEQ ID No. 62.

In a still preferred embodiment, the antibody, recombinant or synthetic antigen-binding fragments thereof of the invention further comprises a CDRL1 amino acid sequence having at least 80% identity to SEQ ID No. 27, a CDRL2 amino acid sequence having at least 80% identity to SEQ ID No. 28 and a CDRL3 amino acid sequence having at least 80% identity to SEQ ID No. 29.

In a still preferred embodiment, the antibody, recombinant or synthetic antigen-binding fragments thereof as described above comprises a CDRH1 amino acid sequence having at least 80% identity to SEQ ID No. 81, a CDRH2 amino acid sequence having at least 80% identity to SEQ ID No. 82 and a CDRH3 amino acid sequence having at least 80% identity to SEQ ID No. 83. In a still preferred embodiment, the antibody, recombinant or synthetic antigen-binding fragments thereof of the invention further comprises a CDRL1 amino acid sequence having at least 80% identity to SEQ ID No. 48, a CDRL2 amino acid sequence having at least 80% identity to SEQ ID No. 49 and a CDRL3 amino acid sequence having at least 80% identity to SEQ ID No. 50.

Preferably the antibody, recombinant or synthetic antigen-binding fragments thereof of the invention comprises a CDRH1 amino acid sequence having at least 80% identity to SEQ ID No. 87, a CDRH2 amino acid sequence having at least 80% identity to SEQ ID No. 88 and a CDRH3 amino acid sequence having at least 80% identity to SEQ ID No. 89. Still preferably, the antibody, recombinant or synthetic antigen-binding fragments thereof further comprises a CDRL1 amino acid sequence having at least 80% identity to SEQ ID No. 54, a CDRL2 amino acid sequence having at least 80% identity to SEQ ID No. 55 and a CDRL3 amino acid sequence having at least 80% identity to SEQ ID No. 56.

In the present invention "at least 80% identity" means that the identity may be at least 80% or at least 85% or 90% or 95% or 100% sequence identity to referred sequences.

Preferably, the antibody, recombinant or synthetic antigen-binding fragments thereof as described above is a monoclonal antibody or a chimeric or a humanized, or a deimmunized or a fully human antibody.

It is a further object of the invention, the antibody, recombinant or synthetic antigen-binding fragments thereof as described above for medical use. Preferably, for use in the treatment and/or prevention of a condition associated with cartilage degradation, such as osteoarthritis and/or rheumatoid arthritis. Preferably the antibody, recombinant or synthetic antigen-binding fragments thereof as described above may be used for the treatment of pathological responses mediated by Syndecan-4, in particular pathological responses of chondrocytes mediated by Syndecan-4.

It is a further object of the invention a nucleic acid molecule encoding the antibody, recombinant or synthetic antigen-binding fragments thereof as defined above. Preferably, the nucleic acid molecule encoding the antibody, recombinant or synthetic antigen-binding fragments thereof of the invention comprises at least one nucleic acid sequence selected from the group consisting of SEQ ID No. 99 to SEQ ID No. 120. Preferably, the nucleic acid comprises at least one of the following sequences: SEQ ID NO.: 99, 100, 113, 114, 117 and 118.

It is a further object of the invention an expression vector encoding the antibody, recombinant or synthetic antigen-binding fragments thereof of the invention.

It is a further object of the invention a host cell comprising the nucleic acid as described above. Preferably, the host cell produces the antibody, recombinant or synthetic antigen-binding fragments thereof of the invention.

It is a further object of the invention a method of producing the antibody, recombinant or synthetic antigen-binding fragments thereof of the invention comprising culturing the cell that produces the antibody as described above and recovering the antibody from the cell culture.

It is another object of the invention a pharmaceutical composition comprising at least one antibody, recombinant or synthetic antigen-binding fragments thereof as described above and pharmaceutically acceptable excipients. The composition comprises an effective amount of the antibody, recombinant or synthetic antigen-binding fragments thereof. Pharmaceutical compositions are conventional in this field and can be made by the person skilled in the art just based on the common general knowledge. Pharmaceutical compositions comprising the antibody and/or a fragment and/or a recombinant derivative and/or a conjugate thereof in admixture with at least one pharmaceutically acceptable excipient and/or vehicle are included in the scope of the present invention.

In a preferred embodiment, the composition according to the invention is for use in intra-articular administration.

It is also an object of the invention a method of treating and/or preventing a condition associated with cartilage degradation, such as osteoarthritis, rheumatoid arthritis and other forms of arthritides comprising administering a therapeutically effective amount the antibody, recombinant or synthetic antigen-binding fragments thereof as described above. It is also an object of the invention a method for treating and/or preventing joint destruction, for the treatment and/or prevention of autoimmune and/or inflammatory diseases comprising administering an therapeutic effective amount of the antibody, recombinant or synthetic antigen-binding fragments thereof as described above.

It is an object of the invention a method of reducing and/or inhibiting ADAMTS-5 comprising administering an effective amount of the antibody, recombinant or synthetic antigen-binding fragments thereof as described above.

In the present invention mutants of the disclosed CDRs may be generated by mutating one or more amino acids in the sequence of the CDRs. It is known that a single amino acid substitution appropriately positioned in a CDR can be sufficient to improve the affinity. Researchers have used site directed mutagenesis to increase affinity of some immunoglobulin products by about 10 fold. This method of increasing or decreasing (i.e modulating) affinity of antibodies by mutating CDRs is common knowledge (see, e.g., Paul, W. E., 1993). Thus, the substitution, deletion, or addition of amino acids to the CDRs of the invention to increase or decrease (i.e, modulate) binding affinity or specificity is also within the scope of this invention.

For sake of brevity, the preferred antibody according to the present invention shall be identified with the name CRB0017 (comprising SEQ ID No. 3 and SEQ ID No. 4), CRB0102 (comprising SEQ ID No. 17 and SEQ ID No. 18) and CRB0123 (comprising SEQ ID No. 21 and SEQ ID No. 22) as indicated in Table III. While the present invention focuses on such antibodies, as an exemplification of the present invention, one of ordinary skill in the art will appreciate that, once given the present disclosure, other similar antibodies, and antibody fragments thereof, as well as antibody fragments of these similar antibodies may be produced and used within the scope of the present invention. Such similar antibodies may be produced by a reasonable amount of experimentation by those skilled in the art.

Still preferably, the antibody is a scFv, Fv fragment, a Fab fragment, a F(ab)2 fragment, a multimeric antibody, a peptide or a proteolytic fragment containing the epitope binding region. Preferably the scFv fragment comprises a sequence selected from the group of SEQ ID No. 125 to 132 and SEQ ID no. 135, 136, 137.

It is a further object of the present invention a nucleic acid encoding the antibody or functional derivatives thereof of the invention, or hybridizing with the above nucleic acid, or consisting of a degenerated sequence thereof.

The process for the preparation of the monoclonal antibody is within the skills of the man skilled in the art and comprises cultivating host cell and isolating the antibody according to standard procedures.

As far as the industrial aspects of the present invention are concerned, the antibody herein disclosed shall be suitably formulated in pharmaceutical compositions as normally done in this technical field.

The antibodies of the present invention may comprises at least one CDRH as defined above that contains one or more amino acid substitutions, deletions or insertions of no more than 4 amino acids, preferably of no more than 2 amino acids. The antibodies of the present invention may further comprises at least one CDRL as defined above that contains one or more amino acid substitutions, deletions or insertions of no more than 4 amino acids, preferably of no more than 2 amino acids.

The antibodies of the invention compete for binding to ADAMTS-5. The method for treating or preventing a condition associated with cartilage degradation, comprises administering to a patient in need thereof an effective amount of at least one antibody, recombinant or synthetic antigen-binding fragments thereof as described above. In some aspects, the invention comprises a method of inhibiting binding of ADAMTS-5 to aggrecan in a subject comprising administering an effective amount of at least one antibody, recombinant or synthetic antigen-binding fragments thereof as described above.

The antibodies, recombinant or synthetic antigen-binding fragments thereof of the invention selectively bind to Spacer domain of ADAMTS-5, preferably with a Kd that is ≤2 nM.

In some aspects, the invention comprises a method for treating or preventing a condition associated with cartilage degradation in a subject, the method comprising administering to a subject in need thereof an effective amount of at least one antibody, recombinant or synthetic antigen-binding fragments thereof of the invention simultaneously or sequentially with an agent that specifically blocks pain.

The antibody, recombinant or synthetic antigen-binding fragments thereof of the invention are neutralizing antibody (i.e an antibody that reduces or abolishes the biological activity of the related antigen) that binds to ADAMTS-5 and reduces the likelihood that ADAMTS-5 binds to aggrecan.

Preferably, the antibody, recombinant or synthetic antigen-binding fragments thereof of the invention bind to ADAMTS-5 at a location within residues 732-874 of SEQ. ID NO: 2. In some embodiments, the antibody, recombinant or synthetic antigen-binding fragments thereof of the invention, when bound to ADAMTS-5, is positioned 8 angstroms or less from at least one of the following residues of ADAMTS-5: T732, K733, I734, V735, G736, T737, F738, N739, K740, K741, S742, K743, G744, Y745, T746, D747, V748, V749, R750, I751, P752, E753, G754, A755, T756, H757, I758, K759, V760, R761, Q762, F763, K764, A765, K766, D767, Q768, T769, R770, F771, T772, A773, Y774, L775, A776, L777, K778, K779, K780, N781, G782, E783, Y784, L785, I786, N787, G788, K789, Y790, M791, I792, S793, T794, S795, E796, T797, I798, I799, D800, I801, N802, G803, T804, V805, M806, N807, Y808, S809, G810, W811, S812, H813, R814, D815, D816, F817, L818, H819, G820, M821, G822, Y823, S824, A825, T826, K827, E828, I829, L830, I831, V832, Q833, I834, L835, A836, T837, D838, P839, T840, K841, P842, L843, D844, V845, R846, Y847, S848, F849, F850, V851, P852, K853, K854, S855, T856, P857, K858, V859, N860, S861, V862, T863, S864, H865, G866, S867, N868, K869, V870, G871, S872, H873 or T874.

In some embodiments, the antibody, recombinant or synthetic antigen-binding fragments thereof of the invention blocks an antibody to ADAMTS-5 from binding within 8 angstroms of a residue of ADAMTS-5. In some embodiments the residue of ADAMTS-5 is selected from at least one of the following ADAMTS-5 residues: T732, K733, I734, V735, G736, T737, F738, N739, K740, K741, S742, K743, G744, Y745, T746, D747, V748, V749, R750, I751, P752, E753, G754, A755, T756, H757, I758, K759, V760, R761, Q762, F763, K764, A765, K766, D767, Q768, T769, R770, F771, T772, A773, Y774, L775, A776, L777, K778, K779, K780, N781, G782, E783, Y784, L785, I786, N787, G788, K789, Y790, M791, I792, S793, T794, S795, E796, T797, I798, I799, D800, I801, N802, G803, T804, V805, M806, N807, Y808, S809, G810, W811, S812, H813, R814, D815, D816, F817, L818, H819, G820, M821, G822, Y823, S824, A825, T826, K827, E828, I829, L830, I831, V832, Q833, I834, L835, A836, T837, D838, P839, T840, K841, P842, L843, D844, V845, R846, Y847, S848, F849, F850, V851, P852, K853, K854, S855, T856, P857, K858, V859, N860, S861, V862, T863, S864, H865, G866, S867, N868, K869, V870, G871, S872, H873 or T874.

Preferably, the antibody, recombinant or synthetic antigen-binding fragments thereof of the invention binds to ADAMTS-5 at a location that overlaps with a location at which aggrecan binds to ADAMTS-5.

Preferably, the antibody, recombinant or synthetic antigen-binding fragments thereof of the invention reduces the likelihood that aggrecan will bind to ADAMTS-5 within 8 angstroms of at least one of the following residues on ADAMTS-5: T732, K733, I734, V735, G736, T737, F738, N739, K740, K741, S742, K743, G744, Y745, T746, D747, V748, V749, R750, I751, P752, E753, G754, A755, T756, H757, I758, K759, V760, R761, Q762, F763, K764, A765, K766, D767, Q768, T769, R770, F771, T772, A773, Y774, L775, A776, L777, K778, K779, K780, N781, G782, E783, Y784, L785, I786, N787, G788, K789, Y790, M791, I792, S793, T794, S795, E796, T797, I798, I799, D800, I801, N802, G803, T804, V805, M806, N807, Y808, S809, G810, W811, S812, H813, R814, D815, D816, F817, L818, H819, G820, M821, G822, Y823, S824, A825, T826, K827, E828, I829, L830, I831, V832, Q833, I834, L835, A836, T837, D838, P839, T840, K841, P842, L843, D844, V845, R846, Y847, S848, F849, F850, V851, P852, K853, K854, S855, T856, P857, K858, V859, N860, S861, V862, T863, S864, H865, G866, S867, N868, K869, V870, G871, S872, H873 or T874.

The invention provides formulations comprising a therapeutically effective amount of an antibody as disclosed herein, a buffer maintaining the pH in the range from about 4.5 to about 6.5, and, optionally, a surfactant.

The formulations are typically for an antibody as disclosed herein, recombinant or synthetic antigen-binding fragments thereof of the invention as active principle concentration from about 0.1 mg/ml to about 100 mg/ml. In certain embodiments, the antibody, recombinant or synthetic antigen-binding fragments thereof concentration is from about 0.1 mg/ml to 1 mg/ml; preferably from 1 mg/ml to 10 mg/ml, preferably from 10 to 100 mg/ml.

For the purposes herein, a "pharmaceutical composition" is one that is adapted and suitable for administration to a mammal, especially a human. Thus, the composition can be used to treat a disease or disorder in the mammal. Moreover, the antibody in the composition has been subjected to one or more purification or isolation steps, such that contaminant(s) that might interfere with its therapeutic use have been separated therefrom. Generally, the pharmaceutical composition comprises the therapeutic protein and a pharmaceutically acceptable carrier or diluent. The composition is usually sterile and may be lyophilized. Pharmaceutical preparations are described in more detail below.

Therapeutic formulations of the antibody/antibodies can be prepared by mixing the antibody having the desired degree of purity with optional physiologically acceptable carriers, excipients or stabilizers (Remington's Pharmaceutical Sciences 16th edition, Osol, A. Ed., 1980), in the form of lyophilized formulations or aqueous solutions. Acceptable carriers, excipients, or stabilizers are nontoxic to recipients at the dosages and concentrations employed, and may include buffers, antioxidants, preservatives, peptides, proteins, hydrophilic polymers, chelating agents such as EDTA, sugars, salt-forming counter-ions such as sodium; metal complexes (e.g., Zn-protein complexes); and/or non-ionic surfactants such as TWEEN®, PLURONICS® or polyethylene glycol (PEG).

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed., 1980). The formulations to be used for in vivo administration must be sterile. This is readily accomplished by filtration through sterile filtration membranes.

In another embodiment, for the prevention or treatment of disease, the appropriate dosage of anti-Sp-ADAMTS-5 antibody/antibodies of the present invention, will depend on the type of disease to be treated, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg of antibody or fragment thereof is an initial candidate dosage for administration to the patient, whether, for example, by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

The antibody composition should be formulated, dosed, and administered in a fashion consistent with good medical practice. The antibodies/derivatives of the present invention can be administered by any appropriate route. This includes (but is not limited to) intraperitoneal, intramuscular, intravenous, subcutaneous, intraarticular, intratracheal, oral, enteral, parenteral, intranasal or dermal administration. A preferred mode of administration is the intraarticular route. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat a disease or disorder. The antibody need not be, but is optionally formulated with one or more agents currently used to prevent or treat the disorder in question. The effective amount of such other agents depends on the amount of antibody present in the formulation, the type of disorder or treatment, and other factors discussed above.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein. The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called [alpha], [delta], [epsilon], [gamma], and [mu], respectively.

The term "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4. The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "deimmunized" antibody is an antibody with reduced immunogenicity based on disruption of HLA binding, an underlying requirement for T cell stimulation.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (HI, H2, H3), and three in the VL (LI, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (LI), 50-52 (L2), 91-96 (L3), 26-32 (HI), 53-55 (H2), and 96-101 (H3) (Chothia and Lesk, J. Mol. Biol. 196:901-917, 1987). Exemplary CDRs (CDR-L1, CDR-L2, CDR-L3, CDR-H1, CDR-H2, and CDR-H3) occur at amino acid residues 24-34 of LI, 50-56 of L2, 89-97 of L3, 31-35B of HI, 50-65 of H2, and 95-102 of H3 (Kabat et al., Sequences of Proteins of Immunological Interest, 5th Ed. Public Health Service, National Institutes of Health, Bethesda, Md., 1991). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of LI, 50-55 of L2, 89-96 of L3, 31-35B of HI, 50-58 of H2, and 95-102 of H3 (See Almagro and Fransson, Front. Biosci. 13: 1619-1633, 2008). Unless otherwise indicated, HVR residues and other residues in the variable domain (e.g., FR residues) are numbered herein according to Kabat et al.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs, See, e.g., Kindt et al. Kuby Immunology, 6th ed., W.H. Freeman and Co., page 91, 2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (See, e.g., Portolano et al., J. Immunol. 150:880-887, 1993; Clarkson et al., Nature 352:624-628, 1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

In another aspect, the antibody or derivatives thereof comprises a heavy chain variable domain (VH) sequence having at least 80%, 85%, 90%, 91%, 92%, 93%, 94%, 95%, 96%, 97%, 98%, 99%, or 100% sequence identity to an amino acid sequence selected from the group of: SEQ ID NO: 4, 6, 8, 10, 12, 14, 16, 18, 20, 22 or 24.

In another aspect, the antibody or derivatives thereof comprises a light chain variable domain (VK or VL) sequence having at least 80%, 85%, 90%, 91%, 92%, 93%, 94%, 95%, 96%, 97%, 98%, 99%, or 100% sequence identity to an amino acid sequence selected from the group of: SEQ ID NO: 3, 5, 7, 9, 11, 13, 15, 17, 19, 21 or 23.

In certain embodiments, the VH sequence or VK/VL sequence having at least 80%, 85%, 90%, 91%, 92%, 93%, 94%, 95%, 96%, 97%, 98%, or 99% identity to said SEQ ID No. contains substitutions (e.g., conservative substitutions), insertions, or deletions relative to the reference sequence, but an anti-Sp-ADAMTS-5 antibody comprising that sequence retains the ability to bind to the spacer domain of ADAMTS-5. In certain embodiments, a total of 1 to 4 amino acids have been substituted, inserted and/or deleted in the sequence of the CDRH3 such as in SEQ ID No. 62. In certain embodiments, substitutions, insertions, or deletions occur in regions outside the HVRs (i.e., in the FRs).

Preferably, the antibody of the invention is antibody CRB0017, CRB0093, CRB0094, CRB0102, CRB0123, CRB0124, as defined in Table III.

In certain embodiments, the antibody or fragment thereof of the invention has a dissociation constant (Kd) of <100 nM, <10 nM, <1 nM, <0.1 nM, <0.01 nM, or <0.001 nM or less, e.g. from 10-8 M to $10^{-13}$M, e.g., from $10^{-9}$ M to $10^{-13}$ M.

In one embodiment, Kd is measured by a radio labeled antigen binding assay (RIA) performed with the Fab version of an antibody of interest and its antigen as described by the following assay. Solution binding affinity of Fabs for antigen is measured by equilibrating Fab with a minimal concentration of (I)-labeled antigen in the presence of a titration series of unlabeled antigen, then capturing bound antigen with an anti-Fab antibody-coated plate (see, e.g., Chen et al., J. Mol. Biol. 293:865-881(1999)).

BRIEF DESCRIPTION OF THE DRAWINGS

The invention will be described now by non-limiting examples referring to the following figures.

Figure 13:
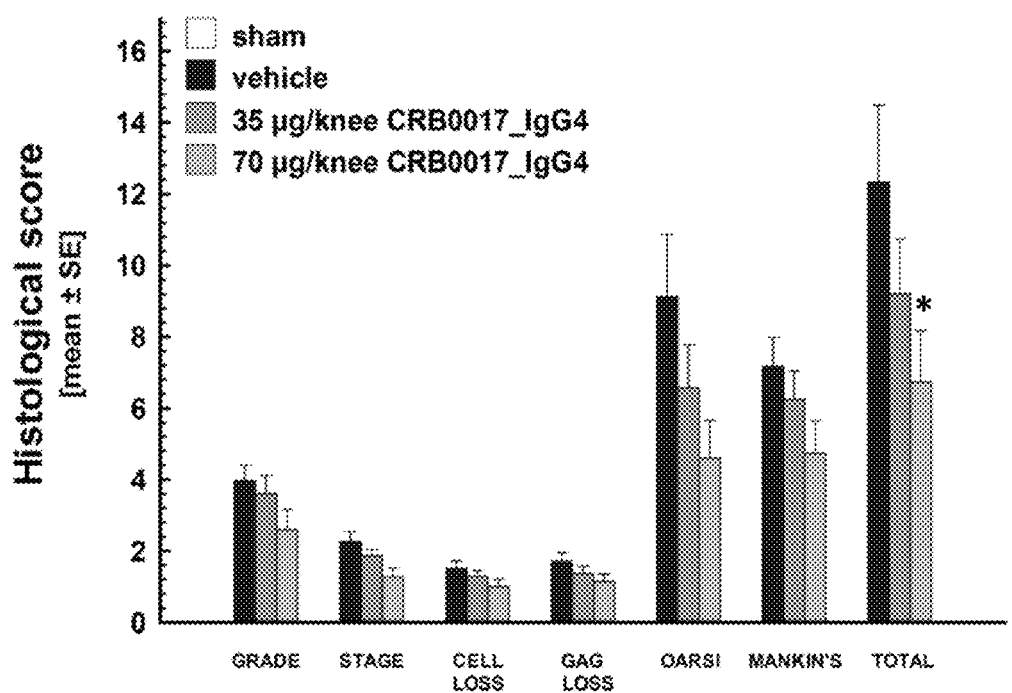

FIG. 13. Unilateral medial meniscal tear model (MMT) is a widely used rat surgical model of knee OA. Rapidly progressive degenerative changes occur, that consist in chondrocyte and proteoglycan loss, matrix fibrillation and clefting, osteophyte formation. One week after surgery, rats were treated intraarticularly with CRB0017_IgG4 35 µg/knee, CRB0017 70 µg/knee, or vehicle. After 3 weeks from injection the animals were sacrificed and the femorotibial joints processed for histology. All histological scores were dose-dependently decreased by treatment with CRB0017_IgG4 compared to vehicle.

Figure 14:
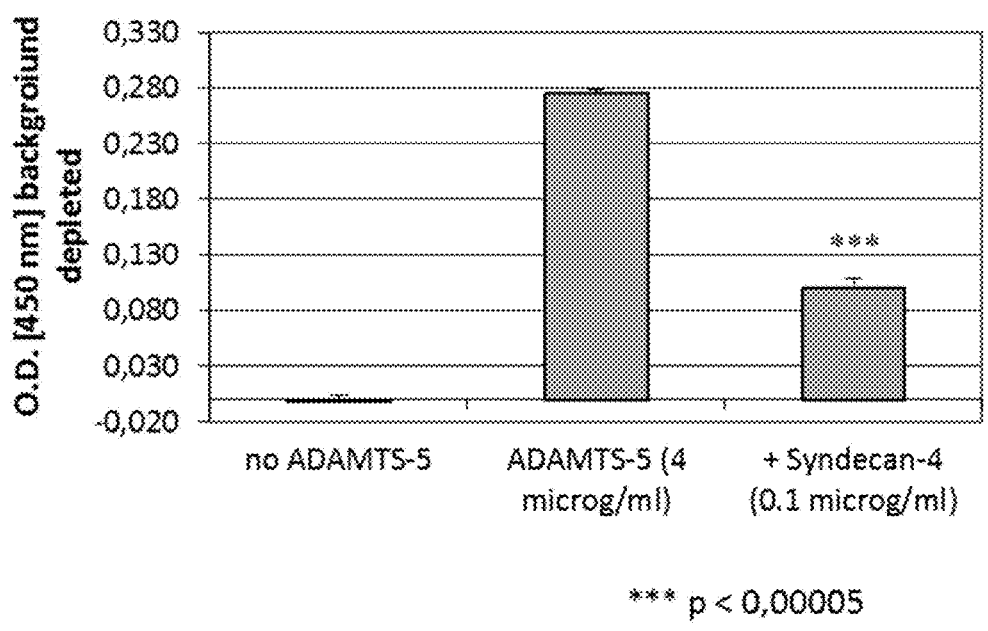

FIG. 14. Competitive inhibition of mAb ADAMTS-5 binding to mAb CRB0017-coated plates by free Syndecan-4. mAb CRB0017 (2 µg/ml in coating buffer) were adsorbed to immunoplates before blocking ADAMTS-5 (4 µg/ml) in presence of Syndecan-4 (0.1 µg/ml) were incubated before adding to the immobilized mAb CRB0017. ADAMTS-5 binding to mAb CRB0017-coated plates were revealed using anti-FLAG commercial antibody.

Figure 15:
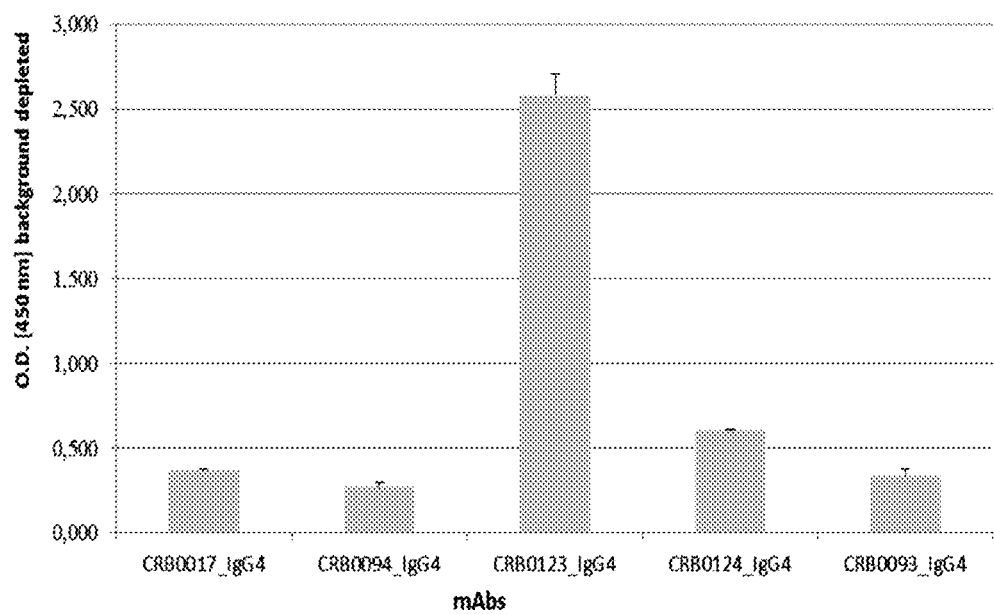

FIG. 15. mAbs anti-spacer CRB0017_IgG4, CRB0093_IgG4, CRB094_IgG4 and CRB0124_IgG4 are able to recognize specifically full length ADAMTS-5 in sandwich ELISA with comparable specificity. mAb CRB0123 IgG4 display a higher binding capacity for ADAMTS-5 than the other anti-spacer mAbs in this assay.

DETAILED DESCRIPTION OF THE INVENTION

Description of the Sequences

SEQ. ID NO:1: ATS4_HUMAN A disintegrin and metalloproteinase with thrombospondin motifs 4 (UniProtKB/Swiss-Prot: O75173.3)

SEQ. ID NO 2: ATS5_HUMAN A disintegrin and metalloproteinase with thrombospondin motifs 5 (UniProtKB/Swiss-Prot: Q9UNA0.2)

In the following: VK=light chain, VH=heavy chain, CDRL=complementary determining region of light chain, CDRH=complementary determining region of heavy chain.

SEQ ID NO: 3 to SEQ ID NO: 94, SEQ ID NO: 125 to 132 and SEQ ID NO: 135 to SEQ ID NO: 137 are amino acid sequences, SEQ ID NO:95 to 120 are nucleotide sequences.

SEQ. ID NO: 3, CRB0017VK
SEQ. ID NO: 4, CRB0017VH
SEQ. ID NO: 5, CRB0018VK
SEQ. ID NO: 6, CRB0018VH
SEQ. ID NO: 7, CRB0019VK
SEQ. ID NO: 8, CRB0019VH
SEQ. ID NO: 9, CRB0091VK
SEQ. ID NO: 10, CRB0091VH
SEQ. ID NO: 11, CRB0092VL
SEQ. ID NO: 12, CRB0092VH
SEQ. ID NO: 13, CRB0093VK
SEQ. ID NO: 14, CRB0093VH
SEQ. ID NO: 15, CRB0094VL
SEQ. ID NO: 16, CRB0094VH
SEQ. ID NO: 17, CRB0102VK
SEQ. ID NO: 18, CRB0102VH
SEQ. ID NO: 19, CRB0122VL
SEQ. ID NO: 20, CRB0122VH
SEQ. ID NO: 21, CRB0123VK
SEQ. ID NO: 22, CRB0123VH
SEQ. ID NO: 23, CRB0124VL
SEQ. ID NO: 24, CRB0124VH
SEQ. ID NO: 25, CRB0016VK
SEQ. ID NO: 26, CRB0016VH
SEQ. ID NO: 27, CDRL1_17
SEQ. ID NO: 28, CDRL2_17
SEQ. ID NO: 29, CDRL3_17
SEQ. ID NO: 30, CDRL1_18
SEQ. ID NO: 31, CDRL2_18
SEQ. ID NO: 32, CDRL3_18
SEQ. ID NO: 33, CDRL1_19
SEQ. ID NO: 34, CDRL2_19
SEQ. ID NO: 35, CDRL3_19
SEQ. ID NO: 36, CDRL1_91
SEQ. ID NO: 37, CDRL2_91
SEQ. ID NO: 38, CDRL3_91
SEQ. ID NO: 39, CDRL1_92
SEQ. ID NO: 40, CDRL2_92
SEQ. ID NO: 41, CDRL3_92
SEQ. ID NO: 42, CDRL1_93
SEQ. ID NO: 43, CDRL2_93
SEQ. ID NO: 44, CDRL3_93
SEQ. ID NO: 45, CDRL1_94
SEQ. ID NO: 46, CDRL2_94
SEQ. ID NO: 47, CDRL3_94
SEQ. ID NO: 48, CDRL1_102
SEQ. ID NO: 49, CDRL2_102
SEQ. ID NO: 50, CDRL3_102
SEQ. ID NO: 51, CDRL1_122
SEQ. ID NO: 52, CDRL2_122
SEQ. ID NO: 53, CDRL3_122
SEQ. ID NO: 54, CDRL1_123
SEQ. ID NO: 55, CDRL2_123
SEQ. ID NO: 56, CDRL3_123
SEQ. ID NO: 57, CDRL1_124
SEQ. ID NO: 58, CDRL2_124
SEQ. ID NO: 59, CDRL3_124
SEQ. ID NO: 60, CDRH1_17
SEQ. ID NO: 61, CDRH2_17
SEQ. ID NO: 62, CDRH3_17
SEQ. ID NO: 63, CDRH1_18
SEQ. ID NO: 64, CDRH2_18
SEQ. ID NO: 65, CDRH3_18
SEQ. ID NO: 66, CDRH1_19
SEQ. ID NO: 67, CDRH2_19
SEQ. ID NO: 68, CDRH3_19
SEQ. ID NO: 69, CDRH1_91
SEQ. ID NO: 70, CDRH2_91
SEQ. ID NO: 71, CDRH3_91
SEQ. ID NO: 72, CDRH1_92
SEQ. ID NO: 73, CDRH2_92
SEQ. ID NO: 74, CDRH3_92
SEQ. ID NO: 75, CDRH1_93
SEQ. ID NO: 76, CDRH2_93
SEQ. ID NO: 77, CDRH3_93
SEQ. ID NO: 78, CDRH1_94
SEQ. ID NO: 79, CDRH2_94
SEQ. ID NO: 80, CDRH3_94
SEQ. ID NO: 81, CDRH1_102
SEQ. ID NO: 82, CDRH2_102
SEQ. ID NO: 83, CDRH3_102
SEQ. ID NO: 84, CDRH1_122
SEQ. ID NO: 85, CDRH2_122
SEQ. ID NO: 86, CDRH3_122
SEQ. ID NO: 87, CDRH1_123
SEQ. ID NO: 88, CDRH2_123
SEQ. ID NO: 89, CDRH3_123
SEQ. ID NO: 90, CDRH1_124
SEQ. ID NO: 91, CDRH2_124

SEQ. ID NO: 92, CDRH3_124
SEQ. ID NO: 93, lexA-Spacer
SEQ. ID NO: 94, Spacer-GST
SEQ. ID NO: 95, CRB0016_VK
SEQ. ID NO: 96, CRB0016_IgG4
SEQ. ID NO: 97, CRB0017_VK_CK
SEQ. ID NO: 98, CRB0017_IgG4
SEQ. ID NO: 99, CRB0017_VK
SEQ. ID NO: 100, CRB0017_VH
SEQ. ID NO: 101, CRB0018_VK
SEQ. ID NO: 102, CRB0018_VH
SEQ. ID NO: 103, CRB0019_VK
SEQ. ID NO: 104, CRB0019_VH
SEQ. ID NO: 105, CRB0091_VK
SEQ. ID NO: 106, CRB0091_VH
SEQ. ID NO: 107, CRB0092_VL
SEQ. ID NO: 108, CRB0092_VH
SEQ. ID NO: 109, CRB0093_VK
SEQ. ID NO: 110, CRB0093_VH
SEQ. ID NO: 111, CRB0094_VL
SEQ. ID NO: 112, CRB0094_VH
SEQ. ID NO: 113, CRB0102_VL
SEQ. ID NO: 114, CRB0102_VH
SEQ. ID NO: 115, CRB0122_VL
SEQ. ID NO: 116, CRB0122_VH
SEQ. ID NO: 117, CRB0123_VK
SEQ, ID NO: 118, CRB0123_VH
SEQ. ID NO: 119, CRB0124_VL
SEQ. ID NO: 120, CRB0124_VH
SEQ. ID NO: 121, HUMAN SPACER DOMAIN_AA
SEQ. ID NO: 122, HELIX_B_ADAMTS-5_AA
SEQ. ID NO: 123, HUMAN SPACER DOMAIN
SEQ. ID NO: 124, HELIX_B_ADAMTS-5
SEQ. ID NO: 125, CRB0017_scFv
SEQ. ID NO: 126, CRB0018_scFv
SEQ. ID NO: 127, CRB0019_scFv
SEQ. ID NO: 128, CRB0091_scFv
SEQ. ID NO: 129, CRB0092_scFv
SEQ. ID NO: 130, CRB0093_scFv
SEQ. ID NO: 131, CRB0094_scFv
SEQ. ID NO: 132, CRB0102_scFv
SEQ. ID NO: 133, HUMAN ADAMTS-5_cDNA
SEQ. ID NO: 134, HUMAN ADAMTS-4_cDNA
SEQ. ID NO: 135, CRB0122_scFv
SEQ. ID NO: 136, CRB0123_scFv
SEQ. ID NO: 137, CRB0124_scFv
SEQ. ID NO: 138, small peptide linker
SEQ. ID NO: 139-216, synthetic primers Materials and Methods SPLINT Library from Human Lymphocytes.

The development of therapeutic antibodies for use in the treatment of human diseases has long been a goal for many researchers in the antibody field. One way to obtain these antibodies is through Single Pot Library of Intracellular Antibodies (SPLINT libraries) constructed from human lymphocytes. SPLINT technology expresses human scFv (single chain antibody fragment) libraries cloned in pMV1 vector, a vector derived from pLinker220 vector (Visintin et al., 2004. J Immunol Methods. 290:135-153), as fusion to the VP16 activation domain. The variable regions are linked with a small peptide linker (SGGSTSGSGKPGSGEGSSGT, SEQ ID No. 138). pMV1 contains LEU2 gene that permits maintenance of the plasmid and selection on media lacking leucine in yeast strain L40 and the bla gene that permits the selection of plasmid in *E. coli*.

For construction of human SPLINT libraries the peripheral blood donations from one hundred, non-immunized donors were used. Approximately 2-20 ml of blood samples from each donor were collected. B-lymphocytes were isolated from peripheral blood by using Ficoll plaque reagent (Amersham, USA). Briefly, the diluted blood sample (1:1 of blood per PBS) was carefully layered on top of the Ficoll plaque reagent, and then the two phase solution was centrifuged at 400×g for 30 minutes. B-lymphocytes were collected from the interface between the two phases. Total RNA was extracted from B-lymphocytes by RNeasy Mini Kit (Qiagen) according to manufacturer's instruction. Total RNA was prepared from the B lymphocytes and pooled together before being used for the isolation of mRNA. mRNA was prepared using Oligotex mRNA mini kit (Qiagen) according to manufacturer's instruction. ThermoScript™ RT-PCR System (Invitrogen) was used for cDNA synthesis reactions according to manufacturer's instruction. Oligo (dT)20 were used to synthesize cDNA of V-genes repertoire. In order to reduce amplification bias, the authors performed 62 (for huSPLINT_09) and 75 (for huSPLINT_10) independent PCR reactions to amplify V gene segments, using all possible combinations within a primer set (for huSPLINT_09 see Table I; for huSPLINT_10 see Table II).

The primer sequences, which in theory encompass the entire repertoire of human antibody genes, were obtained from IMGT/GENE-DB (Giudicelli et al., 2005. *Stud Health Technol Inform.* 116:3-8), and modified according to previously published protocols (Sblattero and Bradbury, 1998. *Immunotechnology.* 3:271-278); (Marks et al., 1991. *Eur J Immunol.* 21:985-991); (Orlandi et al., 1992. *Biotechnology.* 24:527-531). In this method, the individual rearranged heavy- and light-chain variable regions are amplified separately and are linked through a series of overlapping polymerase chain reaction (PCR) steps to give the final scFv products that are used for cloning (Visintin et al., 2004. *J Immunol Methods.* 290:135-153). The PCR reactions for huSPLINT_9 (Table I) included seven VH forward primers paired with four VH reverse primers which generated a total of twenty-eight reactions; whereas four Vκ forward primers paired with four reverse primers generated a total of sixteen reactions; and nine Vλ forward primers paired with two Vλ reverse primers generated a total of eighteen reactions.

TABLE I huSPLINT_09 PCR primers reverse (rv) and forward (fw) for human V-genes chain huSPLINT_09

| PRIMERS | SEQUENCE | |
|---|---|---|
| VHfw | TTATCCTCGAGCGGTACCCAGGTGCAGCTGCAGGAGTCSG | SEQ ID No. 139 |
| | TTATCCTCGAGCGGTACCCAGGTACAGCTGCAGCAGTCA | SEQ ID No. 140 |
| | TTATCCTCGAGCGGTACCCAGGTGCAGCTACAGCAGTGGG | SEQ ID No. 141 |
| | TTATCCTCGAGCGGTACCGAGGTGCAGCTGKTGGAGWCY | SEQ ID No. 142 |
| | TTATCCTCGAGCGGTACCCAGGTCCAGCTKGTRCAGTCTGG | SEQ ID No. 143 |
| | TTATCCTCGAGCGGTACCCAGRTCACCTTGAAGGAGTCTG | SEQ ID No. 144 |
| | TTATCCTCGAGCGGTACCCAGGTGCAGCTGGTGSARTCTGG | SEQ ID No. 145 |

TABLE I -continued huSPLINT_09 PCR primers reverse (rv) and forward (fw) for human V-genes chain huSPLINT_09

| PRIMERS | SEQUENCE | |
|---|---|---|
| VHrv | GATTGGTTTGCCGCTAGCTGAGGAGACRGTGACCAGGGTG | SEQ ID No. 146 |
| | GATTGGTTTGCCGCTAGCTGAGGAGACGGTGACCAGGGTT | SEQ ID No. 147 |
| | GATTGGTTTGCCGCTAGCTGAAGAGACGGTGACCATTGT | SEQ ID No. 148 |
| | GATTGGTTTGCCGCTAGCTGAGGAGACGGTGACCGTGGTCC | SEQ ID No. 149 |
| Vκfw | AGCAAGCGGCGCGCATGCCGACATCCRGDTGACCCAGTCTCC | SEQ ID No. 150 |
| | AGCAAGCGGCGCGCATGCCGAAATTGTRWTGACRCAGTCTCC | SEQ ID No. 151 |
| | AGCAAGCGGCGCGCATGCCGATATTGTGMTGACBCAGWCTCC | SEQ ID No. 152 |
| | AGCAAGCGGCGCGCATGCCGAAACGACACTCACGCAGTCTC | SEQ ID No. 153 |
| Vκrv | GAAGTTATGGTCGACCCTCCGGATTTGATTTCCACCTTGGTCC | SEQ ID No. 154 |
| | GAAGTTATGGTCGACCCTCCGGATTTGATCTCCASCTTGGTCC | SEQ ID No. 155 |
| | GAAGTTATGGTCGACCCTCCGGATTTGATATCCACTTTGGTCC | SEQ ID No. 156 |
| | GAAGTTATGGTCGACCCTCCGGATTTAATCTCCAGTCGTGTCC | SEQ ID No. 157 |
| Vλfw | AGCAAGCGGCGCGCATGCCCAGTCTGTSBTGACGCAGCCGCC | SEQ ID No. 158 |
| | AGCAAGCGGCGCGCATGCCTCCTATGWGCTGACWCAGCCAC | SEQ ID No. 159 |
| | AGCAAGCGGCGCGCATGCCTCCTATGAGCTGAYRCAGCYACC | SEQ ID No. 160 |
| | AGCAAGCGGCGCGCATGCCCAGCCTGTGCTGACTCARYC | SEQ ID No. 161 |
| | AGCAAGCGGCGCGCATGCCCAGDCTGTGGTGACYCAGGAGCC | SEQ ID No. 162 |
| | AGCAAGCGGCGCGCATGCCCAGCCWGKGCTGACTCAGCCMCC | SEQ ID No. 163 |
| | AGCAAGCGGCGCGCATGCCTCCTCTGAGCTGASTCAGGASCC | SEQ ID No. 164 |
| | AGCAAGCGGCGCGCATGCCCAGTCTGYYCTGAYTCAGCCT | SEQ ID No. 165 |
| | AGCAAGCGGCGCGCATGCCAATTTTATGCTGACTCAGCCCC | SEQ ID No. 166 |
| Vλrv | GAAGTTATGGTCGACCCTCCGGATAGGACGGTSASCTTGGTCC | SEQ ID No. 167 |
| | GAAGTTATGGTCGACCCTCCGGAGAGGACGGTCAGCTGGGTGC | SEQ ID No. 168 |
| VL_PTfw | CGCTGGATTGTTATTACTCGCAGCAAGCGGCGCGCATGCC | SEQ ID No. 169 |
| VL_PTrv | ACCGCTCGAGCCTTCACCGGAACCTGGTTTCCCAGAACCGCTGGTCGACCCTCC | SEQ ID No. 170 |
| VH_PT fv | GGAGGGTCGACCAGCGGTTCTGGGAAACCAGGTTCCGGTGAAGGCTCGAGCGGTA | SEQ ID No. 171 |
| VH_PTrv | CCAGGCCCAGCAGTGGGTTTGGGATTGGTTTGCCGCTA | SEQ ID No. 172 |
| VL_FINALfw | TACCTATTGCCTACGGCAGCCGCTGGATTGTTATTACTC | SEQ ID No. 173 |
| VH_FINALrv | TGGTGATGGTGAGTACTATCCAGGCCCAGCAGTGGGTTTG | SEQ ID No. 174 |

The PCR reactions for huSPLINT_10 (Table II) included six VH forward primers paired with four VH reverse primers which generated a total of twenty-four reactions; whereas six Vκ forward primers paired with five Vκ reverse primers generated a total of thirty reactions; and seven Vλ forward primers paired with three Vλ reverse primers generated a total of twenty-one reactions.

TABLE II huSPLINT_10 PCR primers reverse (rv) and forward (fw) for human V-genes chain huSPLINT_10

| PRIMERS | SEQUENCE | |
|---|---|---|
| VHfw | AGCAAGCGGCGCGCATGCCCAGGTGCAGCTGGTGCAGTCTGG | SEQ ID No. 175 |
| | AGCAAGCGGCGCGCATGCCCAGGTCAACTTAAGGGAGTCTGG | SEQ ID No. 176 |
| | AGCAAGCGGCGCGCATGCCGAGGTGCAGCTGGTGGAGTCTGG | SEQ ID No. 177 |
| | AGCAAGCGGCGCGCATGCCCAGGTGCAGCTGCAGGAGTCGGG | SEQ ID No. 178 |
| | AGCAAGCGGCGCGCATGCCGAGGTGCAGCTGTTGCAGTCTGC | SEQ ID No. 179 |
| | AGCAAGCGGCGCGCATGCCCAGGTACAGCTGCAGCAGTCAGG | SEQ ID No. 180 |
| VHrv | GAAGTTATGGTCGACCCTCCGGATGAGGAGACGGTGACCAGGGTGCC | SEQ ID No. 181 |
| | GAAGTTATGGTCGACCCTCCGGATGAAGAGACGGTGACCATTGTCCC | SEQ ID No. 182 |
| | GAAGTTATGGTCGACCCTCCGGATGAGGAGACGGTGACCAGGGTTCC | SEQ ID No. 183 |
| | GAAGTTATGGTCGACCCTCCGGATGAGGAGACGGTGACCGTGGTCCC | SEQ ID No. 184 |
| Vκfw | TTATCCTCGAGCGGTACCGACATCCAGATGACCCAGTCTCC | SEQ ID No. 185 |
| | TTATCCTCGAGCGGTACCGATGTTGTGATGACTCAGTCTCC | SEQ ID No. 186 |
| | TTATCCTCGAGCGGTACCGAAATTGTGTTGACGCAGTCTCC | SEQ ID No. 187 |
| | TTATCCTCGAGCGGTACCGACATCGTGATGACCCAGTCTCC | SEQ ID No. 188 |
| | TTATCCTCGAGCGGTACCGAAACGACACTCACGCAGTCTCC | SEQ ID No. 189 |
| | TTATCCTCGAGCGGTACCGAAATTGTGCTGACTCAGTCTCC | SEQ ID No. 190 |

TABLE II -continued huSPLINT_10 PCR primers reverse (rv) and forward (fw) for human V-genes chain huSPLINT_10

| PRIMERS | SEQUENCE |
|---|---|
| Vκrv | GATTGGTTTGCCGCTAGCACGTTTGATTTCCACCTTGGTCCC SEQ ID No. 191 |
| | GATTGGTTTGCCGCTAGCACGTTTGATCTCCAGCTTGGTCCC SEQ ID No. 192 |
| | GATTGGTTTGCCGCTAGCACGTTTGATATCCACTTTGGTCCC SEQ ID No. 193 |
| | GATTGGTTTGCCGCTAGCACGTTTGATCTCCACCTTGGTCCC SEQ ID No. 194 |
| | GATTGGTTTGCCGCTAGCACGTTTAATCTCCAGTCGTGTCCC SEQ ID No. 195 |
| Vλfw | TTATCCTCGAGCGGTACCCAGTCTGTGTTGACGCAGCCGCC SEQ ID No. 196 |
| | TTATCCTCGAGCGGTACCCAGTCTGCCCTGACTCAGCCTGC SEQ ID No. 197 |
| | TTATCCTCGAGCGGTACCTCCTATGTGCTGACTCAGCCACC SEQ ID No. 198 |
| | TTATCCTCGAGCGGTACCTCTTCTGAGCTGACTCAGGACCC SEQ ID No. 199 |
| | TTATCCTCGAGCGGTACCCACGTTATACTGACTCAACCGCC SEQ ID No. 200 |
| | TTATCCTCGAGCGGTACCCAGGCTGTGCTCACTCAGCCGTC SEQ ID No. 201 |
| Vλrv | GATTGGTTTGCCGCTAGCACCTAGGACGGTGACCTTGGTCCC SEQ ID No. 202 |
| | GATTGGTTTGCCGCTAGCACCTAGGACGGTCAGCTTGGTCCC SEQ ID No. 203 |
| | GATTGGTTTGCCGCTAGCACCTAAAACGGTGAGCTGGGTCCC SEQ ID No. 204 |
| VH_PTfw | CGCTGGATTGTTATTACTCGCAGCAAGCGGCGCGCATGCC SEQ ID No. 205 |
| VH_PTrv | ACCGCTCGAGCCTTCACCGGAACCTGGTTTCCCAGAACCGCTGGTCGACCCTCC SEQ ID No. 206 |
| VL_PT fv | GGAGGGTCGACCAGCGGTTCTGGGAAACCAGGTTCCGGTGAAGGCTCGAGCGGTA SEQ ID No. 207 |
| VL_PTrv | CCAGGCCCAGCAGTGGGTTTGGGATTGGTTTGCCGCTA SEQ ID No. 208 |
| VH_FINALfw | TACCTATTGCCTACGGCAGCCGCTGGATTGTTATTACTC SEQ ID No. 209 |
| VL_FINALrv | TGGTGATGGTGAGTACTATCCAGGCCCAGCAGTGGGTTTG SEQ ID No. 210 |

The PCRs led to the representation in the repertoire of variable regions derived from all conceivable framework assemblies. All primers contained either BssHII or NheI restriction sites or linker sequence. The final pull-through PCR could be done with two primers (PTfw&PTrv). After the final scFv gene repertoires had been sequentially digested with BssHII and NheI, they were ligated directly into pre-digested and dephosphorylated pMV1 vector. From one ligation reaction and thirty electroporations for each library, the authors were able to obtain the final huSPLINT_09 and huSPLINT_10 libraries each consisting of ~$10^8$ different scFv molecules with 0.04% of clones from no-insert ligation.

Cloning of Spacer-ADAMTS-5 Bait and Expression in Yeast Cell L40.

cDNA encoding human Spacer-ADAMTS-5 (SEQ. ID No. 123) was amplified from ADAMTS-5 pSecTag2A using primers:

SEQ ID No. 211
5'-TGGCTGGAATTCACAAAGATTGTTGGA-3'

SEQ ID No. 212
5'-GTCGACGGATCCTTAAGTGTGTGATCCCAC-3'

The EcoRI-BamHI digested cDNA was cloned into pMICBD1 vector (Visintin et al., 2004. *J Immunol Methods*. 290:135-153) designed to contain bacterial chloramphenicol resistance, TRP1 gene (which allows yeast containing this plasmid to grow in minimal medium lacking tryptophan) and the 2μ origin of replication. This plasmid contains the entire region of the *Escherichia coli* lexA protein, expressed from the yeast alcohol dehydrogenase I (ADH1) promoter, followed by a polylinker for cDNA insertion, to generate in-frame fusions to lexA. Bait was sequenced to confirm in-frame fusion of the insert with lexA binding domain in the vector.

L40 yeast cells were transfected with bait Sp_ADAMTS-5/MICBD1 vector by using lithium acetate transformation protocol. The transformants were assayed for histidine prototropy on YC-Lys/-Ura/-His/-Trp plates (Visintin and Cattaneo, 2001. *Antibody Engineering*. 1:790; Visintin et al., 2004. *J Immunol Methods*. 290:135-153.; Visintin et al., 2004. *Methods*. 34:200-214; Visintin et al., 2002. *J Mol Biol*. 317:73-83.; Visintin et al., 1999. *Proc Natl Acad Sci USA*. 96:11723-11728). Yeast colonies were assayed for β-galactosidase activity using colony lift filters, as previously described (Visintin and Cattaneo, 2001. Antibody Engineering. 1:790). The transfection of the bait did not result in activation of the lacZ gene (data not shown).

Cloning of HelixB-ADAMTS-5 Bait and Expression in Yeast Cell L40.

cDNA encoding an α-helix (helixB, SEQ. ID No. 124) at the surface position of the human catalytic domain of ADAMTS-5 was assembled using primers:

SEQ ID No. 213
5'-AATTCAACGCTGCCACCACACTCAAGAACTTTTGCAAGTGGCAGCACCAACACAACTAACTGCA-3'

SEQ ID No. 214
5'-GTTAGTTGTGTTGGTGCTGCCACTTGCAAAAGTTCTTGAGTGTGGTGGCAGCGTTG-3'

The EcoRI-PstI digested cDNA was cloned into pMICBD1 vector (Visintin et al., 2004. J Immunol Methods. 290:135-153). L40 yeast cells were transfected with bait helixB/MICBD1 vector by using lithium acetate transformation protocol. The transformants were assayed for histidine prototropy on YC-Lys/-Ura/-His/-Trp plates (Visintin and Cattaneo, 2001. Antibody Engineering. 1:790). Yeast colonies were assayed for β-galactosidase activity using colony lift filters, as previously described (Visintin and Cattaneo, 2001. Antibody Engineering. 1:790). The transfection of the bait did not result in activation of the lacZ gene (data not shown).

Western Blot Analysis of Spacer-ADAMTS-5 Bait.

An overnight yeast culture was diluted in 5 ml of YC medium at OD600 0.15 and grown at 30° C. up to OD600 0.6. 1 ml of culture was centrifuged at 10000×g for 5 min and the cell pellet resuspended in Laemmli buffer, resolved on 12% SDS-PAGE, and transferred onto a PVDF membrane (Millipore). Polyclonal antibody anti-LexA (Invitrogen) was used, followed by anti-rabbit-HPR (DAKO). The ECL-chemiluminescence system (Amersham) was used for detection (data not shown).

SPLINT Selections.

SPLINT libraries were transformed into L40 yeast strain expressing the bait (Sp_ADAMTS-5/MICBD1 or HelixB-ADAMTS-5/MICBD1) using the lithium acetate method and the selection as described (Visintin and Cattaneo, 2001. Antibody Engineering. 1:790; Visintin et al., 2004. J Immunol Methods. 290:135-153.; Visintin et al., 2004. Methods. 34:200-214; Visintin et al., 2002. J Mol Biol. 317:73-83.; Visintin et al., 1999. Proc Natl Acad Sci USA. 96:11723-11728). Transformed yeast cells were plated on solid medium lacking Trp (W), Leu (L), Uracil (U), Lys (K) and His (H) (YC-WHULK). Expression of selective marker Trp (W) is provided by pMICBD1 plasmid, Leu (L) by pMV1 plasmid, and Uracil (U), Lys (K) and His (H) are prototroph markers of the yeast strain. Positive clones were grown on selective medium YC-WHULK. β-Galactosidase assays were performed as described (Visintin and Cattaneo, 2001. Antibody Engineering. 1:790; Visintin et al., 2004. J Immunol Methods. 290:135-153.; Visintin et al., 2004. Methods. 34:200-214; Visintin et al., 2002. J Mol Biol. 317:73-83.; Visintin et al., 1999. Proc Natl Acad Sci USA. 96:11723-11728). 11 positive anti-Sp_ADAMTS-5scFvs were isolated after secondary screening from four independent screening of different SPLINT libraries (mSPLINT, huSPLINT_09 and huSPLINT_10). The results of the selections performed for Sp_ADAMTS-5 bait are summarized in Table III.

transformation system (Hanahan, 1983. J Mol Biol. 166: 557-580.) and plate onto LB Kan/Cam plates.

The day after, a single colony was inoculated and diluted into 10 mL LB Kan/Cam media. Transformed bacteria was grown overnight at 37° C. shacking at 250 RPM.

The day after, overnight grown bacteria were diluted in 500 mL LB Kan/Cam media and then paced to grow at 37° C. with 250 RPM shacking since the culture have reached OD(600)=0.7. Then 0.2 mM (final concentration) IPTG was added. Induced bacteria were incubated for 5-6 hours at 25° C. with 250 RPM shacking. Bacteria were finally centrifuged at 6000 RPM for 15 minutes and pellet was frozen at −80° C.

Reformatting of Anti-ADAMTS-5scFvs to Entire IgG Antibodies.

Anti-catalytic_ADAMTS-5 CRB0016 scFv and anti-Sp_ADAMTS-5 CRB0017 scFv were reformatted to entire chimeric IgG antibodies by coupling the murine antigen-binding variable domains to human constant domains. For each antibody the cDNAs encoding the light and heavy chain (Fc from human IgG$_4$) were generated by GENEART (Germany) with suitable restriction sites for subcloning. Sequences were optimized for mammalian expression (CHO-S cell line) (SEQ.ID. NO: 95 and 96; 97 and 98). After synthesis of both chains, the cDNAs were sub-cloned in expression plasmids (pcDNA3.1 derivates containing an extended CMV promoter for expression of the gene of interest) using HindIII and XhoI as cloning sites. For each antibody chain, two expression plasmids were generated: one plasmid containing the cDNA encoding the light chain, one containing the cDNA encoding the heavy chain. The expression plasmid containing the correct inserts was verified by restriction analysis and DNA sequence analysis of the insert.

Anti-Sp_ADAMTS-5 CRB0093, CRB0094, CRB0102, CRB0123 and CRB0124 scFvs were also reformatted to

TABLE III

Summary of Sp_ADAMTS-5 SPLINT selections

| BAIT | SPLINT LIBRARY | N. ≠ CLONES (I screening) | N. ≠ CLONES (II screening) | CLONE | CRB | SEQ ID No. |
|---|---|---|---|---|---|---|
| Sp_ADAMTS-5/MICBD1 | mSPLINT | 15 | 3 | M6 | CRB0017 | 3; 4 |
| | | | | 7A | CRB0018 | 5; 6 |
| | | | | 14 | CRB0019 | 7; 8 |
| Sp_ADAMTS-5/MICBD1 | huSPLINT_09 | 121 | 4 | 7A | CRB0091 | 9; 10 |
| | | | | C21 | CRB0092 | 11; 12 |
| | | | | 47A | CRB0093 | 13; 14 |
| | | | | 48B | CRB0094 | 15; 16 |
| Sp_ADAMTS-5/MICBD1 | huSPLINT_10 | 90 | 1 | 15A | CRB0102 | 17; 18 |
| Sp_ADAMTS-5/MICBD1 | huSPLINT_10 | 99 | 3 | S39 | CRB0122 | 19; 20 |
| | | | | S50 | CRB0123 | 21; 22 |
| | | | | S53a | CRB0124 | 23; 24 |

Cloning and Expression of Recombinant Spacer-ADAMTS-5-GST Protein.

Human Spacer domain of ADAMTS-5 (SEQ. ID NO: 121 and 123) was cloned into Nco-XhoI restriction sites of pET41b (Novagen). The cDNA encoding the Spacer domain was amplified from ADAMTS-5 pSecTag2A using primers:

SEQ ID No. 215
5'-ATCCATGGTCACAAAGATTGTTGGAACC-3'

SEQ ID No. 216
5'-ATCTCGAGTTAAGTGTGTGATCCCACTTTATTG-3'

Sp_ADAMTS-5-GST/pET41b plasmid was transformed into Rosetta 2 (DE3) E. coli (Novagen) by heat shock entire fully human IgG$_4$ antibodies following the cloning procedure adopted for CRB0016 and CRB0017 described above.

Production of Recombinant Chimeric CRB0016 IgG4 and CRB0017_IgG4 Antibodies from Transfected Cells.

Anti-ADAMTS-5 antibodies were produced from transfected cells. CHO-S cells were transfected with plasmids encoding CRB0016 and CRB0017 heavy and light chains. Conditioned media from transfected cells were recovered by removing cells and debris. Clarified conditioned media were loaded onto protein A-sepharose column. Non-specific bindings were removed by extensively binding buffer washes (20 mM sodium phosphate pH 7.0). Bound antibody proteins on the protein A column were recovered by acidic antibody elution from protein A (0.1 M glycine-HCl pH 3.0). Eluted proteins were immediately neutralized with 1M Tris-HCl pH=9.0 (100 μL per mL eluted fractions). Pooled eluted fractions were dialyzed against PBS. Aggregated antibody proteins were removed by size exclusion chromatography.

Purification of Recombinant Spacer-ADAMTS-5-GST Protein.

Thawed Sp_ADAMTS-5-GST induced and expressing bacteria was resuspended in 20 mL of Lysis Buffer (PBS, 10 μg/mL DNase, 20 μg/mL Lysozyme). Resuspended pellets were incubated for 45 minutes at 4° C. with rocking After incubation lysed bacteria were sonicated in ice for 3 times (15 seconds each). After 10 minutes centrifugation at 6000 RPM at 4° C. the supernatant was collected, filtered with 0.2 □ micron filter and processed for purification. GST Trap column (GE) was connected with AKTA Purifier (GE) and washed with 5CV of water at 5 mL/min flux. Then column was washed with 5CV of PBS at 5 mL/min flux. Column was then connected to a peristaltic pump and loaded at 1 mL/min flux with filtered supernatant. After washing with 5CV of PBS at 5 mL/min flux the column was reconnected to AKTA purifier and washed again with 2CV of PBS at 5 mL/min flux. Protein was eluted at 100% elution buffer (PBS, 10 mM Glutathione). Fractions of the peak were collected into 2 mL eppendorf tubes. Pool of 3 main central fractions diluted in PBS was concentrated using Amicon Ultra 15 according to manufacturer's specifications. Concentrated protein was quantified with Protein 80 BioAnalyser (Agilent). Aliquots were stored at −80° C.

Expression and Refolding of Anti-Sp_ADAMTS-5scFvs in the Cytoplasm of E. coli.

Anti-Sp_ADAMTS-5 scFv fragments (SEQ, ID 125, 126, 127, 128, 129, 130, 131, 132, 135, 136, 137) were subcloned into NcoI/NotI restriction sites of pETM-13 bacterial expression vector. E. coli BL21DE3 harbouring the expression plasmid was cultured in 500 mL of 2YT/Kan medium until the mid-exponential phase (OD600=0.75) and then induced with IPTG (1.5 mM) for additional 5-6 h at 37° C. with shaking (180 rpm). The cells were harvested at 6000 rpm (Beckman) and the pellets were used for inclusion bodies (IB) preparation. A large-scale expression method as inclusion bodies of E. coli was optimized, using in vitro refolding (Patil et al., 2008. J Biotechnol. 134:218-221. Epub 208 January 2018); (Umetsu et al., 2003. J Biol Chem. 278:8979-8987. Epub 203 January 8977). Pellet was resuspended at 5 mL/g−1 with IBR buffer (50 mM Tris/HCl, 0.5 mM EDTA, 20 μg/mL lysozime, 10 μg/mL DNase at pH 8) and put on shaking plate for 1 h at RT. Sample was sonicated for 45 sec on ice for three pulses, followed by 1 min incubation on ice. The lysate was then centrifuged for 10 min at 4° C. at 6,000 rpm. The pellet was resuspended in 20 mL of wash buffer 1 (10 mM Tris pH 8, 1 mM EDTA, 1% Triton X-100), vortexed and then the inclusion bodies were sedimented by centrifugation at 10,000 rpm for 10 min at 4° C. Pellet was washed with 20 mL wash buffer 2 (10 mM Tris pH8, 1 mM EDTA, 1M NaCl), vortexed and then centrifugated at 10,000 rpm for 10 min at 4° C. Finally pellet was washed with 20 mL wash buffer 3 (10 mM Tris pH8, 1 mM EDTA), vortexed and centrifugated at 10,000 rpm for 10 min at 4° C. The IB preparation was solubilised at 5 mLg−1 with solubilization buffer (100 mM Tris/HCl; 6M guanidine HCl; 1 mM EDTA; 100 mM DTT at pH 8). The solubilised proteins were incubated for 2 h at room temperature under vigorous agitation. After lowering the pH of the protein solution at pH 4 with HCl 1M, the insoluble material was removed by centrifugation at 10,000 rpm for 10 min. In order to remove DTT from the solute a triple dialysis against IBD buffer (6M guanidine HCl at pH 4) was performed. The solubilised and quantified proteins were diluted 35 mg/L, as quickly as possible, into cold REF buffer (100 mM Tris/HCl; 0.5M arginine; 375 μM oxidized 1-gluthatione; 5 mM EDTA at pH 8.5). The protein solution was dispensed every 50 minutes with a pipette directly into the REF buffer while vortexing. After 16 h of the last addition the sample was first concentrated and the remaining guanidinium was removed by dialysis into IEXA buffer (according to pI of scFv and thus to ionic exchange protocol subsequently employed). The refolded scFvs were purified by a ion exchange chromatography stored aliquoted at −80° C.

Specificity ELISA: Anti-Sp_ADAMTS-5 scFvs Versus Sp_ADAMTS-5-GST.

Nunc Maxi-Sorp Immunoplate was coated with 100 mL Sp_ADAMTS-5-GST and GST at 10 μg/mL in coating buffer (100 mM Na$_2$CO$_3$ pH 9.6). Plate was incubated overnight at 4° C. next day, the unbound antigens were discarded and plate was washed 3× with PBS. Non-specific binding was blocked by adding 200 mL of 3% MPBS (3% fat free milk in PBS). Plate was incubated for 1 h at RT. Plate was washed 3×TPBS (0.1% Tween20 in PBS) and 3×PBS. 100 μL of serial dilution of anti-Sp_ADAMTS-5scFv (0.5-50 μg/mL) in 3% MPBS was added to appropriate wells. Then plate was incubated for 2 h at RT. After washing with 3×TPBS and 3×PBS, 100 μL of anti-V5 antibody (Invitrogen) diluted 1:5000 in 3% MPBS was added to each well. Plate was incubated for 1 h and 30 min at RT. After washing with 3×TPBS and 3×PBS 100 μL of anti-mouse HRP (DAKO) diluted 1:2000 in 3% MPBS was added to each well. Plate was incubated for 1 h at RT. After washing with 3×TPBS and 3×PBS 80 μL of TMB (Sigma) was added. Plate was incubated in dark chamber until samples reach the desired signal. 80 μL of stopping solution (500 mM H$_2$SO$_4$) was added to each well before reading. Data were collected measuring OD(450 nm) by LD 400 Luminescence Detector (Beckman Coulter).

Sandwich ELISA: Anti-Sp_ADAMTS-5 mAb Versus Sp_ADAMTS-5-GST.

Nunc Maxi-Sorp Immunoplate was coated with serial dilution of 100 mL of anti-Sp_ADAMTS-5 immunoglobulin in coating buffer (100 mM Na$_2$CO$_3$ pH 9.6). Plate was incubated overnight at 4° C. The next day, the unbound antibodies were discarded and plate was washed 3× with PBS. Non-specific binding was blocked by adding 2004 of 3% MPBS (3% fat free milk in PBS). Plate was incubated for 1 h at RT. Plate was washed 3×TPBS (0.1% Tween20 in PBS) and 3×PBS. 100 μL of Sp_ADAMTS-5-GST and GST (30 μg/mL) in 3% MPBS was added to appropriate wells. Then plate was incubated for 2 h at RT. After washing with 3×TPBS and 3×PBS, 100 μL of anti-GST antibody (Sigma) diluted 1:1000 in 3% MPBS was added to each well. Plate was incubated for 1 h and 30 min at RT. After washing with 3×TPBS and 3×PBS 100 μL of anti-rabbit HRP (DAKO) diluted 1:2000 in 3% MPBS was added to each well. Plate was incubated for 1 h at RT. After washing with 3×TPBS and 3×PBS 80 μL of TMB (Sigma Aldrich) was added. Plate was incubated in dark chamber until samples reach the desired signal. 80 μL of stopping solution (500 mM H$_2$SO$_4$) was added to each well before reading. Data were collected measuring OD(450 nm) by LD 400 Luminescence Detector (Beckman Coulter).

Evaluation of Anti-Sp_ADAMTS-5scFv and/or mAb Affinity and Kinetic Constants by Surface Plasmon Resonance Measurements.

Binding kinetics of Sp_ADAMTS-5-GST binding to anti-Sp_ADAMTS-5 antibody (scFv or IgG) immobilized by amine coupling in a carboxymethyl dextran matrix of a CM5 chip. Standard immobilization procedures were used (Schuck, 1997 Annu Rev Biophys Biomol Struct. 26:541-566). 20-50 µg/mL of scFv or IgG was dissolved in acetate buffer (suitable pre-concentration buffer at least 2 pH unit below the pI of the immunoglobulin in order to get a net positive charge). Immobilization level of 5000 RU for the immunoglobulin and 1000 RU for scFv was set to get a low density immobilization of the ligand. Mild regeneration condition of the chip (contact time of 30 seconds at 10 mM glycine pH2) was used.

Sp_ADAMTS-5-GST was diluted into PBS+0.005% Tween20 running buffer at 5 serial dilution (starting in the micromolar range and diluting 1:2) and applied at a flow rate of 30 µl/min. Sample condition Step was set initially with contact time of 60 seconds and dissociation time of 400 seconds. On the basis of the resulting sensograms, in the kinetic/affinity step, the analyte concentrations, contact time, dissociation time and regeneration solution were adjusted.

Data were analysed by Bioevaluation Software: the quality of the data fitting can be checked by the value of $Chi^2$ and of the U-value.

Evaluation of Binding Capacity of Anti-spacer ADAMTS-5 mAbs to ADAMTS-5 Target Antigen.

mAbs anti-spacer CRB0017_IgG4, CRB0093 IgG4, CRB0094 IgG4, CRB0123IgG4 and CRB0124_IgG4 were coated at 2 µg/mL in 100 mM $Na_2CO_3$ pH 9.6 and incubated at 4° C. overnight. Next day the unbound immunoglobulin was discarded off the plate and wash 3× with TBS. Plate was blocked by adding 200 µl of protein free blocking buffer (Pierce-undiluted) and incubated for 1 hour at 37° C. Plate was washed as above. Then 100 µL per well of purified ADAMTS-5 (4 µg/ml) in Blocking buffer (dil. 1:2 in TBS) and as negative control, 100 µl per well of Blocking buffer dil. 1:2 in TBS were added. Plate was incubated for 1 hour at 37° C. Plate was subsequently washed 3× with TTBS. 100 µl per well of Mouse Anti-Flag Antibody (Sigma; cod F3165) dil 1:8000 was added in blocking buffer (dil. 1:2 with TTBS). Plate was incubated for 1 hour at 37° C. Plate was washed Wash 3× with TTBS. 100 µl of anti-mouse antibody (DAKO) diluted 1:2000 in TTBS was added and plate was incubated for 1 hour at 37° C. Plate was finally washed 3× with TTBS and 3× with TBS. For detection 100 µl of TMB was added and incubated in the dark till the signal is visible (normally 5-15 min). 100 µL per well of Stopping solution was added to stop reaction and to proceed to O.D. measurement.

Cloning and Expression of ADAMTS-4 and ADAMTS-5 3×FLAG Full Length Forms.

cDNA encoding human ADAMTS-5 (SEQ. ID NO: 133) and human ADAMTS-4 (SEQ. ID NO: 134) sequences were amplified to introduce restriction site for Kpn I (5' termini) and for Xho I (3' termini) and to remove the region coding for propeptide. After digestion with KpnI and XhoI, the inserts were subcloned into pSecTag2A vector (Invitrogen).

ADAMTS-5 3×FLAG/pSecTag2A and ADAMTS-4 3×FLAG/pSecTag2A were transfected in FreeStyle™ 293-F cell line. Cells were adapted to suspension culture in FreeStyle™ 293 Expression Medium. Anti-clumping agent (Invitrogen) was added to the medium, before or post-transfection. Cells were transfected with FreeStyle™ MAX Reagent complex in animal-origin free OptiMEM™ SFM. Transfected cells were incubated at 37° C., 8% CO2 on a stirring platform set at 75 rpm. 100 µg/ml heparin was added into the culture 24 hour post-transfection. ADAMTS-5 3×FLAG and ADAMTS-4 3×FLAG expressions reached a significant protein activity 48-72 hours post-transfection. After 2-3 days, supernatants were harvested and stored at −80° C. until purification.

Full Length ADAMTS-4/ADAMTS-5 3×FLAG Protein Purification.

300 ml of ADAMTS-5 3×FLAG/ADAMTS-4 3×FLAG supernatants were loaded into 1 mL anti-FLAG M2 Affinity Gel (Sigma-Aldrich). Samples were applied at flow rate of 1 mL/min with pressure of 0.5 MPa and the columns were washed with 10 volumes of 50 mMTris-HCl (pH 7.4), 10 mM CaCl2, 10 µM ZnCl, 0.02% Brij-35 containing 1 M NaCl in order to remove heparin bound to the enzyme. Elution of FLAG fusion proteins was achieved by competition with 200 µg/ml of 3×FLAG peptide (Sigma-Aldrich) in aggrecanase reaction buffer (50 mM Tris-HCl (pH 7.4), 150 mM NaCl, 10 mM CaCl2, 10 µM ZnCl, 0.02% Brij-35). A flow rate of 1 mL/min was maintained throughout the purification procedure and fractions of 1.0 ml were collected. The fractions containing the eluted proteins were pulled together and concentrated 5× using a Vivaspin concentrator (Sartorius) (30 kD of cut-off).

Western Blot Analysis of ADAMTS-4/ADAMTS-5 3×FLAG Purified Proteins.

Figure 1:
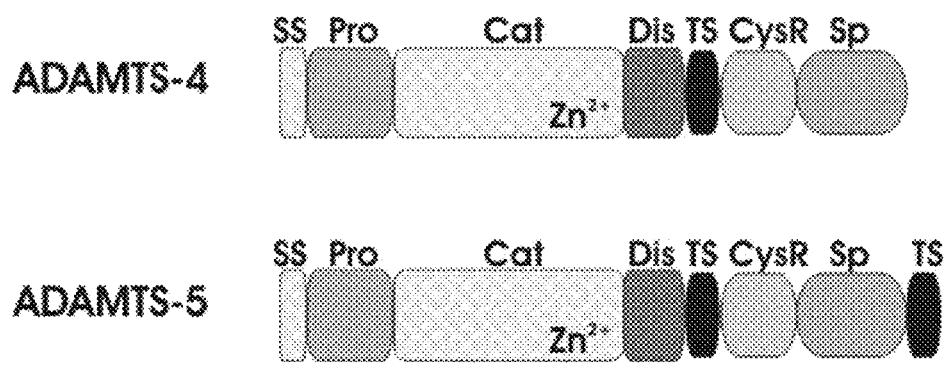
FIG. 1. ADAMTS-4 and ADAMTS-5 schematic representation. Both enzymes are multidomain metalloproteinases secreted from the cell into the extracellular space. Both enzymes have a similar domain arrangement consisting of a signal sequence (SS), a prodomain (Pro), a catalytic metalloproteinase domain (Cat), a disintegrin (Dis) domain, a thrombospondin type I (TS) domain, a cysteine-rich (CysR) domain, and a spacer (Sp) domain. In addition, ADAMTS-5 contains an extra TS domain after the spacer domain.
Figure 2:
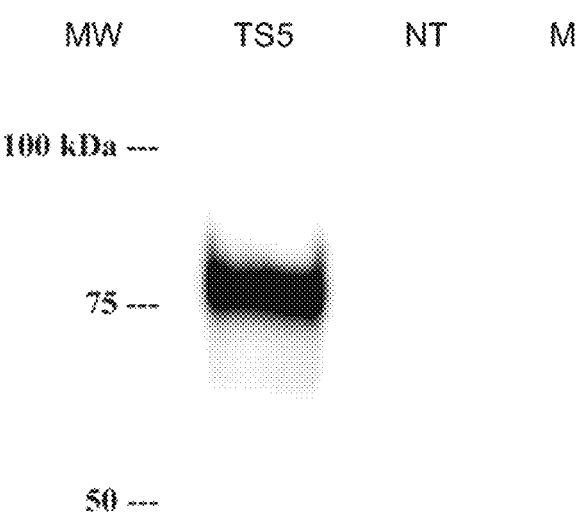
FIG. 2. Western blot analysis of ADAMTS-5 p75 after FPLC purification, using an antibody against the FLAG tag of the protein. Western blots were probed with monoclonal antibody recognizing the fusion proteins containing a FLAG peptide sequence (Sigma Aldrich, Monoclonal ANTI-FLAG M2, dilution 1:1000). For detection using chemiluminescent peroxidase substrate, an anti-mouse IgG-peroxidase (1:10, 000) was employed. TS5=ADAMTS-5 Transfected cells; NT=Non Transfected cells; M=Mock.

ADAMTS-5 3×FLAG and ADAMTS-5 3×FLAG purified samples, were resuspended in Sample buffer (Invitrogen), heated for 10 min and loaded onto a 10% SDS-polyacrylamide gel electrophoresis system (Invitrogen, NuPage System) and then subjected to Western blotting. The separated proteins were transferred to PVDF membrane (GE Healthcare). The membranes were blocked 30' with Starting Block Solution (Pierce) and incubated 1 h with primary monoclonal antibody anti 3×FLAG (Sigma) 1:1000 at ° RT. After incubation at ° RT (1 h) with peroxidase-coupled secondary antibody anti mouse (AbCam), diluted 1:10.000, protein bands were detected by using Super Signal Dura West (Pierce). Images were acquired with a CCD camera using a Las3000 Imaging System (Fuji) (see FIG. 2 for ADAMTS-5 western blot).

Analysis of Enzymatic Activity.

The purified full length enzymes ADAMTS-4 3×FLAG and ADAMTS-5 3×FLAG were tested for activity by an enzymatic assay. Aggrecan purified from bovine nasal cartilage entrapped in polyacrylamide (Nagase and Woessner, 1980. *Anal Biochem.* 107:385-392) was used as a substrate to determine aggrecan-degrading activity.

Aggrecan/polyacrylamide particles samples (5.0±0.2 mg dry weight) were placed in 1.5 mL tubes with 400 µL of TNC (0.1 M Tris-HCl, 0.1 M NaCl, 10 mM CaCl2, 0.1% CHAPS; pH 7.5) and 100 µL of recombinant ADAMTS-4 (p68, FL) and ADAMTS-5 (p75, FL) preparations, expressed in transiently transfected FreeStyle-293 cells and incubated at 37° C. for 6 or 24 h. The reactions were stopped with 500 µL of stop solution (50 Mm Tris, 200 mM Sodium acetate, 100 mM EDTA; pH=6.8) and the particles were separated from the liquid phase by centrifugation (10000 rpm, 4 min, 4° C.). The amount of sulphated glycosaminoglycans (GAGs) in the supernatant was determined by a colorimetric assay (1.9 dimethyl methylene blue, DMB). Standard curve (Chondroitin Sulphate extracted from bovine trachea) and samples were diluted in PBS-BSA 1%. After a 5-20 min of reaction, samples were read at 590 nm. The GAGs concentration of each sample was calculated from absorbance measurements (blank subtracted) and compared to the reference standard curve.

Cartilage Explant and Culture.

Bovine nasal cartilage disks were obtained from eight month male bovine nasal septum. In brief, 2-mm-diameter punches of cartilage were obtained from the nasal cartilage. The punches were first washed three times with PBS-AASS buffer (1×PBS, 100 U/ml penicillin G, 100 µg/ml streptomycin and 2.5 µg/ml amphotericin B). The punches were subsequently incubated at 37° C. in an atmosphere of 5% CO2, in microplate wells containing DMEM 10%, 100 U/ml penicillin G, 100 µg/ml streptomycin and 2.5 µg/ml amphotericin B (DMEM-AASS media). After three hours the samples were washed with PBS-AASS buffer and incubated with DMEM-AASS media. 48 h after the preparation of the cartilage cells, samples were treated with 5 ng/mL IL-1α plus different concentration of the inhibitor (i.e. CRB0017_IgG4 and TIMP-3) and incubated in DMEM, 0.1% BSA+AASS for 48 h. After treatments supernatants and small pieces of cartilage were collected and used for GAG analysis (the measurement of GAG release is the quantitation of glycosaminoglycans—GAGs—in the form of aggrecan fragments released from the cartilage in culture). The punches of cartilages were first incubated with 500 µg/mL papain at 65° C. for 2 h for the measurement of the percentage of total GAG remaining in the tissue. The sulphated glycosaminoglicans (GAGs) determination is done by a colorimetric assay with 1,9 dimethylmethylene blue (DMB). Standard curve (Chondroitin Sulphate extracted from bovine trachea), medium samples and and digested cartilage samples were diluted in PBS-BSA 1%. After a 5-20 min of reaction samples were read at 590 nm.
Immunoprecipitation of ADAMTS-5 and ADAMTS-4 3×FLAG Full Length Proteins.

Immunoprecipitation was performed using Protein G Immunoprecipitation Kit (SIGMA). To reduce background caused by non-specific adsorption of irrelevant cellular proteins to the Protein G Agarose, a pre-clearing step was performed. 50 µl of the Protein G Agarose suspension was added to the sample (ADAMTS-5 or ADAMTS-4 purified proteins) in a microcentrifuge tube and incubate for 2 hours at 4° C. with rocking Beads was pelleted by centrifugation at 12,000 g for 30 seconds in a microcentrifuge and the collected supernatant (precleared sample) was transferred to a fresh tube. This sample was used for immunoprecipitation. Add to the sample the anti-Sp_ADAMTS-5 and adjusted the volume to 600 µL in IP buffer. This sample was added to a capped spin column and incubated overnight at 4° C. The day after, 50 µL of washed Protein G Agarose beads was added to the column. After 2 h of rocking incubation at 4° C. the tip of the spin column was broken off and the column was placed into 2 mL eppendorf tube. The tube was spinned at 12,000×g for 30 seconds at 4° C. The beads in the spin column were resuspended in 700 µl of 1×IP buffer and then column was centrifuged at 12,000×g for 30 seconds at 4° C. This washing step was repeated for 3 times. The last wash was performed with 0.1×IP buffer. Beads were resuspended with 50 µL of hot 1× Laemmli Sample Buffer. After 10 minutes incubation at 95° C., proteins were eluted by centrifugation at 13,000×g for 1 minute. The sample was loaded onto SDS-PAGE gel for western blot analysis.
Binding of Present Invention Antibodies on Hek-293-ADAMTS-5-3×FLAG/Hek-293 in Cell-ELISA Format.

The Cell-Based ELISA format allows target cellular proteins, to be analyzed in the same well, thus minimizing well-to-well variability. FreeStyle™ 293-F cell line stably expressing ADAMTS-5 3×FLAG were used. Cells were coltured as suspension culture in FreeStyle™ 293 Expression Medium. FreeStyle™ 293-F cells expressing ADAMTS-5 3×FLAG and FreeStyle™ 293-F cells were seeded in 96-well plates (100.000 cells/well) and incubated for 1 h at at 37° C. Cells were then treated with CRB0017_IgG4 (final concentration 10-5-2 µg/ml) and incubated for 1 h at at 37° C. Cells were then fixed with 4% p-formaldehyde (50 µL/well) in HBSS (with Ca/Mg) for 15 min at RT and permeabilized or not in the wells with 100 µl of 0.1% Igepal in TBS (100 µL/well) for 15 min at RT. Cells were then washed with TBS (100 µL/well) followed by quenching with 1% $H_2O_2$ in TBS (100 µL/well) for 20 min RT. Cells were subsequently washed with TBS (100 µL/well) followed by blocking with 5% BSA in TBS (100 µL/well) for 30 min RT. After washing cells 3× with Tween 0.1% in TBS (TTBS)-(100 µL/well) cells were then incubated with secondary antibody (100 µL/well donkey anti-human-HRP Antibody 1:5000 in TTBS) for 30 min at RT. After washing cells 3× with TTBS (200 4/well) cells were detected adding TMB 1004/well. Reaction was stopped detection with 0.5 M $H_2SO_4$ (100 µL/well) within 15 minutes. pAb Anti-ADAMTS-5 Cys 636-649 (Abcam#ab111918) and pAb Anti-ADAMTS-5 Cys 600-700 (Abcam # ab41037) were used to detect the effective retention and/or secretion of ADAMTS-5.
Evaluation of Binding Capacity of Present Invention Antibodies to ADAMTS-5.

mAb CRB0017_IgG4 was coated at 2 µg/mL in 100 mM $Na_2CO_3$ pH 9.6 and incubated at 4° C. overnight. Next day the unbound immunoglobulin was discarded off the plate and wash 3× with TBS. Plate was blocked by adding 200 µL of protein free blocking buffer (Pierce-undiluted) and incubated for 1 hour at 37° C. Plate was washed as above. Then 100 µL per well of either HEK-293-ADAMTS-5-3×FLAG or HEK-293 (negative control) conditioned medium supplemented with Heparin 100 µg/ml was added. Plate was incubated for 1 hour at 37° C. Plate was subsequently washed 3× with TTBS. 100 µl per well of Mouse Anti-Flag Antibody (Sigma; cod F3165) dil 1:8000 was added in blocking buffer (dil. 1:2 with TTBS). Plate was incubated for 1 hour at 37° C. Plate was washed Wash 3× with TTBS. 100 µl of anti-mouse antibody (DAKO) diluted 1:2000 in TTBS was added and plate was incubated for 1 hour at 37° C. Plate was finally washed 3× with TTBS and 3× with TBS. For detection 100 of TMB was added and incubated in the dark till the signal is visible (normally 5-15 min). 100 µL per well of Stopping solution was added to stop reaction and to proceed to O.D. measurement.
Evaluation of the Capacity of Syndecan-4 to Interfere in CRB0017_$IgG_4$ Anti-spacer ADAMTS-5 Binding to ADAMTS-5 Antigen.

100 µl per well of CRB0017_IgG4 (2 µg/ml) was coated in immunoplate in coating buffer (2 µg/ml) and incubated at 4° C. overnight. The unbound immunoglobulin was discarded off the plate and wash 3× with TBS. Non-specific binding was blocked by adding 200 µl per well of Blocking buffer (undiluted) and incubated for 1 hour at 37° C. In the meantime tubes were prepared with [ADAMTS-5 (4 µg/ml)+Syndecan-4 (R&D System#2918-SD-050) in Blocking buffer dil. 1:2 in TBS; range of concentrations tested for Syndecan-4: 0.05-2 µg/ml; in the conditions set up for this assay, the maximum interference effect has been obtained with 0.1 µg/ml. Plate was then washed as above. 100 µl per well of either ADAMTS-5 (4 µg/ml) or [ADAMTS-5 (4 µg/ml)+Syndecan-4 (0.1 µg/ml) in Blocking buffer dil. 1:2 in TBS were added. As negative control, to some well were added 100 µl of Blocking buffer dil. 1:2 in TBS. Some wells were added with 100 µl of Syndecan-4 (at appropriate concentration) as a control. Plate was incubated for 1 hour at 37° C. After incubation plate was washed 3× with TTBS. 100 µl per well of anti-Flag antibody (Sigma) diluted 1:2000 in Blocking buffer (dil. 1:2 with TTBS) was added. In wells with just Syndecan-4, 100 μl per well of Anti-Syndecan-4 (Santa Cruz Biotechnology # sc-12766) diluted 1:5000 in Blocking buffer (dil. 1:2 with TTBS) was added. Plate was then incubated for 1 hour at 37° C. After incubation plate was washed 3× with TTBS. 100 μl per well of peroxidase-conjugated anti-mouse antibody (Jackson ImmunoResearch) diluted 1:5000 in TTBS were added and plate was incubated for 1 hour at 37° C. Plate was finally washed 3× with TTBS and 3× with TBS and 100 μl per well of TMB was added. Plate was incubated in the dark till the signal was visible (normally 5-15 min; in any case not more than 30 min). 100 μl per well of Stopping solution was added to proceed to O.D. measurement Evaluation of the Effect of Anti-ADAMTS-5 mAbs in the STR/Ort Mouse Model of Osteoarthritis.

STR/ort male mice (Mason et al., 2001. *Osteoarthritis Cartilage*. 9:85-91) were recruited at 5 months of age (n=20-22), randomized for treatment in each cage, with 4 animals per cage, weighed and treated intraarticularly in each knee with either anti-ADAMTS-5 IgG4 1.2 μg, anti-ADAMTS-5 IgG4 12 μg, or vehicle. After 6 weeks the intraarticular administration of anti-ADAMTS-5 IgG4 was repeated with the same doses. After 3 months from recruitment the animals were sacrificed by cervical dislocation and hind limbs explanted and fixed in formalin o/n. Hind limbs were embedded in paraffin, 5-micron thick sections were produced and stained with toluidine blue and then scored in a blind fashion according to both Mankin's (Mankin et al., 1971. *J Bone Joint Surg Am*. 53:523-537) and the OARSI methods (Pritzker et al., 2006. *Osteoarthritis Cartilage*. 14:13-29). This method produces an OA score with a range 0-24 based on the most advanced grade (6) and the more extending stage (4). Statistical analysis was performed with Student's t test comparing vehicle vs. basal, and with ANOVA followed by Dunn's or Dunnett's tests comparing all treatment groups vs. vehicle.

Evaluation of Present Invention Antibodies in the Medial Meniscal Tear (MMT) Rat Model of Osteoarthritis.

Unilateral medial meniscal tear (MMT) in rats results in rapidly progressive cartilage degenerative changes characterized by chondrocyte and proteoglycan loss, fibrillation, osteophyte formation and chondrocyte cloning. Progressive degenerative changes occur 3-6 weeks post-surgery: tibial cartilage degeneration may be focally severe with degenerative changes of lesser severity in the surrounding matrix and prominent osteophytes.

Male Lewis rats weighing 200 g were used. Right knees underwent surgery or sham-surgery. The medial collateral ligament was transected and the medial meniscus was grasped with a hemostat and reflected proximally toward the femur. The meniscus was transected with a scalpel or small surgical scissors. Sham operation consisted in only opening skin and capsula. One week after surgery rats were treated intraarticularly in the operated knee with present invention antibodies such as either CRB0017_IgG4 34 μg, CRB0017_IgG4 72 μg, or vehicle. Four weeks after surgery the animals were sacrificed by cervical dislocation and the operated knees explanted and fixed in formalin o/n. and embedded in paraffin; 5-micron thick sections were produced and stained with toluidine blue and then scored in a blind fashion according to both Mankin's and the OARSI methods. Statistical analysis was performed with Student's t test comparing vehicle vs. sham, and with ANOVA.

Results

Selection of Specific Anti-Spacer Domain Antibodies Using SPLINT Technology.

To select specific anti-spacer domain of ADAMTS-5 by SPLINT technology, the spacer domain of ADAMTS-5 (aa 732 to aa 874 of SEQ. ID NO. 2) was cloned to the 3' of LexA (LexA-Sp_ADAMTS-5; SEQ. ID NO: 93) and used to challenge a mouse SPLINT (mSPLINT) and two-different human SPLINT (huSPLINT 09 and huSPLINT 10) libraries (Visintin et al., 2004. *J Immunol Methods*. 290:135-153). From the selection procedure a total of 325 colonies able to grow in the absence of histidine and showing activation of f3-Galactosidase were obtained. The scFv-VP16 plasmids were isolated and sorted by their restriction patterns and sequences. The specificity of scFvs with different DNA fingerprints were re-analyzed using yeast strains expressing LexA-Sp_ADAMTS-5 and LexA-lamin, as non relevant antigen. 11 different anti-Spacer domain scFvs were thus identified. Analysis of the V region nucleotide sequences of the selected anti-Spacer scFv revealed that they were derived from germline V region genes (Table IV) with very few somatic mutations (data not shown).

TABLE IV

Analysis of the V region nucleotide sequences of the selected anti-Spacer scFv

| CLONE | CRB | SEQ. ID | VH-gene/J-gene and allele identification | VL-gene/J-gene and allele identification |
|---|---|---|---|---|
| M6 | CRB0017 | 3; 4 | Musmus IGHV1-7*01 F; Musmus IGHJ2*01 F | Musmus IGKV2-112*01 F; Musmus IGKJ2*01 F |
| 7A | CRB0018 | 5; 6 | Musmus IGHV4-1*02 F; Musmus IGHJ1*01 F | Musmus IGKV3-10*01 F; Musmus IGKJ5*01 F |
| 14 | CRB0019 | 7; 8 | Musmus IGHV14-3*02 F; Musmus IGHJ4*01 F | Musmus IGKV6-23*01 F; Musmus IGKJ2*01 F |
| 7A | CRB0091 | 9; 10 | Homsap IGHV4-34*01 F; Homsap IGHJ4*02 F | Homsap IGKV1-17*01 F; Homsap IGKJ2*01 F |
| C21 | CRB0092 | 11; 12 | Homsap IGHV3-13*01 F; Homsap IGHJ6*02 F | Homsap IGLV1-40*02 F; Homsap IGLJ7*01 F |
| 47A | CRB0093 | 13; 14 | Homsap IGHV3-72*01 F; Homsap IGHJ3*01 F | Homsap IGKV1-39*01 F; Homsap IGKJ2*01 F |
| 48B | CRB0094 | 15: 16 | Homsap IGHV4-34*01 F; Homsap IGHJ5*02 F | Homsap IGLV2-14*01 F; Homsap IGLJ3*02 F |
| 15A | CRB0102 | 17; 18 | Homsap IGHV1-24*01 F; Homsap IGHJ4*02 F | Homsap IGKV5-2*01 F; Homsap IGKJ4*01 F |
| S39 | CRB0122 | 19; 20 | Homsap IGHV3-23*01 F; Homsap IGHJ3*02 F | Homsap IGLV9-49*01 F; Homsap IGLJ1*01 F |
| S50 | CRB0123 | 21; 22 | Homsap IGHV3-30*03 F; Homsap IGHJ6*02 F | Homsap IGKV1D-17*02 [F]; Homsap IGKJ1*01 F |

TABLE IV-continued

Analysis of the V region nucleotide sequences of the selected anti-Spacer scFv

| CLONE | CRB | SEQ. ID | VH-gene/J-gene and allele identification | VL-gene/J-gene and allele identification |
|---|---|---|---|---|
| S53a | CRB0124 | 23; 24 | Homsap IGHV1-24*01 F; Homsap IGHJ4*02 F | Homsap IGLV3-1*01 F; Homsap IGLJ2*01 F |

The amino acid sequences of V regions of the isolated anti-Sp_ADAMTS-5scFvs are in the group of sequences consisting of SEQ.ID NO: 3 and 4; 5 and 6; 7 and 8; 9 and 10; 11 and 12; 13 and 14; 15 and 16; 17 and 18; 19 and 20; 21 and 22; 23 and 24.

Expression and Refolding of Anti-Spacer scFv in the Cytoplasm of E. coli.

To identify potential anti-spacer in vivo binders, cDNAs expressing anti-Sp_ADAMTS-5 scFv were cloned into E. coli pET41b expression vector. The proteins were well expressed in the cytoplasm and mostly retained in inclusion bodies (IB). scFv fragments can be refolded by dialysis after solubilization of IB (Umetsu et al., 2003. J Biol Chem. 278:8979-8987. Epub 203 January 8977). The authors performed the technique of refolding by dilution (Patil et al., 2008. J Biotechnol. 134:218-221. Epub 208 January 2018). The refolding condition of scFv was optimized for each sample. Refolded scFv were subsequently quantified by Bioanalyzer 2100 (Agilent) and tested by ELISA and Biacore analysis.

Binding Specificity of Anti-ADAMTS-5 to Human ADAMTS-5.

Figure 3:
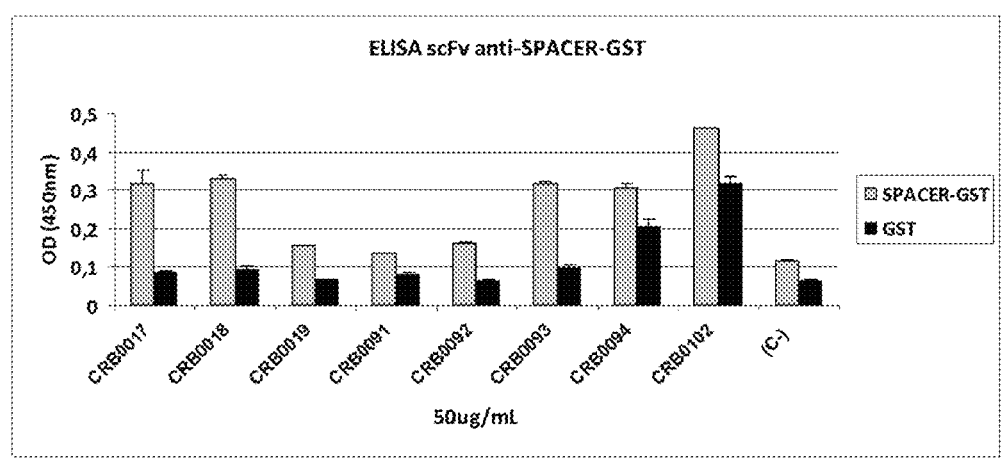
FIG. 3. ELISA reactivity of isolated anti-Sp_ADAMTS-5 scFvs with Spacer-GST and GST negative control. Spacer-GST and GST antigens were coated at 10 µg/mL. Anti-Sp_ADAMTS-5scFvs were used at 50 and/or 5 µg/mL (data not shown). The mean absorbance at 450 nm of the experiments performed in duplicate wells is shown with SD indicated by the bars.

To understand the specificity of the panel of anti-Sp_ADAMTS-5scFvs isolated from SPLINT libraries, the immunoreactivity for Spacer-GST (SEQ. ID NO: 94) and ADAMTS-5 FL of these antibodies was demonstrated. All the isolated anti-Spacer scFvs were reactive with the GST fusion protein of the truncated form of ADAMTS-5 in ELISA assay. However the CRB0017, CRB0018 and CRB0093 scFvs were highly specific and only weak binding was observed to GST protein used as negative control (FIG. 3).

Figure 4:
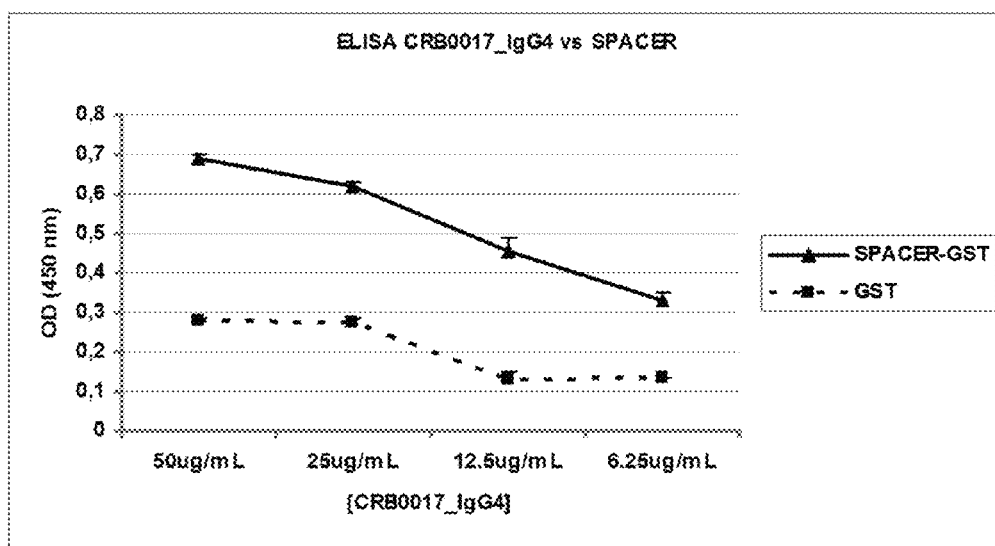
FIG. 4. Sandwich ELISA. Dilution curves of coated CRB0017_IgG4 binding to Spacer-GST and/or GST in solution at 30 µg/mL. As secondary antibody an anti-GST (1:1000) was used following an anti-rabbit IgG HRP (1:2000) for final detection. The mean absorbance at 450 nm of the experiments performed in duplicate wells is shown with SD indicated by the bars.
Figure 5:
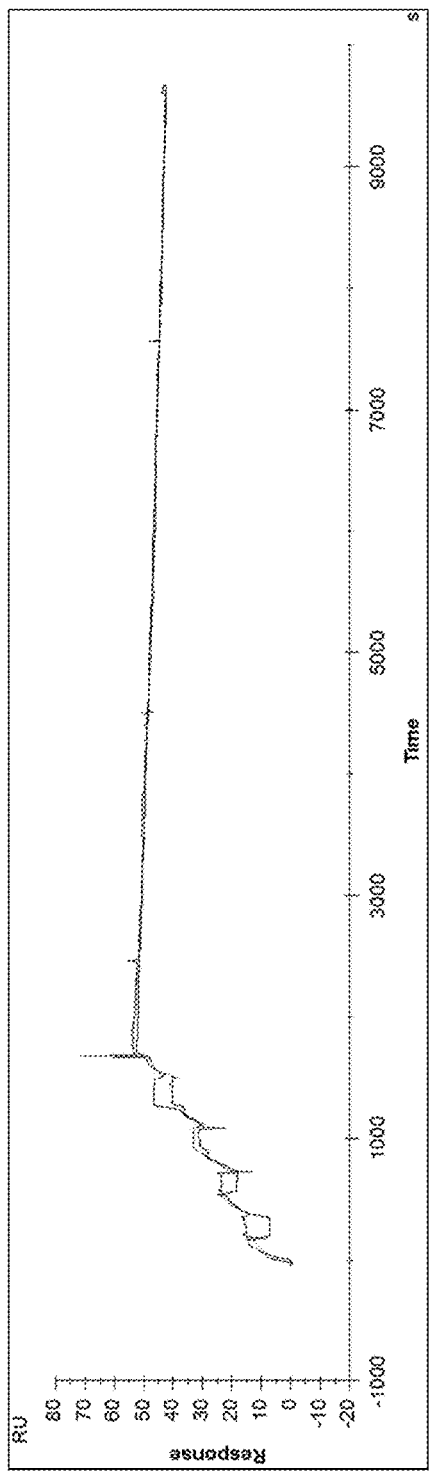
FIG. 5. Kinetic analysis of CRB0017_IgG4 binding Spacer-GST in solution using Biacore X-100. 5610 RU of CRB0017_IgG4 were immobilized on CM5 chip. The association and dissociation were performed for 180 s and 800 s respectively. Kinetic rate constants and affinity determined for CRB0017_IgG4/Spacer-GST interaction are shown in the table below.
Figure 6:
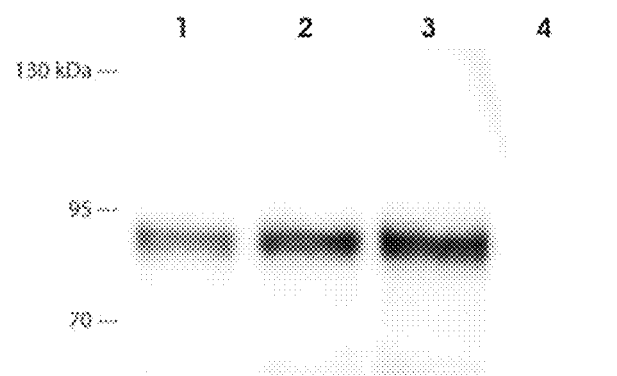
FIG. 6. Immunoprecipitation (IP) of ADAMTS-5 full length (TS5-FL) by CRB0017_IgG4. 0.1 µg of dialyzed/affinity purified TS5-FL were immunoprecipitated (IP) with anti-Sp_ADAMTS-5 CRB0017_IgG4 antibody (11, 22 and 25 µg in lane 1, 2 and 3, respectively) or with 11 µg of unrelated antibody as a negative control (lane 4). Immunoprecipitates were analysed by immunoblotting with anti-FLAG antibody (1:1000). CRB0017_IgG4-immunoprecipitated ~81 kDa TS5-FL band was observed corresponding to TS5-FL p75 protein. The molecular mass of immunoprecipitated TS5-FL protein is slightly higher than predicted from its amino acid composition. This difference is due to N-glycosylation in the Dis, CysR, Sp domains and to O-glycosylation at the C-term domain. Molecular mass markers are indicated to the left-hand side of the Figure.
Figure 7:
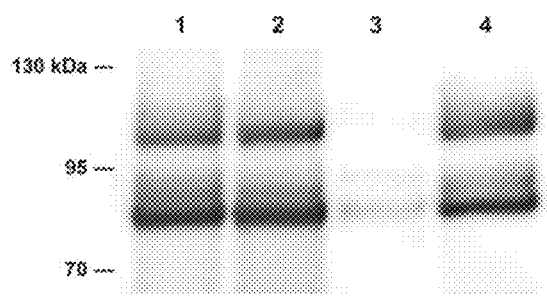
FIG. 7. IP of ADAMTS-4 full length (TS4-FL) by CRB0017_IgG4. 0.2 µg of dialyzed/affinity purified TS4-FL were immunoprecipitated (IP) with anti-Sp_ADAMTS-5 CRB0017_IgG4 antibody (30 and 60 µg in lane 1 and 2, respectively) or with an unrelated antibody (30 µg) as a negative control (lane 3). In lane 4, dialyzed/affinity purified TS4-FL was loaded as a positive control. Immunoprecipitates were analysed by immunoblotting with anti-FLAG antibody (1:1000). CRB0017_IgG4-immunoprecipitated ~75 kDa TS5-FL band was observed corresponding to TS4-FL p68 protein. The molecular mass of immunoprecipitated TS4-FL protein is slightly higher than predicted from its amino acid composition and this is mainly due to N- and O-glycosylation in the protein. Molecular mass markers are indicated to the left-hand side of the Figure.

Reformatted chimeric immunoglobulin CRB0017_IgG4 displays the same immunoreactivity pattern in ELISA assay in a dose dependent fashion (FIG. 4). Similar results were obtained with the monoclonal antibodies CRB0102 and CRB0123 (data not shown). Moreover, the chimeric anti-Sp_ADAMTS-5 CRB0017_IgG4 (comprising mouse variable regions) was able to immunoprecipitate the recombinant ADAMTS-5 FL protein as well as recombinant human ADAMTS-4 FL (FIGS. 6 and 7). In addition, the authors carried out surface plasmon resonance (SPR) analyses to determine the binding kinetics of CRB0017_IgG4. The chimeric monoclonal antibody (mAb) was either immobilized on a CM5 chip followed by injections at various concentration of Sp_ADAMTS-5-GST or used as ligand in combination with Sp_ADAMTS-5-GST-immobilized sensor chip. Using a bivalent binding model, the authors determined steady state binding constants ($KD_2$). When used as binder, the authors measured a binding strengths by SPR around subnanomolar-7 nM of $KD_2$ (data not shown). CRB0017_IgG4 displayed also a strong affinity ($KD_1$ of ~2 nM) when immobilized on sensor chip (FIG. 5) that correlated better with the binding values as determined by antigen-specific ELISA (FIG. 4).

Evaluation of Binding Capacity of Anti-spacer ADAMTS-5 mAbs to ADAMTS-5 Target Antigen Purified ADAMTS-5 enzyme was challenged in ELISA using mAbs CRB0017_IgG4, CRB0093_IgG4, CRB094_IgG4, CRB0123_IgG4 and CRB0124_IgG4 in coating. As shown in FIG. 15, mAbs CRB0017, CRB0093, CRB0094 and CRB00124 showed comparable specificity to ADAMTS-5 while mAb CRB0123 IgG4 display a higher binding capacity for ADAMTS-5 than mAb CRB0017_IgG4 in this assay (FIG. 15).

Binding of Present Invention Antibodies on Hek-293-ADAMTS-5-3×FLAG/Hek-293 in Cell-ELISA Format.

Figure 11:
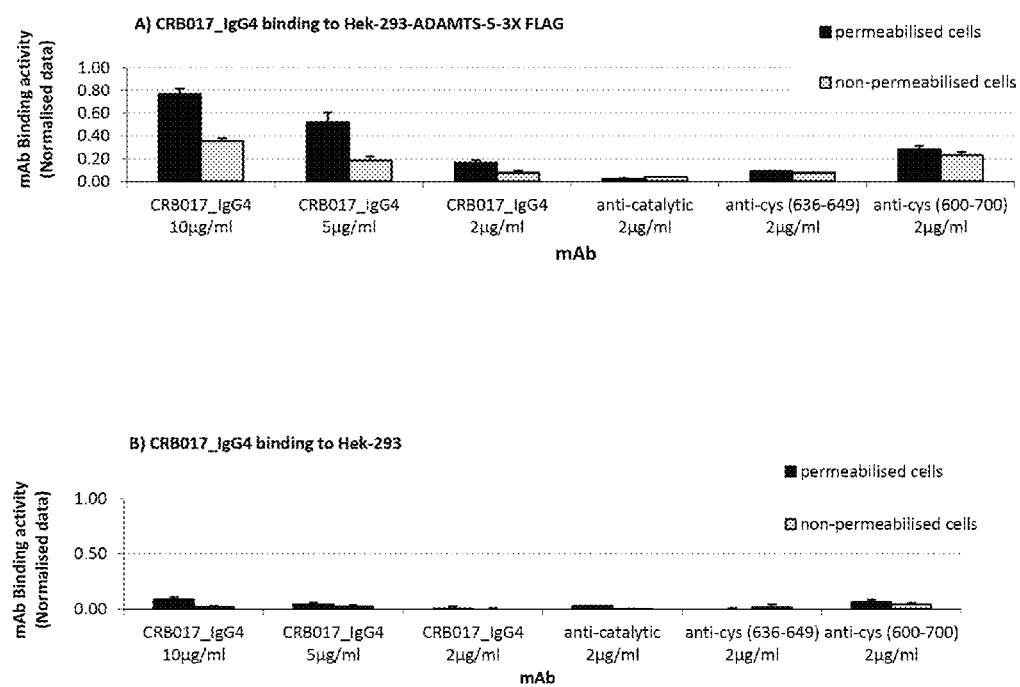
FIG. 11. A) CRB0017_IgG4 is able to recognize ADAMTS-5 secreted from permeabilized or non permeabilized cells in a dose dependent manner. As controls, anti-catalytic and two anti-cys domain of ADAMTS-5 commercial antibodies were used. B) CRB0017_IgG4 does not cross-reacted with any protein on the cell surface of HEK293 cells.

In-Cell ELISA use quantitative immunocytochemistry to measure protein expression or post-translational modifications in cultured cells. Cells are fixed in a 96-well plate and targets of interest are detected with highly specific, well-characterized monoclonal antibodies and levels are quantified with enzyme-labeled secondary antibodies. Using this method, the binding between full length ADAMTS-5 expressed by stable HEK293 line and CRB0017_IgG4 was evaluated. The enzyme is both efficiently secreted by this cell line and is also retained into the extracellular matrix (ECM). When CRB0017_IgG4 was challenged with this recombinant cell line, it was able to recognized, in a dose dependent manner, the enzyme ADAMTS-5 at its native folding condition (FIG. 11)

Evaluation of Binding Capacity of mAb CRB0017 to ADAMTS-5.

Supernatants harvested from FreeStyle™ 293-F cell line stably expressing ADAMTS-5 3×FLAG (the harvesting was done at every dilution of the pool of stably transfected cells) that contained the native full length enzyme ADAMTS-5 and FreeStyle™ 293-F cell lines were challenged in a sandwich ELISA assay using mAb CRB0017_IgG4 in coating. The supernatants were used immediately after collection, in order to preserve the function of ADAMTS-5 and to avoid as much as possible the autocatalysis of the enzyme.

Figure 12:
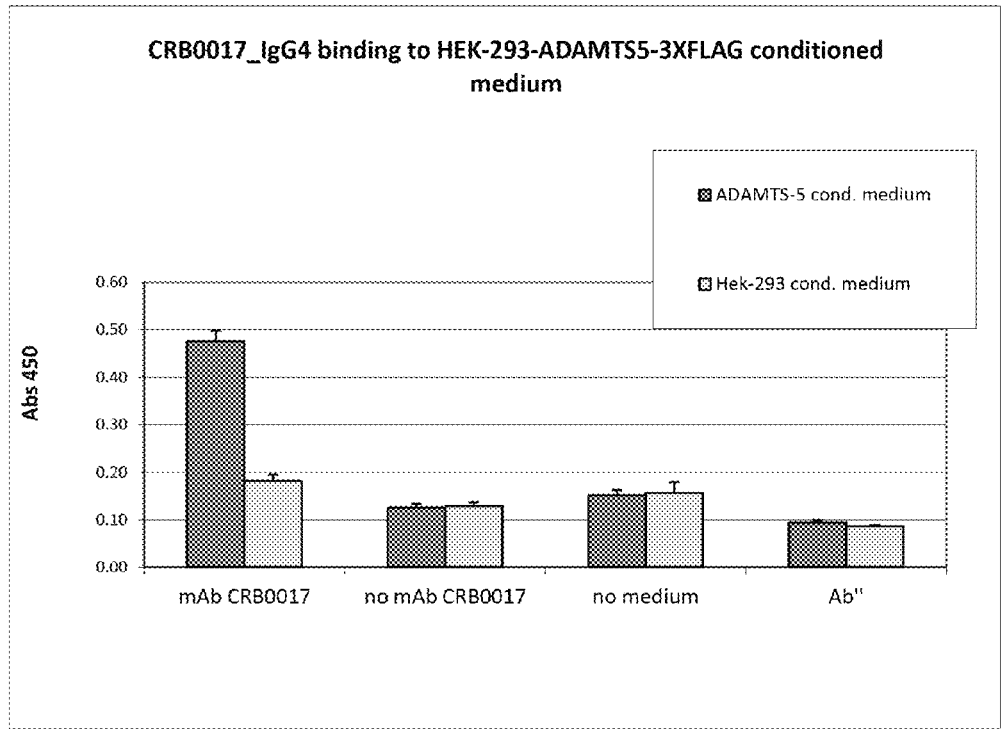
FIG. 12. Supernatants harvested from Hek293-ADAMTS-5 (ADAMTS-5 cond. Medium) and Hek293 (Hek-293 cond. Medium) were challenged in a sandwich ELISA using mAb CRB0017_IgG4 in coating as described in the material section below. "no mAb CRB0017" is a control condition in which wells are not coated with CRB0017_IgG4, "no medium" is a control condition in which no supernatant was added to the wells and "Ab" "is a control condition in which only the secondary antibody was added to the wells. As shown in figure, CRB0017_IgG4 is able to recognize ADAMTS-5 secreted from HEK293 expressing cells with high specificity.

As shown in FIG. 12, the antibody was able to recognize the enzyme ADAMTS-5 present in the conditioned medium with high specificity.

Evaluation of the Capacity of Syndecan-4 to Interfere in CRB0017_IgG$_4$ Anti-spacer ADAMTS-5 binding to ADAMTS-5 antigen.

It was demonstrated that syndecan-4 is functionally involved in cartilage degradation by hypertrophic OA chondrocytes through inhibiting the activation of ADAMTS-5 mediated aggrecan cleavage (Echtermeyer, F. et al. 2009. Nat Med. 15(9):1072-6). ADAMTS-5 activation depends on direct interaction with syndecan-4 on the surface of osteoarthritic chondrocytes; the mechanisms involved in cartilage degradation seem to involve both direct binding of ADAMTS-5 to Syndecan-4 and the regulation of ADAMTS-5 activation by MMP-3, which is regulated by Syndecan-4 in an ERK-dependent manner.

The exact pathways by which Syndecan-4 expression is induced during OA, as well as the mechanisms by which it is involved in cartilage remodelling, are still under intense investigation. In order to evaluate the possibility that mAb anti-ADAMTS-5 CRB0017 can modulate the pathological responses of chondrocytes mediated by Syndecan-4 we set up a preliminary in vitro assay to demonstrate the ability of mAb CRB0017 to interfere with ADAMTS-5-Syndecan-4 interaction. As shown in FIG. 14, when Syndecan-4 is added to the wells, the OD is decreased with respect to wells in which only ADAMTS-5 was added to CRB0017_IgG$_4$. This demonstrates that the specific interaction between ADAMTS-5 and mAb CRB0017 was effectively dissociated by Syndecan-4.

It was demonstrated that the spacer domain and the TSP type-1 domains are important for a tight interaction with the extracellular matrix. Moreover, it was demonstrated that ADAMTS-5 is bound to the heparan sulphate chains of Syndecan-4 and by this mechanism is fixed to the cell surface. It is not yet understood which is the domain of ADAMTS-5 involved in binding with Syndecan-4. Loss of binding as the final outcome of antibody action does not allow at the moment any conclusion on direct competition (same binding epitope) vs indirect (steric hindrance) mechanism for dissociation even if any mechanism finally leading to impaired binding properties have resulted in loss of interaction between ADAMTS-5 and Syndecan-4.

Measurement of Anti-ADAMTS-5 Neutralizing Activity.

Figure 8:
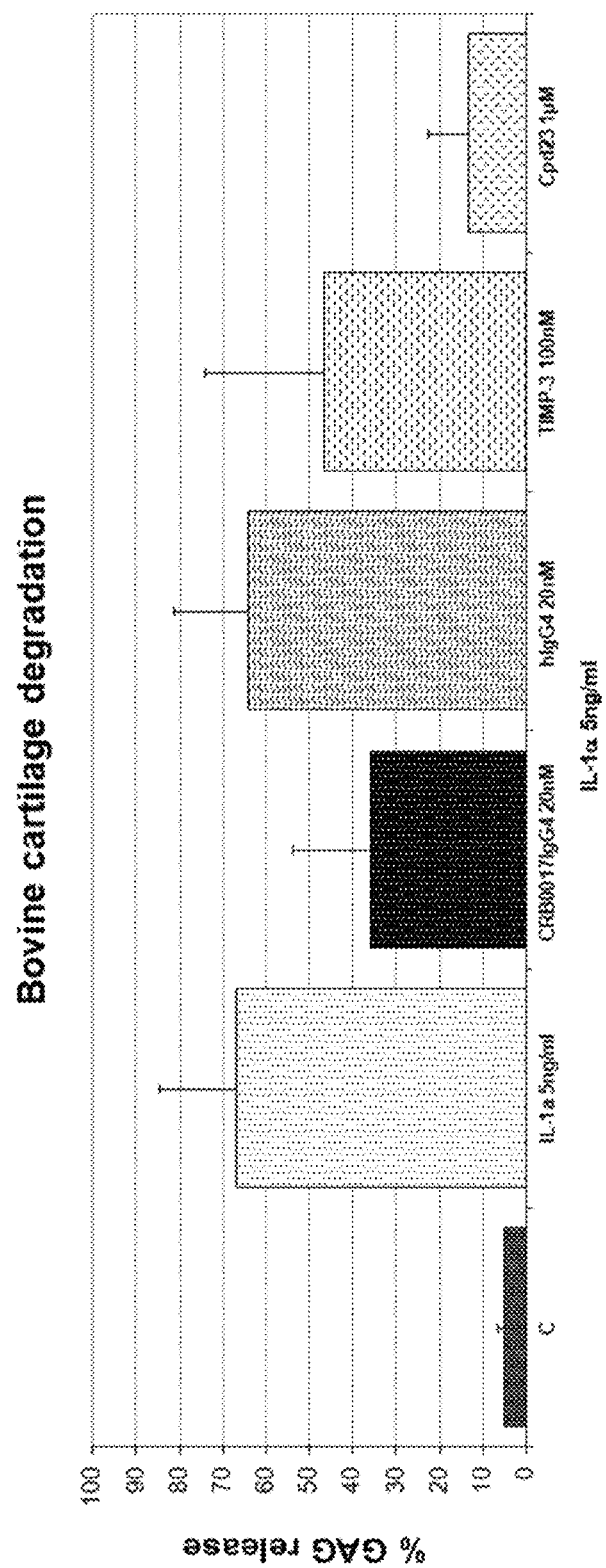
FIG. 8. Effect of anti-Sp_ADAMTS-5 IgG4 in in vitro proteolysis of bovine cartilage induced by IL-1α. Figure represents IL-1α 5 ng/ml activity in the absence or presence of CRB0017_IgG4 after 48 h of incubation (three different independent experiments). As a negative control in each experiments a human native IgG4 (Serotec) was used. As a positive control in each experiment a synthetic ADAMTS-5 inhibitor (Cpd 23) and a natural ADAMTS-5 inhibitor (TIMP-3) were used. The results are expressed as % GAG release, i.e. the quantitation of glycosaminoglycans (GAGs) in the form of aggrecan fragments released from the cartilage in culture; this method measures cytokine efficiency in simulating cartilage metabolism.
Figure 9:
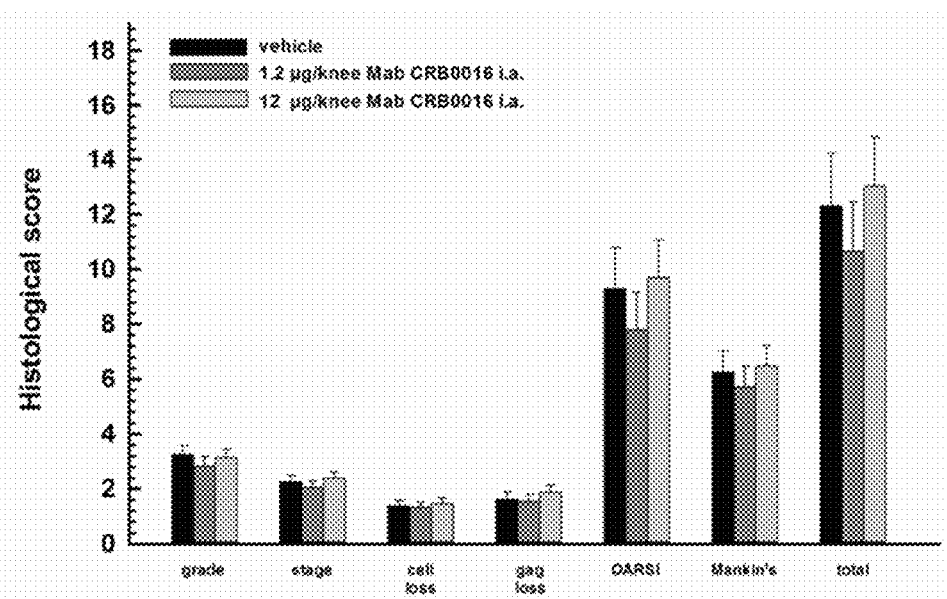
FIG. 9. Evaluation of the effect of the HelixB-ADAMTS-5 binding protein CRB0016_IgG4 in the STR/ort mouse model of osteoarthritis. CRB0016_IgG4 was administered intraarticularly in both knees of each animal, once at the start of the experiment and again after 6 weeks, at doses of 1.2 and 12 µg/knee. Three months after first administration, CRB0016_IgG4 did not modify the course of OA in the STR/ort mouse strain, as assessed histo-pathologically. Grade is defined as the depth of the lesion through the articular cartilage. Stage is defined as the horizontal extent of cartilage involvement within one side of a joint compartment irrespective of the underlying grade. Taken together, both constitute an index of the severity or pathologic progression of the osteoarthritic process, and indeed the OARSI score is defined as grade×stage. Cell loss is defined as the fraction of articular chondrocytes that have undergone cell death, within the articular compartment considered. GAG (glycosaminoglycan) loss is defined as and assessed by the loss of a cation stain that presents metachromasy towards GAGs, such as for instance Toluidine blue or Safranin O. Mankin has defined his score as the sum of grade, cell loss and GAG loss, while the total score is defined as the sum of the OARSI score and cell loss and GAG loss. All of the above parameters constitute features of OA, and their scoring gives a measure of the severity and progression of the pathology.
Figure 10:
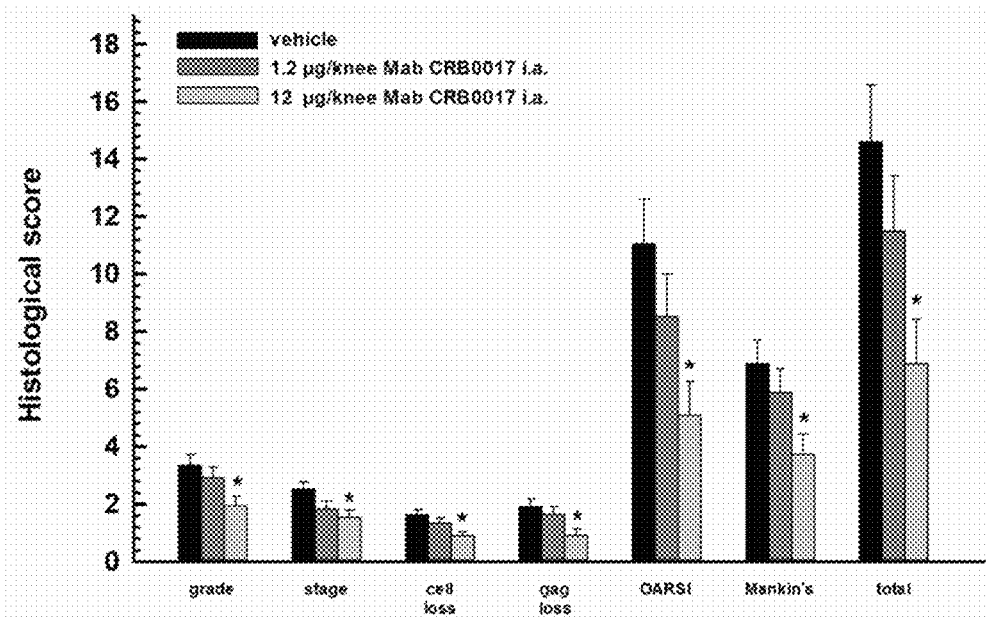
FIG. 10. Evaluation of the effect of CRB0017_IgG4 in the STR/ort mouse model of osteoarthritis. CRB0017_IgG4 was administered intraarticularly in both knees of each animal, once at the beginning of the experiment and again after 6 weeks, at doses of 1.2 and 12 µg/knee. Three months after first administration, CRB017 IgG4 showed a dose-dependent activity in reducing OA severity in the STR/ort mouse model. All parameters are defined as in FIG. 9.

The authors also evaluated the inhibition of IL-1α-induced aggrecan degradation in the bovine cartilage tissue. 48 h after the treatments, the proportion of total GAG remaining in the tissue was measured. This analysis revealed that CRB0017_IgG4 inhibited GAG release (50% inhibition) from tissue at 20 nM concentration (FIG. 8). In this experiment, the control antibody (nhIgG4) was not able to interfere with the enzyme at the same concentration. Moreover, the natural inhibitor TIMP-3 did not show markedly to inhibit the IL-1α-mediated conversion and release process when tested at the concentration of 20 nM (data not shown). The chemical compound Cpd23, a 3,3-dimethyl-5-hydroxypipecolic hydroxamate-based inhibitor of aggrecanase and MMP-13 (used at the concentration of 1 μM, Noe et al., 2005. Bioorg Med Chem Lett. 15:2808-2811), was used as positive control, because it displays a better inhibitory effect respect to the natural inhibitor TIMP-3 in this assay.

Evaluation of the Effect of CRB0016_IgG4 in the STR/Ort Mouse Model of Osteoarthritis.

The HelixB-ADAMTS-5 binding protein CRB0016 IgG4 was administered intraarticularly in both knees of each animal, once at the start of the experiment and again after 6 weeks, at doses of 1.2 and 12 μg/knee.

After three months, the authors observed that the knees from vehicle treated animals displayed severe OA with clefting and erosion of the articular cartilage to the subchondral bone, with prominent chondro-osseous metaplasias and often inflammation and pannus. No significant changes in any of the parameters examined were associated with administration of CRB0016_IgG4 at either dose.

The procedure of blind scoring of the histological samples did not show effect of the compound in decreasing cartilage damage. Taken together, these data show that knee intraarticular administration of the HelixB-ADAMTS-5 binding protein CRB0016_IgG4 twice in three months could not reduce the severity of the osteoarthritic pathology in the STR/ort mice.

Evaluation of the Effect of CRB0017_IgG4 in the STR/ort Mouse Model of Osteoarthritis.

CRB0017_IgG4 was administered intraarticularly in both knees of each animal, once at the start of the experiment and again after 6 weeks, at doses of 1.2 and 12 μg/knee. After three months, the authors observed that the knees from vehicle treated animals displayed severe OA with clefting and erosion of the articular cartilage to the subchondral bone, with prominent chondro-osseous metaplasias and often inflammation and pannus. OA Mankin's score was significantly decreased in the CRB0017_IgG4 12 μg group compared to vehicle. The OA grade×stage takes into account not only the depth of the damage (grade), but also its extension on the articular surface (stage). The OA grade× stage was significantly lower in the CRB0017_IgG4 12 μg group compared to vehicle. Administration of CRB0017_IgG4 1.2 μg was associated with a trend to a decrease with both scoring methods. In conclusion the authors observed that CRB0017_IgG4 can modify the course of OA in the STR/ort mouse strain, by delaying cartilage breakdown as assessed histologically. The procedure of blind scoring of the histological samples clearly showed a dose dependent effect of the compound in decreasing cartilage damage.

Taken together, these data show that knee intraarticular administration of CRB0017_IgG4 twice in three months dose-dependently reduced the severity of the osteoarthritic pathology in the STR/ort mice.

Evaluation of Present Invention Antibodies in the Medial Meniscal Tear (MMT) Rat Model of Osteoarthritis.

3 weeks after injection, the authors observed that the knees from vehicle treated animals displayed severe OA with clefting and erosion of the articular cartilage to the subchondral bone, with prominent osteophytes, inflammation and pannus. Administration of CRB0017_IgG4 was associated with a dose-related decrease in all histo-pathological severity scores (FIG. 13). The procedure of blind scoring of the histological samples showed a dose dependent decrease in OA severity following intra-articular treatment with CRB0017_IgG4.

Some proteolytic enzymes, in addition to their catalytic domains, have also non-catalytic ancillary domains that are important modulators of the interaction between the enzyme and substrate or inhibitors. Members of the ADAMTS family of enzymes degrade proteoglycans and thereby have the potential to alter tissue architecture and regulate cellular function.

In particular, ADAMTS-4 and ADAMTS-5 can cleave the aggrecan at various sites, releasing the chondroitin and keratansulfate-bearing regions of the molecule from the tissue. This was demonstrated to be an early and crucial step in the development of osteoarthritis. These enzymes can also be proteolyzed to smaller isoforms, which have altered proteolytic activity. Unfortunately, the 3D domain architecture of the full-length aggrecanases is not known, because it is very difficult to obtain the X-ray structures of these enzymes, due to their complex production and purification.

To date, only a portion of the entire X-ray structure of the ADAMTS-1, ADAMTS-4 and ADAMTS-5 enzymes are available (the structure solved by X-ray crystallography comprise only the catalytic and disintegrin domains) and thus it is impossible to extrapolate the arrangements and orientation of all the domains respect to the catalytic domain. The crystal structures of the catalytic and disintegrin domains of ADAMTS-4 and ADAMTS-5 determined by Mosyak (Mosyak et al., 2008. *Protein Sci.* 17:16-21) indicated that the enzymes display an 'open' form when it is bound to the inhibitor and a 'closed' form when it is auto-inhibited and nonbinding. On this basis, the author proposed that mature aggrecanase exists as a mix of two isomers, that can coexist in equilibrium. In this "ensemble" only one of this form is proteolytically active. Moreover, it was demonstrated that both full length form of ADAMTS-5 and ADAMTS-4 are highly active against their natural substrate, aggrecan, and the deletion of the C-terminal non-catalytic domains of the enzymes greatly reduces their activity (Kashiwagi et al., 2004. *J Biol Chem.* 279:10109-10119); (Gendron et al., 2007. *J Biol Chem.* 282:18294-18306); (Fushimi et al., 2008. *J Biol Chem.* 283:6706-6716). This suggests that the domains on their own or in the protein-binding fashion may perturb the equilibrium to the more open form.

The invention provides the evidence that antibodies directed against an ancillary non catalytic domain, such as the spacer domain of ADAMTS-5, strongly inhibit the enzymatic activity of this protein. In particular, the results obtained with the anti-spacer domain antibody CRB0017_IgG4 illustrate the concept that the inhibition of the aggrecanase-2 within the spacer domain is more effective than the inhibition of the enzyme within the catalytic domain. Notably, it has been shown that, while CRB0017_IgG4 is able to strongly inhibit in vitro and in vivo the proteolytic effect of ADAMTS-5, an anti-catalytic antibody, such as CRB0016_IgG4, is not able to produce such an effect.

The outstanding results obtained with the antibodies of the present invention, in particular with CRB0017_IgG4 are due to their blocking properties on the spacer domain of ADAMTS-5. By binding to the active site of ADAMTS-5, the antibodies of the invention trigger the enzyme to assume a "closed" form thus inhibit the enzyme directly or favour the interaction of the enzyme with its natural inhibitor TIMP-3, as hypothesized by Troeberg (Troeberg et al., 2009. *Matrix Biol.* 28:463-469).

Moreover, data obtained so far suggested that the inhibition of the binding between ADAMTS-5 and Syndecan-4 by mAb CRB0017_IgG4 could have a role in modulating the pathological responses of chondrocytes mediated by Syndecan-4.

Apart from induction of enzymes by activated chondrocytes, the function of Syndecan-4 is further regulated by interaction with matrix molecules and cell surface proteoglycans. Syndecan-4 is a transmembrane heparan sulfate proteoglycan that seems crucial for the activity of ADAMTS-5.

It was demonstrated that the loss of Syndecan-4 activity markedly reduced OA cartilage pathology in the murine DMM OA model. This was demonstrated both in Syndecan-4 knockouts as well as in WT mice, locally treated by intraarticular injections with Syndecan-4 specific antibodies. In vitro studies identified direct interaction of Syndecan-4 with ADAMTS-5. In addition, it was demonstrated that ADAMTS-5 activity is dependent on MMP-3 and the latter activity is controlled by Syndecan-4.

Syndecans undergo regulated proteolytic cleavage at ectodomain sites near the membrane by matrix metalloproteinases and metzincins family of endoproteases, a process called shedding, both as part of normal turnover as well as in response to external stimuli and is regulated by multiple pathways. Besides disrupting syndecan signaling, the released soluble ectodomain acts as an antagonist to compete with intact syndecans for its ligands. While syndecan ectodomain shedding is known to be activated by physiological stimulants and the ectodomains are being ascribed pathophysiological roles, in particular in tumorigenesis and inflammation, little is known about how their release from the cell surface is regulated. Thus it could be of interest to see if the anti-ADAMTS-5 CRB0017_IgG4 could help a further understanding of this process.

The invention claimed is:

1. An antibody able to recognize and bind an epitope in the amino acid 732 to amino acid 874 region of SEQ ID NO: 2 of ADAMTS-5, said antibody comprising a CDRH1 that consists of SEQ ID NO: 60, a CDRH2 that consists of SEQ ID NO: 61, a CDRH3 that consists of SEQ ID NO: 62, a CDRL1 that consists of SEQ ID NO: 27, a CDRL2 that consists of SEQ ID NO: 28 and a CDRL3 that consists of SEQ ID NO: 29.

2. The antibody of claim 1, that is a chimeric antibody, a humanized antibody, a deimmunized antibody, or a fully human antibody.

3. The antibody of claim 1, that is a monoclonal antibody.

4. The antibody of claim 1, that is a neutralizing antibody.

5. The antibody of claim 1, that comprises a VL chain that consists of SEQ ID NO: 3 and a VH chain that consists of SEQ ID NO: 4.

6. A pharmaceutical composition comprising at least one antibody according to claim 1, and pharmaceutically acceptable excipients.

7. The pharmaceutical composition according to claim 6, in a form suitable for intra-articular administration.

8. A method for treating osteoarthritis, comprising administering an effective amount of the antibody of claim 1, to a subject in need thereof.

9. The method according to claim 8, comprising administering the antibody to the subject by an intra-articular route.

* * * * *

SEQUENCE LISTING

<160> NUMBER OF SEQ ID NOS: 216

<210> SEQ ID NO 1
<211> LENGTH: 837
<212> TYPE: PRT
<213> ORGANISM: Homo sapiens

<400> SEQUENCE: 1

```
Met Ser Gln Thr Gly Ser His Pro Gly Arg Gly Leu Ala Gly Arg Trp
1               5                   10                  15

Leu Trp Gly Ala Gln Pro Cys Leu Leu Leu Pro Ile Val Pro Leu Ser
                20                  25                  30

Trp Leu Val Trp Leu Leu Leu Leu Leu Ala Ser Leu Leu Pro Ser
            35                  40                  45

Ala Arg Leu Ala Ser Pro Leu Pro Arg Glu Glu Glu Ile Val Phe Pro
    50                  55                  60

Glu Lys Leu Asn Gly Ser Val Leu Pro Gly Ser Gly Ala Pro Ala Arg
65                  70                  75                  80

Leu Leu Cys Arg Leu Gln Ala Phe Gly Glu Thr Leu Leu Leu Glu Leu
                85                  90                  95

Glu Gln Asp Ser Gly Val Gln Val Glu Gly Leu Thr Val Gln Tyr Leu
                100                 105                 110

Gly Gln Ala Pro Glu Leu Leu Gly Gly Ala Glu Pro Gly Thr Tyr Leu
            115                 120                 125

Thr Gly Thr Ile Asn Gly Asp Pro Glu Ser Val Ala Ser Leu His Trp
        130                 135                 140
```

-continued

```
Asp Gly Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
            165                 170                 175

Gly Ala His Ile Leu Arg Arg Lys Ser Pro Ala Ser Gly Gln Gly Pro
        180                 185                 190

Met Cys Asn Val Lys Ala Pro Leu Gly Ser Pro Ser Pro Arg Pro Arg
    195                 200                 205

Arg Ala Lys Arg Phe Ala Ser Leu Ser Arg Phe Val Glu Thr Leu Val
210                 215                 220

Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
        260                 265                 270

Gly Ser Gly Glu Glu Gly Pro Gln Val Gly Pro Ser Ala Ala Gln Thr
        275                 280                 285

Leu Arg Ser Phe Cys Ala Trp Gln Arg Gly Leu Asn Thr Pro Glu Asp
290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
                325                 330                 335

Thr Val Cys Asp Pro Ala Arg Ser Cys Ala Ile Val Glu Asp Asp Gly
        340                 345                 350

Leu Gln Ser Ala Phe Thr Ala Ala His Glu Leu Gly His Val Phe Asn
        355                 360                 365

Met Leu His Asp Asn Ser Lys Pro Cys Ile Ser Leu Asn Gly Pro Leu
    370                 375                 380

Ser Thr Ser Arg His Val Met Ala Pro Val Met Ala His Val Asp Pro
385                 390                 395                 400

Glu Glu Pro Trp Ser Pro Cys Ser Ala Arg Phe Ile Thr Asp Phe Leu
                405                 410                 415

Asp Asn Gly Tyr Gly His Cys Leu Leu Asp Lys Pro Glu Ala Pro Leu
            420                 425                 430

His Leu Pro Val Thr Phe Pro Gly Lys Asp Tyr Asp Ala Asp Arg Gln
        435                 440                 445

Cys Gln Leu Thr Phe Gly Pro Asp Ser Arg His Cys Pro Gln Leu Pro
    450                 455                 460

Pro Pro Cys Ala Ala Leu Trp Cys Ser Gly His Leu Asn Gly His Ala
465                 470                 475                 480

Met Cys Gln Thr Lys His Ser Pro Trp Ala Asp Gly Thr Pro Cys Gly
                485                 490                 495

Pro Ala Gln Ala Cys Met Gly Gly Arg Cys Leu His Met Asp Gln Leu
            500                 505                 510

Gln Asp Phe Asn Ile Pro Gln Ala Gly Gly Trp Gly Pro Trp Gly Pro
        515                 520                 525

Trp Gly Asp Cys Ser Arg Thr Cys Gly Gly Gly Val Gln Phe Ser Ser
    530                 535                 540

Arg Asp Cys Thr Arg Pro Val Pro Arg Asn Gly Gly Lys Tyr Cys Glu
545                 550                 555                 560
```

Gly Arg Arg Thr Arg Phe Arg Ser Cys Asn Thr Glu Asp Cys Pro Thr
            565                 570                 575

Gly Ser Ala Leu Thr Phe Arg Glu Glu Gln Cys Ala Ala Tyr Asn His
        580                 585                 590

Arg Thr Asp Leu Phe Lys Ser Phe Pro Gly Met Asp Trp Val Pro
        595                 600                 605

Arg Tyr Thr Gly Val Ala Pro Gln Asp Gln Cys Lys Leu Thr Cys Gln
        610                 615                 620

Ala Gln Ala Leu Gly Tyr Tyr Val Leu Glu Pro Arg Val Val Asp
625                 630                 635                 640

Gly Thr Pro Cys Ser Pro Asp Ser Ser Val Cys Val Gln Gly Arg
                645                 650                 655

Cys Ile His Ala Gly Cys Asp Arg Ile Ile Gly Ser Lys Lys Lys Phe
            660                 665                 670

Asp Lys Cys Met Val Cys Gly Asp Gly Ser Gly Cys Ser Lys Gln
        675                 680                 685

Ser Gly Ser Phe Arg Lys Phe Arg Tyr Gly Tyr Asn Asn Val Val Thr
    690                 695                 700

Ile Pro Ala Gly Ala Thr His Ile Leu Val Arg Gln Gln Gly Asn Pro
705                 710                 715                 720

Gly His Arg Ser Ile Tyr Leu Ala Leu Lys Leu Pro Asp Gly Ser Tyr
                725                 730                 735

Ala Leu Asn Gly Glu Tyr Thr Leu Met Pro Ser Pro Thr Asp Val Val
            740                 745                 750

Leu Pro Gly Ala Val Ser Leu Arg Tyr Ser Gly Ala Thr Ala Ala Ser
        755                 760                 765

Glu Thr Leu Ser Gly His Gly Pro Leu Ala Gln Pro Leu Thr Leu Gln
    770                 775                 780

Val Leu Val Ala Gly Asn Pro Gln Asp Thr Arg Leu Arg Tyr Ser Phe
785                 790                 795                 800

Phe Val Pro Arg Pro Thr Pro Ser Thr Pro Arg Pro Thr Pro Gln Asp
                805                 810                 815

Trp Leu His Arg Arg Ala Gln Ile Leu Glu Ile Leu Arg Arg Pro
        820                 825                 830

Trp Ala Gly Arg Lys
        835

<210> SEQ ID NO 2
<211> LENGTH: 930
<212> TYPE: PRT
<213> ORGANISM: Homo sapiens

<400> SEQUENCE: 2

Met Leu Leu Gly Trp Ala Ser Leu Leu Leu Cys Ala Phe Arg Leu Pro
1               5                   10                  15

Leu Ala Ala Val Gly Pro Ala Thr Pro Ala Gln Asp Lys Ala Gly
            20                  25                  30

Gln Pro Pro Thr Ala Ala Ala Ala Gln Pro Arg Arg Arg Gln Gly
        35                  40                  45

Glu Glu Val Gln Glu Arg Ala Glu Pro Gly His Pro His Pro Leu
    50                  55                  60

Ala Gln Arg Arg Arg Ser Lys Gly Leu Val Gly Asn Ile Asp Gln Leu
65                  70                  75                  80

Tyr Ser Gly Gly Gly Lys Val Gly Tyr Leu Val Tyr Ala Gly Gly Arg
                85                  90                  95

```
Arg Phe Leu Leu Asp Leu Glu Arg Asp Gly Ser Val Gly Ile Ala Gly
            100                 105                 110

Phe Val Pro Ala Gly Gly Thr Ser Ala Pro Trp Arg His Arg Ser
        115                 120                 125

His Cys Phe Tyr Arg Gly Thr Val Asp Gly Ser Pro Arg Ser Leu Ala
130                 135                 140

Val Phe Asp Leu Cys Gly Gly Leu Asp Gly Phe Phe Ala Val Lys His
145                 150                 155                 160

Ala Arg Tyr Thr Leu Lys Pro Leu Leu Arg Gly Pro Trp Ala Glu Glu
                165                 170                 175

Glu Lys Gly Arg Val Tyr Gly Asp Gly Ser Ala Arg Ile Leu His Val
            180                 185                 190

Tyr Thr Arg Glu Gly Phe Ser Phe Glu Ala Leu Pro Pro Arg Ala Ser
        195                 200                 205

Cys Glu Thr Pro Ala Ser Thr Pro Glu Ala His Glu His Ala Pro Ala
210                 215                 220

His Ser Asn Pro Ser Gly Arg Ala Ala Leu Ala Ser Gln Leu Leu Asp
225                 230                 235                 240

Gln Ser Ala Leu Ser Pro Ala Gly Gly Ser Gly Pro Gln Thr Trp Trp
                245                 250                 255

Arg Arg Arg Arg Arg Ser Ile Ser Arg Ala Arg Gln Val Glu Leu Leu
            260                 265                 270

Leu Val Ala Asp Ala Ser Met Ala Arg Leu Tyr Gly Arg Gly Leu Gln
        275                 280                 285

His Tyr Leu Leu Thr Leu Ala Ser Ile Ala Asn Arg Leu Tyr Ser His
290                 295                 300

Ala Ser Ile Glu Asn His Ile Arg Leu Ala Val Val Lys Val Val Val
305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
            340                 345                 350

Asp Asp His Glu His Tyr Asp Ala Ala Ile Leu Phe Thr Arg Glu
        355                 360                 365

Asp Leu Cys Gly His His Ser Cys Asp Thr Leu Gly Met Ala Asp Val
370                 375                 380

Gly Thr Ile Cys Ser Pro Glu Arg Ser Cys Ala Val Ile Glu Asp Asp
385                 390                 395                 400

Gly Leu His Ala Ala Phe Thr Val Ala His Glu Ile Gly His Leu Leu
                405                 410                 415

Gly Leu Ser His Asp Asp Ser Lys Phe Cys Glu Glu Thr Phe Gly Ser
            420                 425                 430

Thr Glu Asp Lys Arg Leu Met Ser Ser Ile Leu Thr Ser Ile Asp Ala
        435                 440                 445

Ser Lys Pro Trp Ser Lys Cys Thr Ser Ala Thr Ile Thr Glu Phe Leu
450                 455                 460

Asp Asp Gly His Gly Asn Cys Leu Leu Asp Leu Pro Arg Lys Gln Ile
465                 470                 475                 480

Leu Gly Pro Glu Glu Leu Pro Gly Gln Thr Tyr Asp Ala Thr Gln Gln
                485                 490                 495

Cys Asn Leu Thr Phe Gly Pro Glu Tyr Ser Val Cys Pro Gly Met Asp
            500                 505                 510
```

```
Val Cys Ala Arg Leu Trp Cys Ala Val Val Arg Gln Gly Gln Met Val
            515                 520                 525
Cys Leu Thr Lys Lys Leu Pro Ala Val Glu Gly Thr Pro Cys Gly Lys
        530                 535                 540
Gly Arg Ile Cys Leu Gln Gly Lys Cys Val Asp Lys Thr Lys Lys Lys
545                 550                 555                 560
Tyr Tyr Ser Thr Ser Ser His Gly Asn Trp Gly Ser Trp Gly Ser Trp
                565                 570                 575
Gly Gln Cys Ser Arg Ser Cys Gly Gly Val Gln Phe Ala Tyr Arg
            580                 585                 590
His Cys Asn Asn Pro Ala Pro Arg Asn Asn Gly Arg Tyr Cys Thr Gly
        595                 600                 605
Lys Arg Ala Ile Tyr Arg Ser Cys Ser Leu Met Pro Cys Pro Pro Asn
    610                 615                 620
Gly Lys Ser Phe Arg His Glu Gln Cys Glu Ala Lys Asn Gly Tyr Gln
625                 630                 635                 640
Ser Asp Ala Lys Gly Val Lys Thr Phe Val Glu Trp Val Pro Lys Tyr
                645                 650                 655
Ala Gly Val Leu Pro Ala Asp Val Cys Lys Leu Thr Cys Arg Ala Lys
            660                 665                 670
Gly Thr Gly Tyr Tyr Val Val Phe Ser Pro Lys Val Thr Asp Gly Thr
        675                 680                 685
Glu Cys Arg Leu Tyr Ser Asn Ser Val Cys Val Arg Gly Lys Cys Val
    690                 695                 700
Arg Thr Gly Cys Asp Gly Ile Ile Gly Ser Lys Leu Gln Tyr Asp Lys
705                 710                 715                 720
Cys Gly Val Cys Gly Gly Asp Asn Ser Ser Cys Thr Lys Ile Val Gly
                725                 730                 735
Thr Phe Asn Lys Lys Ser Lys Gly Tyr Thr Asp Val Val Arg Ile Pro
            740                 745                 750
Glu Gly Ala Thr His Ile Lys Val Arg Gln Phe Lys Ala Lys Asp Gln
        755                 760                 765
Thr Arg Phe Thr Ala Tyr Leu Ala Leu Lys Lys Lys Asn Gly Glu Tyr
    770                 775                 780
Leu Ile Asn Gly Lys Tyr Met Ile Ser Thr Ser Glu Thr Ile Ile Asp
785                 790                 795                 800
Ile Asn Gly Thr Val Met Asn Tyr Ser Gly Trp Ser His Arg Asp Asp
                805                 810                 815
Phe Leu His Gly Met Gly Tyr Ser Ala Thr Lys Glu Ile Leu Ile Val
            820                 825                 830
Gln Ile Leu Ala Thr Asp Pro Thr Lys Pro Leu Asp Val Arg Tyr Ser
        835                 840                 845
Phe Phe Val Pro Lys Lys Ser Thr Pro Lys Val Asn Ser Val Thr Ser
    850                 855                 860
His Gly Ser Asn Lys Val Gly Ser His Thr Ser Gln Pro Gln Trp Val
865                 870                 875                 880
Thr Gly Pro Trp Leu Ala Cys Ser Arg Thr Cys Asp Thr Gly Trp His
                885                 890                 895
Thr Arg Thr Val Gln Cys Gln Asp Gly Asn Arg Lys Leu Ala Lys Gly
            900                 905                 910
Cys Pro Leu Ser Gln Arg Pro Ser Ala Phe Lys Gln Cys Leu Leu Lys
        915                 920                 925
Lys Cys
```

<210> SEQ ID NO 3
<211> LENGTH: 112
<212> TYPE: PRT
<213> ORGANISM: Mus musculus

<400> SEQUENCE: 3

Asp Ile Val Ile Thr Gln Asp Glu Leu Ser Asn Pro Val Thr Ser Gly
1               5                   10                  15

Glu Ser Val Ser Ile Ser Cys Arg Ser Ser Lys Ser Leu Leu Tyr Lys
            20                  25                  30

Asp Gly Lys Thr Tyr Leu Tyr Trp Phe Leu Gln Arg Pro Gly Gln Ser
        35                  40                  45

Pro Gln Leu Pro Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
                85                  90                  95

Val Glu Tyr Pro Tyr Thr Phe Gly Gly Gly Thr Lys Leu Glu Ile Lys
            100                 105                 110

<210> SEQ ID NO 4
<211> LENGTH: 117
<212> TYPE: PRT
<213> ORGANISM: Mus musculus

<400> SEQUENCE: 4

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Gly Ser Leu Thr Ser Glu Asp Ser Ala Val Tyr Tyr Cys
                85                  90                  95

Ala Arg Gly Gly Tyr Asp Asp Leu Gly Tyr Trp Gly Gln Gly Thr Thr
            100                 105                 110

Leu Thr Val Ser Ser
        115

<210> SEQ ID NO 5
<211> LENGTH: 110
<212> TYPE: PRT
<213> ORGANISM: Mus musculus

<400> SEQUENCE: 5

Asp Ile Val Met Thr Gln Ser Pro Ala Ser Leu Ala Val Ser Gln Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

```
Lys Leu Pro Ile Tyr Leu Ala Ser Asn Leu Glu Ser Gly Val Pro Ala
        50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                 85                  90                  95

Glu Glu Leu Thr Phe Gly Ala Gly Thr Lys Leu Glu Leu Lys
            100                 105                 110

<210> SEQ ID NO 6
<211> LENGTH: 117
<212> TYPE: PRT
<213> ORGANISM: Mus musculus

<400> SEQUENCE: 6

Glu Val Lys Leu Leu Glu Ser Gly Gly Gly Leu Val Gln Pro Gly Gly
 1               5                  10                  15

Ser Leu Lys Leu Ser Cys Thr Thr Ser Gly Phe Asp Phe Ser Arg Tyr
             20                  25                  30

Trp Met Ser Trp Val Arg Gln Ala Pro Gly Lys Gly Leu Glu Trp Ile
         35                  40                  45

Gly Glu Ile Asn Pro Asp Ser Ser Thr Ile Asn Tyr Thr Pro Ser Leu
     50                  55                  60

Lys Asp Lys Phe Ile Ile Ser Arg Asp Asn Ala Lys Asn Thr Leu Tyr
 65                  70                  75                  80

Leu Gln Met Ser Lys Val Arg Ser Glu Asp Thr Ala Leu Tyr Tyr Cys
                 85                  90                  95

Ala Arg Arg Ser Tyr Trp Tyr Phe Asp Val Trp Gly Ala Gly Thr Ser
            100                 105                 110

Val Thr Val Ser Ser
        115

<210> SEQ ID NO 7
<211> LENGTH: 107
<212> TYPE: PRT
<213> ORGANISM: Mus musculus

<400> SEQUENCE: 7

Asp Ile Val Met Thr Gln Ser His Lys Phe Met Ser Thr Ser Glu Gly
 1               5                  10                  15

Asp Arg Val Ser Ile Thr Cys Lys Ala Ser Gln Asp Val Gly Thr Ala
             20                  25                  30

Val Ala Trp Tyr Gln Gln Lys Pro Gly Gln Ser Pro Lys Leu Leu Ile
         35                  40                  45

Tyr Trp Ala Ser Thr Arg His Thr Gly Val Pro Asp Arg Phe Thr Gly
     50                  55                  60

Ser Gly Ser Gly Thr Asp Phe Thr Leu Thr Ile Ser Asn Val Gln Ser
 65                  70                  75                  80

Glu Asp Leu Ala Asp Tyr Ile Cys Gln Gln Tyr Cys Ser His Pro Tyr
                 85                  90                  95

Thr Phe Gly Ala Gly Thr Lys Leu Glu Ile Lys
            100                 105

<210> SEQ ID NO 8
<211> LENGTH: 116
<212> TYPE: PRT
<213> ORGANISM: Mus musculus
```

-continued

<400> SEQUENCE: 8

Gln Val Gln Leu Gln Gln Ser Gly Ala Glu Pro Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala His Gly Arg Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Ser Ser Glu Asp Thr Ala Val Tyr Tyr Cys
                85                  90                  95

Ala Phe Tyr Ser Tyr Ala Ile Asp Tyr Trp Gly Gln Gly Thr Ser Val
            100                 105                 110

Thr Val Ser Ser
        115

<210> SEQ ID NO 9
<211> LENGTH: 107
<212> TYPE: PRT
<213> ORGANISM: Homo sapiens

<400> SEQUENCE: 9

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ala Ile Gly Asn Asp
            20                  25                  30

Leu Ala Trp Tyr Gln Gln Arg Pro Gly Lys Ala Pro Lys Arg Leu Ile
        35                  40                  45

Tyr Gly Ala Ser Thr Leu Ser Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Asn Phe Pro Tyr
                85                  90                  95

Thr Phe Gly Leu Gly Thr Lys Val Glu Ile Lys
            100                 105

<210> SEQ ID NO 10
<211> LENGTH: 127
<212> TYPE: PRT
<213> ORGANISM: Homo sapiens

<400> SEQUENCE: 10

Gln Val Gln Leu Gln Gln Trp Gly Ala Gly Leu Leu Lys Pro Ser Glu
1               5                   10                  15

Thr Leu Ser Leu Thr Cys Ala Val His Gly Gly Ser Phe Ser Gly Asn
            20                  25                  30

Phe Trp Ser Trp Val Arg Gln His Pro Gly Lys Gly Leu Glu Trp Ile
        35                  40                  45

Gly Glu Val Asn His Arg Gly Ser Ala Thr Tyr Asn Pro Ser Leu Lys
    50                  55                  60

Ser Arg Val Thr Met Ser Val Asp Thr Ser Lys Asn Gln Phe Ser Leu
65                  70                  75                  80

```
Gln Leu Ser Ser Val Thr Ala Ala Asp Thr Ala Val Tyr Tyr Cys Ala
            85                  90                  95

Arg Lys Leu Pro Arg Arg Ala Glu Asp Arg Pro Ser Ser Leu Arg
        100                 105                 110

Pro Phe Asp Tyr Trp Gly Gln Gly Thr Leu Val Thr Val Ser Ser
        115                 120                 125
```

<210> SEQ ID NO 11
<211> LENGTH: 112
<212> TYPE: PRT
<213> ORGANISM: Homo sapiens

<400> SEQUENCE: 11

```
Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asp Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Asn Ser
                85                  90                  95

Leu Ser Gly Tyr Ala Val Phe Gly Gly Gly Thr Gln Leu Thr Val Leu
            100                 105                 110
```

<210> SEQ ID NO 12
<211> LENGTH: 130
<212> TYPE: PRT
<213> ORGANISM: Homo sapiens

<400> SEQUENCE: 12

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Arg Phe Ser Ser His
            20                  25                  30

Asp Met His Trp Val Arg Gln Val Pro Gly Lys Gly Leu Glu Trp Val
        35                  40                  45

Ser Arg Ile Gly Thr Val Gly Asp Thr Tyr Tyr Ala Asp Ser Val Lys
    50                  55                  60

Gly Arg Phe Thr Ile Ser Arg Asp Asn Ser Lys Asn Thr Leu Phe Leu
65                  70                  75                  80

Gln Met Asn Ser Leu Gly Ala Glu Asp Thr Ala Val Tyr Tyr Cys Ala
                85                  90                  95

Arg Asp Gly Thr Arg Tyr Cys Ser Arg Thr Ser Cys His Ser Gly Tyr
            100                 105                 110

Tyr Tyr Tyr Gly Met Asp Val Trp Gly Gln Gly Thr Thr Val Thr Val
        115                 120                 125

Ser Ser
130
```

<210> SEQ ID NO 13
<211> LENGTH: 107
<212> TYPE: PRT
<213> ORGANISM: Homo sapiens

```
<400> SEQUENCE: 13

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105

<210> SEQ ID NO 14
<211> LENGTH: 121
<212> TYPE: PRT
<213> ORGANISM: Homo sapiens

<400> SEQUENCE: 14

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Ile Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Lys Thr
65                  70                  75                  80

Leu Tyr Leu Gln Met Thr Ser Leu Lys Thr Asp Asp Thr Ala Leu Tyr
                85                  90                  95

Tyr Cys Ala Arg Asp Leu Gly Ala Ser Asp Ala Phe Gly Leu Trp Gly
            100                 105                 110

Gln Gly Thr Thr Val Thr Val Ser Ser
        115                 120

<210> SEQ ID NO 15
<211> LENGTH: 110
<212> TYPE: PRT
<213> ORGANISM: Homo sapiens

<400> SEQUENCE: 15

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Leu Ile Tyr Asp Val Ser Asn Arg Pro Ser Gly Val Ser Ser Arg Phe
    50                  55                  60

Ser Gly Ser Lys Ser Gly Asn Ser Ala Ser Leu Thr Ile Ser Gly Leu
65                  70                  75                  80

Gln Ala Glu Asp Glu Ala Asp Tyr Tyr Cys Ser Ser Tyr Thr Arg Arg
```

```
                    85                  90                  95
Ser Thr Leu Glu Phe Gly Gly Gly Thr Lys Leu Thr Val Leu
            100                 105                 110

<210> SEQ ID NO 16
<211> LENGTH: 129
<212> TYPE: PRT
<213> ORGANISM: Homo sapiens

<400> SEQUENCE: 16

Gln Val Gln Leu Gln Gln Trp Gly Ala Gly Leu Leu Lys Pro Ser Gly
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr Ile Trp Ser Thr Arg His Asp Phe Trp Ser Gly Tyr Tyr Ser
            100                 105                 110

Ser Asn Trp Phe Asp Pro Trp Gly Gln Gly Thr Leu Val Thr Val Ser
        115                 120                 125

Ser

<210> SEQ ID NO 17
<211> LENGTH: 107
<212> TYPE: PRT
<213> ORGANISM: Homo sapiens

<400> SEQUENCE: 17

Glu Thr Thr Leu Thr Gln Ser Pro Ala Phe Met Ser Ala Thr Pro Gly
1               5                   10                  15

Asp Lys Ile Tyr Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
    50                  55                  60

Ser Gly Tyr Gly Thr Asp Phe Thr Leu Thr Ile Asn Asn Met Glu Ser
65                  70                  75                  80

Glu Asp Ala Ala Tyr Tyr Phe Cys Pro Gln Gln Asp Asn Val Pro Leu
                85                  90                  95

Thr Phe Gly Gly Gly Thr Lys Val Asp Ile Lys
            100                 105

<210> SEQ ID NO 18
<211> LENGTH: 122
<212> TYPE: PRT
<213> ORGANISM: Homo sapiens

<400> SEQUENCE: 18

Glu Val Gln Leu Val Glu Ser Gly Ser Asp Val Lys Lys Pro Gly Ala
1               5                   10                  15
```

```
Ser Val Arg Val Ser Cys Lys Val Ser Gly Tyr Arg Leu Thr Glu Tyr
            20                  25                  30

Pro Ile His Trp Val Arg Gln Ala Pro Gly Lys Gly Leu Glu Tyr Met
            35                  40                  45

Gly Gly Phe Asp Leu Glu Asn Gly Val Thr Lys Ala Ala Pro Arg Phe
 50                  55                  60

Arg Gly Arg Phe Thr Met Thr Glu Asp Thr Ser Thr Asp Ser Val Tyr
 65                  70                  75                  80

Met Glu Leu Lys Ser Leu Thr Ser Glu Asp Thr Ala Val Tyr Tyr Cys
                85                  90                  95

Val Lys Gly Pro Gly Tyr Gly Ala Leu Val Thr Ser Phe Thr Ser Trp
                100                 105                 110

Gly Leu Gly Thr Leu Val Thr Val Ser Ser
            115                 120

<210> SEQ ID NO 19
<211> LENGTH: 116
<212> TYPE: PRT
<213> ORGANISM: Homo sapiens

<400> SEQUENCE: 19

Gln Ser Val Leu Thr Gln Pro Pro Ser Ala Ser Ala Ser Leu Gly Ala
  1               5                  10                  15

Ser Val Thr Leu Thr Cys Thr Leu Ser Ser Gly Tyr Ser Asn Tyr Lys
            20                  25                  30

Val Asp Trp Tyr Gln Gln Thr Pro Gly Lys Gly Pro Arg Phe Val Met
            35                  40                  45

Arg Val Gly Thr Gly Gly Thr Val Gly Ser Lys Gly Asp Gly Ile Pro
 50                  55                  60

Asp Arg Phe Ser Val Leu Gly Ser Gly Leu Asn Arg Tyr Leu Ile Ile
 65                  70                  75                  80

Lys Asn Ile Gln Glu Glu Asp Glu Thr Asp Tyr His Cys Gly Ala Asp
                85                  90                  95

His Gly Ser Gly Ser Asn Phe Val Tyr Val Phe Gly Ser Gly Thr Lys
                100                 105                 110

Val Thr Val Leu
            115

<210> SEQ ID NO 20
<211> LENGTH: 121
<212> TYPE: PRT
<213> ORGANISM: Homo sapiens

<400> SEQUENCE: 20

Gln Val Gln Leu Gln Glu Ser Gly Gly Gly Leu Val Arg Pro Gly Gly
  1               5                  10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
            35                  40                  45

Ser Ala Ile Ser Gly Ser Gly Asp Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asp Ser Leu Arg Val Glu Asp Thr Ala Val Tyr Tyr Cys
                85                  90                  95
```

```
Ala Arg Asp Arg Asp Leu Leu His Lys Asp Gly Phe Asp Ile Trp Gly
            100                 105                 110
Gln Gly Thr Met Val Thr Val Ser Ser
        115                 120

<210> SEQ ID NO 21
<211> LENGTH: 107
<212> TYPE: PRT
<213> ORGANISM: Homo sapiens

<400> SEQUENCE: 21

Asp Ile Gln Met Thr Gln Ser Pro Ser Ser Val Ser Ala Ser Val Gly
1               5                   10                  15
Asp Arg Val Thr Ile Thr Cys Arg Pro Ser Gln Gly Ile Gly Lys Tyr
            20                  25                  30
Ser Ala Trp Tyr Gln Gln Lys Pro Gly Lys Ala Pro Glu Leu Pro Ile
        35                  40                  45
Tyr Leu Ala Ser Thr Leu Gln Ser Gly Val Pro Ser Arg Phe Ser Asp
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln Arg Asn Thr Tyr Pro Trp
                85                  90                  95
Thr Phe Gly Gln Gly Thr Lys Val Glu Ile Lys
            100                 105

<210> SEQ ID NO 22
<211> LENGTH: 117
<212> TYPE: PRT
<213> ORGANISM: Homo sapiens

<400> SEQUENCE: 22

Gln Val Gln Leu Gln Glu Ser Gly Gly Val Val Gln Pro Gly Arg
1               5                   10                  15
Ser Leu Arg Leu Ser Cys Ala Ala Ser Gly Phe Thr Phe Ser Gly Tyr
            20                  25                  30
Gly Met Asn Trp Val Arg Gln Ala Pro Gly Thr Gly Leu Glu Trp Val
        35                  40                  45
Ala Thr Ile Ser Phe Asp Gly Thr Asp Lys Tyr Tyr Ala Asp Ser Val
    50                  55                  60
Lys Gly Arg Phe Thr Ile Ser Arg Asp Asn Ala Glu Asn Thr Leu Tyr
65                  70                  75                  80
Leu Gln Met Asn Ser Leu Arg Ala Glu Asp Met Ala Val Tyr Tyr Cys
                85                  90                  95
Ala Arg Asp Trp Ser Tyr Ala Met Asp Val Trp Gly Gln Gly Thr Met
            100                 105                 110
Val Thr Val Ser Ser
        115

<210> SEQ ID NO 23
<211> LENGTH: 108
<212> TYPE: PRT
<213> ORGANISM: Homo sapiens

<400> SEQUENCE: 23

Ser Tyr Val Leu Thr Gln Pro Pro Ser Val Ser Val Ser Pro Gly Gln
1               5                   10                  15
Thr Ala Ser Ile Thr Cys Ser Gly Asp Lys Leu Glu Asp Lys Tyr Ala
```

```
                    20                  25                  30

Cys Trp Tyr Gln Gln Lys Pro Gly Gln Ser Pro Val Leu Val Ile Tyr
            35                  40                  45

His Asp Tyr Lys Arg Pro Ser Gly Ile Pro Glu Arg Phe Ser Gly Ser
 50                  55                  60

Asn Ser Gly Asn Thr Ala Thr Leu Thr Ile Ser Arg Val Glu Gly Gly
 65                  70                  75                  80

Asp Glu Ala Asp Tyr Tyr Cys Gln Val Trp Asp Ser Gly Ser Asp Asp
                    85                  90                  95

Gln Val Phe Gly Gly Gly Thr Lys Leu Thr Val Leu
            100                 105
```

<210> SEQ ID NO 24
<211> LENGTH: 122
<212> TYPE: PRT
<213> ORGANISM: Homo sapiens

<400> SEQUENCE: 24

```
Gln Val Gln Leu Val Gln Ser Gly Ser Asp Val Lys Lys Pro Gly Ala
 1               5                  10                  15

Ser Val Arg Val Ser Cys Lys Val Ser Gly Tyr Arg Leu Thr Glu Tyr
                    20                  25                  30

Pro Ile His Trp Val Arg Gln Ala Pro Gly Lys Gly Leu Glu Tyr Met
            35                  40                  45

Gly Gly Phe Asp Leu Glu Asn Gly Val Thr Lys Ala Ala Pro Arg Phe
 50                  55                  60

Arg Gly Arg Phe Thr Met Thr Glu Asp Thr Ser Thr Asp Ser Val Tyr
 65                  70                  75                  80

Met Glu Leu Lys Ser Leu Thr Ser Glu Asp Thr Ala Val Tyr Tyr Cys
                    85                  90                  95

Val Lys Gly Pro Gly Tyr Gly Ala Leu Val Thr Ser Phe Thr Ser Trp
            100                 105                 110

Gly Leu Gly Thr Thr Val Thr Val Ser Ser
            115                 120
```

<210> SEQ ID NO 25
<211> LENGTH: 108
<212> TYPE: PRT
<213> ORGANISM: Mus musculus

<400> SEQUENCE: 25

```
Asp Ile Val Leu Thr Gln Ser Pro Ala Ile Met Ser Ala Ser Leu Gly
 1               5                  10                  15

Glu Arg Val Thr Met Thr Cys Thr Ala Ser Ser Ser Val Ser Ser Ser
                    20                  25                  30

Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys Arg Gln Tyr His Ser Tyr Pro
                    85                  90                  95

Trp Thr Phe Gly Gly Gly Thr Lys Leu Glu Ile Lys
            100                 105
```

```
<210> SEQ ID NO 26
<211> LENGTH: 118
<212> TYPE: PRT
<213> ORGANISM: Mus musculus

<400> SEQUENCE: 26

Gln Val Gln Leu Gln Gln Ser Gly Pro Glu Leu Val Lys Pro Gly Ala
1               5                   10                  15

Ser Val Glu Met Ser Cys Lys Ala Ser Gly Tyr Thr Phe Thr Ser Tyr
            20                  25                  30

Val Met His Trp Val Lys Gln Lys Pro Gly Gln Asp Leu Glu Trp Ile
        35                  40                  45

Gly Tyr Ile Asn Pro Tyr Ser Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Thr Thr Val Glu Lys Leu Tyr Ser Asp Tyr Trp Gly Gln Gly Thr
            100                 105                 110

Thr Leu Thr Val Ser Ser
        115

<210> SEQ ID NO 27
<211> LENGTH: 16
<212> TYPE: PRT
<213> ORGANISM: Mus musculus

<400> SEQUENCE: 27

Arg Ser Ser Lys Ser Leu Leu Tyr Lys Asp Gly Lys Thr Tyr Leu Tyr
1               5                   10                  15

<210> SEQ ID NO 28
<211> LENGTH: 7
<212> TYPE: PRT
<213> ORGANISM: Mus musculus

<400> SEQUENCE: 28

Leu Met Ser Thr Arg Ala Ser
1               5

<210> SEQ ID NO 29
<211> LENGTH: 9
<212> TYPE: PRT
<213> ORGANISM: Mus musculus

<400> SEQUENCE: 29

Gln Gln Leu Val Glu Tyr Pro Tyr Thr
1               5

<210> SEQ ID NO 30
<211> LENGTH: 15
<212> TYPE: PRT
<213> ORGANISM: Mus musculus

<400> SEQUENCE: 30

Arg Ala Ser Glu Ser Val Asp Ser Tyr Gly Asn Ser Phe Met His
1               5                   10                  15

<210> SEQ ID NO 31
<211> LENGTH: 7
<212> TYPE: PRT
```

```
<213> ORGANISM: Mus musculus

<400> SEQUENCE: 31

Leu Ala Ser Asn Leu Glu Ser
1               5

<210> SEQ ID NO 32
<211> LENGTH: 8
<212> TYPE: PRT
<213> ORGANISM: Mus musculus

<400> SEQUENCE: 32

Gln Gln Asn Asn Glu Glu Leu Thr
1               5

<210> SEQ ID NO 33
<211> LENGTH: 11
<212> TYPE: PRT
<213> ORGANISM: Mus musculus

<400> SEQUENCE: 33

Lys Ala Ser Gln Asp Val Gly Thr Ala Val Ala
1               5                   10

<210> SEQ ID NO 34
<211> LENGTH: 7
<212> TYPE: PRT
<213> ORGANISM: Mus musculus

<400> SEQUENCE: 34

Trp Ala Ser Thr Arg His Thr
1               5

<210> SEQ ID NO 35
<211> LENGTH: 9
<212> TYPE: PRT
<213> ORGANISM: Mus musculus

<400> SEQUENCE: 35

Gln Gln Tyr Cys Ser His Pro Tyr Thr
1               5

<210> SEQ ID NO 36
<211> LENGTH: 11
<212> TYPE: PRT
<213> ORGANISM: Homo sapiens

<400> SEQUENCE: 36

Arg Ala Ser Gln Ala Ile Gly Asn Asp Leu Ala
1               5                   10

<210> SEQ ID NO 37
<211> LENGTH: 7
<212> TYPE: PRT
<213> ORGANISM: Homo sapiens

<400> SEQUENCE: 37

Gly Ala Ser Thr Leu Ser Ser
1               5

<210> SEQ ID NO 38
<211> LENGTH: 9
<212> TYPE: PRT
<213> ORGANISM: Homo sapiens
```

<400> SEQUENCE: 38

Gln Gln Tyr Asn Asn Phe Pro Tyr Thr
1               5

<210> SEQ ID NO 39
<211> LENGTH: 14
<212> TYPE: PRT
<213> ORGANISM: Homo sapiens

<400> SEQUENCE: 39

Thr Gly Ser Ser Ser Asn Ile Gly Ala Gly Tyr Asp Val His
1               5                   10

<210> SEQ ID NO 40
<211> LENGTH: 7
<212> TYPE: PRT
<213> ORGANISM: Homo sapiens

<400> SEQUENCE: 40

Gly Asn Asp Asn Arg Pro Ser
1               5

<210> SEQ ID NO 41
<211> LENGTH: 12
<212> TYPE: PRT
<213> ORGANISM: Homo sapiens

<400> SEQUENCE: 41

Gln Ser Tyr Asp Asn Ser Leu Ser Gly Tyr Ala Val
1               5                   10

<210> SEQ ID NO 42
<211> LENGTH: 11
<212> TYPE: PRT
<213> ORGANISM: Homo sapiens

<400> SEQUENCE: 42

Arg Ala Ser Gln Ser Ile Ser Ser Tyr Leu Asn
1               5                   10

<210> SEQ ID NO 43
<211> LENGTH: 7
<212> TYPE: PRT
<213> ORGANISM: Homo sapiens

<400> SEQUENCE: 43

Ala Ala Ser Ser Leu Gln Ser
1               5

<210> SEQ ID NO 44
<211> LENGTH: 9
<212> TYPE: PRT
<213> ORGANISM: Homo sapiens

<400> SEQUENCE: 44

Gln Gln Ser Tyr Ser Thr Pro Tyr Thr
1               5

<210> SEQ ID NO 45
<211> LENGTH: 14
<212> TYPE: PRT
<213> ORGANISM: Homo sapiens

<400> SEQUENCE: 45

Thr Gly Thr Ser Ser Asp Val Gly Gly Tyr Asn Tyr Val Ser
1               5                   10

<210> SEQ ID NO 46
<211> LENGTH: 7
<212> TYPE: PRT
<213> ORGANISM: Homo sapiens

<400> SEQUENCE: 46

Asp Val Ser Asn Arg Pro Ser
1               5

<210> SEQ ID NO 47
<211> LENGTH: 10
<212> TYPE: PRT
<213> ORGANISM: Homo sapiens

<400> SEQUENCE: 47

Ser Ser Tyr Thr Arg Arg Ser Thr Leu Glu
1               5                   10

<210> SEQ ID NO 48
<211> LENGTH: 11
<212> TYPE: PRT
<213> ORGANISM: Homo sapiens

<400> SEQUENCE: 48

Lys Ala Ser Gln Asp Ile Asp Asp Asp Met Asn
1               5                   10

<210> SEQ ID NO 49
<211> LENGTH: 7
<212> TYPE: PRT
<213> ORGANISM: Homo sapiens

<400> SEQUENCE: 49

Glu Ala Thr Thr Leu Val Pro
1               5

<210> SEQ ID NO 50
<211> LENGTH: 9
<212> TYPE: PRT
<213> ORGANISM: Homo sapiens

<400> SEQUENCE: 50

Pro Gln Gln Asp Asn Val Pro Leu Thr
1               5

<210> SEQ ID NO 51
<211> LENGTH: 12
<212> TYPE: PRT
<213> ORGANISM: Homo sapiens

<400> SEQUENCE: 51

Thr Leu Ser Ser Gly Tyr Ser Asn Tyr Lys Val Asp
1               5                   10

<210> SEQ ID NO 52
<211> LENGTH: 12
<212> TYPE: PRT
<213> ORGANISM: Homo sapiens

<400> SEQUENCE: 52

Val Gly Thr Gly Gly Thr Val Gly Ser Lys Gly Asp
1               5                   10

<210> SEQ ID NO 53
<211> LENGTH: 13
<212> TYPE: PRT
<213> ORGANISM: Homo sapiens

<400> SEQUENCE: 53

Gly Ala Asp His Gly Ser Gly Ser Asn Phe Val Tyr Val
1               5                   10

<210> SEQ ID NO 54
<211> LENGTH: 11
<212> TYPE: PRT
<213> ORGANISM: Homo sapiens

<400> SEQUENCE: 54

Arg Pro Ser Gln Gly Ile Gly Lys Tyr Ser Ala
1               5                   10

<210> SEQ ID NO 55
<211> LENGTH: 7
<212> TYPE: PRT
<213> ORGANISM: Homo sapiens

<400> SEQUENCE: 55

Leu Ala Ser Thr Leu Gln Ser
1               5

<210> SEQ ID NO 56
<211> LENGTH: 9
<212> TYPE: PRT
<213> ORGANISM: Homo sapiens

<400> SEQUENCE: 56

Leu Gln Arg Asn Thr Tyr Pro Trp Thr
1               5

<210> SEQ ID NO 57
<211> LENGTH: 11
<212> TYPE: PRT
<213> ORGANISM: Homo sapiens

<400> SEQUENCE: 57

Ser Gly Asp Lys Leu Glu Asp Lys Tyr Ala Cys
1               5                   10

<210> SEQ ID NO 58
<211> LENGTH: 7
<212> TYPE: PRT
<213> ORGANISM: Homo sapiens

<400> SEQUENCE: 58

His Asp Tyr Lys Arg Pro Ser
1               5

<210> SEQ ID NO 59
<211> LENGTH: 11
<212> TYPE: PRT
<213> ORGANISM: Homo sapiens

<400> SEQUENCE: 59

Gln Val Trp Asp Ser Gly Ser Asp Asp Gln Val
1               5                   10

```
<210> SEQ ID NO 60
<211> LENGTH: 5
<212> TYPE: PRT
<213> ORGANISM: Mus musculus

<400> SEQUENCE: 60

Ser Tyr Trp Met His
1               5

<210> SEQ ID NO 61
<211> LENGTH: 17
<212> TYPE: PRT
<213> ORGANISM: Mus musculus

<400> SEQUENCE: 61

Tyr Ile Asn Pro Ser Thr Gly Tyr Thr Glu Tyr Asn Gln Lys Phe Lys
1               5                   10                  15

Asp

<210> SEQ ID NO 62
<211> LENGTH: 8
<212> TYPE: PRT
<213> ORGANISM: Mus musculus

<400> SEQUENCE: 62

Gly Gly Tyr Asp Asp Leu Gly Tyr
1               5

<210> SEQ ID NO 63
<211> LENGTH: 5
<212> TYPE: PRT
<213> ORGANISM: Mus musculus

<400> SEQUENCE: 63

Arg Tyr Trp Met Ser
1               5

<210> SEQ ID NO 64
<211> LENGTH: 17
<212> TYPE: PRT
<213> ORGANISM: Mus musculus

<400> SEQUENCE: 64

Glu Ile Asn Pro Asp Ser Ser Thr Ile Asn Tyr Thr Pro Ser Leu Lys
1               5                   10                  15

Asp

<210> SEQ ID NO 65
<211> LENGTH: 8
<212> TYPE: PRT
<213> ORGANISM: Mus musculus

<400> SEQUENCE: 65

Arg Ser Tyr Trp Tyr Phe Asp Val
1               5

<210> SEQ ID NO 66
<211> LENGTH: 5
<212> TYPE: PRT
<213> ORGANISM: Mus musculus

<400> SEQUENCE: 66

Asp Thr Tyr Met His
1               5
```

<210> SEQ ID NO 67
<211> LENGTH: 17
<212> TYPE: PRT
<213> ORGANISM: Mus musculus

<400> SEQUENCE: 67

Arg Ile Asp Pro Ala His Gly Arg Thr Lys Tyr Asp Pro Lys Phe Gln
1               5                   10                  15

Gly

<210> SEQ ID NO 68
<211> LENGTH: 7
<212> TYPE: PRT
<213> ORGANISM: Mus musculus

<400> SEQUENCE: 68

Tyr Ser Tyr Ala Ile Asp Tyr
1               5

<210> SEQ ID NO 69
<211> LENGTH: 5
<212> TYPE: PRT
<213> ORGANISM: Homo sapiens

<400> SEQUENCE: 69

Gly Asn Phe Trp Ser
1               5

<210> SEQ ID NO 70
<211> LENGTH: 16
<212> TYPE: PRT
<213> ORGANISM: Homo sapiens

<400> SEQUENCE: 70

Glu Val Asn His Arg Gly Ser Ala Thr Tyr Asn Pro Ser Leu Lys Ser
1               5                   10                  15

<210> SEQ ID NO 71
<211> LENGTH: 19
<212> TYPE: PRT
<213> ORGANISM: Homo sapiens

<400> SEQUENCE: 71

Lys Leu Pro Arg Arg Arg Ala Glu Asp Arg Pro Ser Ser Leu Arg Pro
1               5                   10                  15

Phe Asp Tyr

<210> SEQ ID NO 72
<211> LENGTH: 5
<212> TYPE: PRT
<213> ORGANISM: Homo sapiens

<400> SEQUENCE: 72

Ser His Asp Met His
1               5

<210> SEQ ID NO 73
<211> LENGTH: 16
<212> TYPE: PRT
<213> ORGANISM: Homo sapiens

<400> SEQUENCE: 73

-continued

Arg Ile Gly Thr Val Gly Asp Thr Tyr Tyr Ala Asp Ser Val Lys Gly
1               5                   10                  15

<210> SEQ ID NO 74
<211> LENGTH: 22
<212> TYPE: PRT
<213> ORGANISM: Homo sapiens

<400> SEQUENCE: 74

Asp Gly Thr Arg Tyr Cys Ser Arg Thr Ser Cys His Ser Gly Tyr Tyr
1               5                   10                  15

Tyr Tyr Gly Met Asp Val
            20

<210> SEQ ID NO 75
<211> LENGTH: 5
<212> TYPE: PRT
<213> ORGANISM: Homo sapiens

<400> SEQUENCE: 75

Asp His Tyr Met Asp
1               5

<210> SEQ ID NO 76
<211> LENGTH: 19
<212> TYPE: PRT
<213> ORGANISM: Homo sapiens

<400> SEQUENCE: 76

Arg Ile Arg Asn Lys Ala Asn Ser Tyr Thr Thr Glu Tyr Ala Ala Ser
1               5                   10                  15

Val Lys Gly

<210> SEQ ID NO 77
<211> LENGTH: 10
<212> TYPE: PRT
<213> ORGANISM: Homo sapiens

<400> SEQUENCE: 77

Asp Leu Gly Ala Ser Asp Ala Phe Gly Leu
1               5                   10

<210> SEQ ID NO 78
<211> LENGTH: 5
<212> TYPE: PRT
<213> ORGANISM: Homo sapiens

<400> SEQUENCE: 78

Gly Tyr Tyr Trp Ser
1               5

<210> SEQ ID NO 79
<211> LENGTH: 16
<212> TYPE: PRT
<213> ORGANISM: Homo sapiens

<400> SEQUENCE: 79

Glu Ile Asn His Ser Gly Ser Thr Asn Tyr Asn Pro Ser Leu Lys Ser
1               5                   10                  15

<210> SEQ ID NO 80
<211> LENGTH: 21
<212> TYPE: PRT
<213> ORGANISM: Homo sapiens

```
<400> SEQUENCE: 80

Thr Ile Trp Ser Thr Arg His Asp Phe Trp Ser Gly Tyr Tyr Ser Ser
1               5                   10                  15

Asn Trp Phe Asp Pro
            20

<210> SEQ ID NO 81
<211> LENGTH: 5
<212> TYPE: PRT
<213> ORGANISM: Homo sapiens

<400> SEQUENCE: 81

Glu Tyr Pro Ile His
1               5

<210> SEQ ID NO 82
<211> LENGTH: 17
<212> TYPE: PRT
<213> ORGANISM: Homo sapiens

<400> SEQUENCE: 82

Gly Phe Asp Leu Glu Asn Gly Val Thr Lys Ala Ala Pro Arg Phe Arg
1               5                   10                  15

Gly

<210> SEQ ID NO 83
<211> LENGTH: 13
<212> TYPE: PRT
<213> ORGANISM: Homo sapiens

<400> SEQUENCE: 83

Gly Pro Gly Tyr Gly Ala Leu Val Thr Ser Phe Thr Ser
1               5                   10

<210> SEQ ID NO 84
<211> LENGTH: 5
<212> TYPE: PRT
<213> ORGANISM: Homo sapiens

<400> SEQUENCE: 84

Ser Tyr Ala Met Thr
1               5

<210> SEQ ID NO 85
<211> LENGTH: 17
<212> TYPE: PRT
<213> ORGANISM: Homo sapiens

<400> SEQUENCE: 85

Ala Ile Ser Gly Ser Gly Asp Ser Thr Tyr Tyr Ala Asp Ser Val Lys
1               5                   10                  15

Gly

<210> SEQ ID NO 86
<211> LENGTH: 12
<212> TYPE: PRT
<213> ORGANISM: Homo sapiens

<400> SEQUENCE: 86

Asp Arg Asp Leu Leu His Lys Asp Gly Phe Asp Ile
1               5                   10
```

<210> SEQ ID NO 87
<211> LENGTH: 5
<212> TYPE: PRT
<213> ORGANISM: Homo sapiens

<400> SEQUENCE: 87

Gly Tyr Gly Met Asn
1               5

<210> SEQ ID NO 88
<211> LENGTH: 17
<212> TYPE: PRT
<213> ORGANISM: Homo sapiens

<400> SEQUENCE: 88

Thr Ile Ser Phe Asp Gly Thr Asp Lys Tyr Tyr Ala Asp Ser Val Lys
1               5                   10                  15

Gly

<210> SEQ ID NO 89
<211> LENGTH: 8
<212> TYPE: PRT
<213> ORGANISM: Homo sapiens

<400> SEQUENCE: 89

Asp Trp Ser Tyr Ala Met Asp Val
1               5

<210> SEQ ID NO 90
<211> LENGTH: 5
<212> TYPE: PRT
<213> ORGANISM: Homo sapiens

<400> SEQUENCE: 90

Glu Tyr Pro Ile His
1               5

<210> SEQ ID NO 91
<211> LENGTH: 17
<212> TYPE: PRT
<213> ORGANISM: Homo sapiens

<400> SEQUENCE: 91

Gly Phe Asp Leu Glu Asn Gly Val Thr Lys Ala Ala Pro Arg Phe Arg
1               5                   10                  15

Gly

<210> SEQ ID NO 92
<211> LENGTH: 13
<212> TYPE: PRT
<213> ORGANISM: Homo sapiens

<400> SEQUENCE: 92

Gly Pro Gly Tyr Gly Ala Leu Val Thr Ser Phe Thr Ser
1               5                   10

<210> SEQ ID NO 93
<211> LENGTH: 352
<212> TYPE: PRT
<213> ORGANISM: Artificial Sequence
<220> FEATURE:
<223> OTHER INFORMATION: synthetic sequence

<400> SEQUENCE: 93

Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
                20                  25                  30

Gln Arg Leu Gly Phe Arg Ser Pro Asn Ala Ala Glu Glu His Leu Lys
            35                  40                  45

Ala Leu Ala Arg Lys Gly Val Ile Glu Ile Val Ser Gly Ala Ser Arg
        50                  55                  60

Gly Ile Arg Leu Leu Gln Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Thr Lys Ile Val
        195                 200                 205

Gly Thr Phe Asn Lys Lys Ser Lys Gly Tyr Thr Asp Val Val Arg Ile
    210                 215                 220

Pro Glu Gly Ala Thr His Ile Lys Val Arg Gln Phe Lys Ala Lys Asp
225                 230                 235                 240

Gln Thr Arg Phe Thr Ala Tyr Leu Ala Leu Lys Lys Asn Gly Glu
                245                 250                 255

Tyr Leu Ile Asn Gly Lys Tyr Met Ile Ser Thr Ser Glu Thr Ile Ile
            260                 265                 270

Asp Ile Asn Gly Thr Val Met Asn Tyr Ser Gly Trp Ser His Arg Asp
        275                 280                 285

Asp Phe Leu His Gly Met Gly Tyr Ser Ala Thr Lys Glu Ile Leu Ile
    290                 295                 300

Val Gln Ile Leu Ala Thr Asp Pro Thr Lys Pro Leu Asp Val Arg Tyr
305                 310                 315                 320

Ser Phe Phe Val Pro Lys Lys Ser Thr Pro Lys Val Asn Ser Val Thr
                325                 330                 335

Ser His Gly Ser Asn Lys Val Gly Ser His Thr Lys Ile Tyr Ala Ile
            340                 345                 350

<210> SEQ ID NO 94
<211> LENGTH: 424
<212> TYPE: PRT
<213> ORGANISM: Artificial Sequence
<220> FEATURE:
<223> OTHER INFORMATION: synthetic sequence

<400> SEQUENCE: 94

Met Ser Pro Ile Leu Gly Tyr Trp Lys Ile Lys Gly Leu Val Gln Pro
1               5                   10                  15

```
Thr Arg Leu Leu Leu Glu Tyr Leu Glu Glu Lys Tyr Glu Glu His Leu
         20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Ile Asp Gly Asp Val Lys
 50                  55                  60

Leu Thr Gln Ser Met Ala Ile Ile Arg Tyr Ile Ala Asp Lys His Asn
65                   70                  75                  80

Met Leu Gly Gly Cys Pro Lys Glu Arg Ala Glu Ile Ser Met Leu Glu
             85                  90                  95

Gly Ala Val Leu Asp Ile Arg Tyr Gly Val Ser Arg Ile Ala Tyr Ser
             100                 105                 110

Lys Asp Phe Glu Thr Leu Lys Val Asp Phe Leu Ser Lys Leu Pro Glu
         115                 120                 125

Met Leu Lys Met Phe Glu Asp Arg Leu Cys His Lys Thr Tyr Leu Asn
 130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
             165                 170                 175

Val Cys Phe Lys Lys Arg Ile Glu Ala Ile Pro Gln Ile Asp Lys Tyr
             180                 185                 190

Leu Lys Ser Ser Lys Tyr Ile Ala Trp Pro Leu Gln Gly Trp Gln Ala
         195                 200                 205

Thr Phe Gly Gly Gly Asp His Pro Pro Lys Ser Asp Gly Ser Thr Ser
 210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
             245                 250                 255

Arg Gln His Met Asp Ser Pro Asp Leu Gly Thr Gly Gly Gly Ser Gly
             260                 265                 270

Asp Asp Asp Asp Lys Ser Pro Met Val Thr Lys Ile Val Gly Thr Phe
         275                 280                 285

Asn Lys Lys Ser Lys Gly Tyr Thr Asp Val Val Arg Ile Pro Glu Gly
 290                 295                 300

Ala Thr His Ile Lys Val Arg Gln Phe Lys Ala Lys Asp Gln Thr Arg
305                 310                 315                 320

Phe Thr Ala Tyr Leu Ala Leu Lys Lys Lys Asn Gly Glu Tyr Leu Ile
             325                 330                 335

Asn Gly Lys Tyr Met Ile Ser Thr Ser Glu Thr Ile Ile Asp Ile Asn
             340                 345                 350

Gly Thr Val Met Asn Tyr Ser Gly Trp Ser His Arg Asp Asp Phe Leu
         355                 360                 365

His Gly Met Gly Tyr Ser Ala Thr Lys Glu Ile Leu Ile Val Gln Ile
 370                 375                 380

Leu Ala Thr Asp Pro Thr Lys Pro Leu Asp Val Arg Tyr Ser Phe Phe
385                 390                 395                 400

Val Pro Lys Lys Ser Thr Pro Lys Val Asn Ser Val Thr Ser His Gly
             405                 410                 415

Ser Asn Lys Val Gly Ser His Thr
         420
```

<210> SEQ ID NO 95
<211> LENGTH: 708
<212> TYPE: DNA
<213> ORGANISM: Homo sapiens

<400> SEQUENCE: 95

| | | | | | |
|---|---|---|---|---|---|
| atggaatggt | ccggcgtgtt | catgttcctg | ctgtccgtga | ccgctggcgt | gcactccgac | 60 |
| atcgtgctga | cccagtcccc | cgccatcatg | tctgcctccc | tgggcgagcg | cgtgacaatg | 120 |
| acctgcaccg | cctcctccag | cgtgtcctcc | tcctacctgc | actggtatca | gcagaagccc | 180 |
| ggctccagcc | ccaagctgtg | gatctactcc | acctccaacc | tggcctccgg | cgtgcccgcc | 240 |
| agattctctg | gctccggctc | cggcacctcc | tactccctga | ccatctccag | catggaagcc | 300 |
| gaggacgccg | ccacctacta | ctgtcggcag | taccactcct | accccctggac | cttcggcgga | 360 |
| ggcaccaagc | tggaaatcaa | gcggaccgtg | gccgctccct | ccgtgttcat | cttcccaccc | 420 |
| tccgacgagc | agctgaagtc | cggcaccgcc | agcgtcgtgt | gcctgctgaa | caacttctac | 480 |
| ccccgcgagg | ccaaggtgca | gtggaaggtg | gacaacgccc | tgcagtccgg | caactcccag | 540 |
| gaatccgtca | ccgagcagga | ctccaaggac | agcacctaca | gcctgagttc | caccctgacc | 600 |
| ctgtccaagg | ccgactacga | aagcacaag | gtgtacgcct | gcgaagtgac | ccaccagggc | 660 |
| ctgtccagcc | ccgtgaccaa | gtccttcaac | cggggcgagt | gctgataa | | 708 |

<210> SEQ ID NO 96
<211> LENGTH: 1398
<212> TYPE: DNA
<213> ORGANISM: Homo sapiens

<400> SEQUENCE: 96

| | | | | | |
|---|---|---|---|---|---|
| atggaatggt | ccggcgtgtt | catgttcctg | ctgtccgtga | ccgctggcgt | gcactcccag | 60 |
| gtgcagctgc | agcagtccgg | ccctgagctg | gtcaagcctg | gcgcctccgt | ggaaatgtcc | 120 |
| tgcaaggcct | ccggctacac | cttcaccagc | tacgtgatgc | actgggtcaa | gcagaagccc | 180 |
| ggccaggacc | tggaatggat | cggctacatc | aaccccatact | ccgacggcac | caagtacaac | 240 |
| gagaagttca | agggcaaggc | caccctgacc | tccgacaagt | cctcctccac | cgcctacatg | 300 |
| gaactgtcct | ccctgaccag | cgaggactcc | gccgtgtact | actgcgccac | caccgtggaa | 360 |
| aagctgtact | ccgactactg | gggccagggc | accacactga | ccgtgtcctc | tgcctccacc | 420 |
| aagggccctt | ccgtgttccc | tctggcccct | gctcccggt | ccacctctga | gtctaccgcc | 480 |
| gctctgggct | gcctggtgaa | agactacttc | cccgagcccg | tgaccgtgtc | ctggaactcc | 540 |
| ggcgctctga | cctccggcgt | gcacaccttc | cctgccgtgc | tgcagtccag | cggcctgtac | 600 |
| tccctgtcct | ccgtggtgac | cgtgccttcc | tccagcctgg | gcaccaagac | ctacacctgt | 660 |
| aacgtggacc | acaagccctc | caacaccaag | gtggacaagc | gggtggaatc | taagtacggc | 720 |
| ccaccctgcc | cccctgccc | tgctcctgag | tttctgggcg | gacccctccgt | gttcctgttc | 780 |
| cccccaaagc | ccaaggatac | cctgatgatc | tcccggaccc | ccgaagtgac | ctgcgtggtg | 840 |
| gtggacgtgt | cccaggaaga | tcccgaggtc | cagttcaatt | ggtacgtgga | cggcgtggaa | 900 |
| gtgcacaacg | ccaagaccaa | gcccagagag | gaacagttca | actccaccta | ccgggtggtg | 960 |
| tctgtgctga | cagtgctgca | tcaggactgg | ctgaacggca | aagagtacaa | gtgcaaagtc | 1020 |
| tccaacaagg | gactgcctc | cagcatcgaa | aagaccatct | ccaaggccaa | gggccagccc | 1080 |
| cgcgagcctc | aggtgtacac | cctgccacct | agccaggaag | agatgaccaa | gaaccaggtg | 1140 |
| tccctgacct | gtctggtgaa | aggcttctac | ccctccgaca | tcgccgtgga | atgggagtct | 1200 |

```
aacggccagc ccgagaacaa ctacaagacc acacccctg tgctggactc cgacggctcc    1260
ttcttcctgt actctcggct gacagtggac aagtcccggt ggcaggaagg caacgtcttc    1320
tcctgctccg tgatgcacga ggccctgcac aaccactaca cccagaagtc cctgtccctg    1380
agcctgggca agtgataa                                                  1398

<210> SEQ ID NO 97
<211> LENGTH: 720
<212> TYPE: DNA
<213> ORGANISM: Homo sapiens

<400> SEQUENCE: 97
atggaatggt ccggcgtgtt catgttcctg ctgtccgtga ccgctggcgt gcactccgac      60
atcgtgatca cccaggacga gctgtccaac cccgtgacct ccggcgagtc cgtgtccatc     120
tcctgccggt cctccaagtc cctgctgtac aaggacggca agacctacct gtactggttc     180
ctgcagcggc ctggccagtc ccccagctg cccatctacc tgatgtccac ccgggccagc     240
ggcgtgtccg acagattctc cggctccggc agcggcaccg actttaccct ggaaatctcc     300
agagtgaagg ccgaggacgt gggcgtgtac tactgccagc agctggtgga atacccctac     360
accttcggcg gaggcaccaa gctggaaatc aagcggaccg tggccgctcc ctccgtgttc     420
atcttcccac cctccgacga gcagctgaag tccggcaccg cctccgtcgt gtgcctgctg     480
aacaacttct acccccgcga ggccaaggtg cagtggaagg tggacaacgc cctgcagtcc     540
ggcaactccc aggaatccgt caccgagcag gactccaagg acagcaccta ctccctgtcc     600
tccaccctga ccctgtccaa ggccgactac gagaagcaca aggtgtacgc ctgcgaagtg     660
acccaccagg gcctgtccag ccctgtgacc aagtccttca accggggcga gtgctgataa     720

<210> SEQ ID NO 98
<211> LENGTH: 1393
<212> TYPE: DNA
<213> ORGANISM: Homo sapiens

<400> SEQUENCE: 98
atggaatggt ccggcgtgtt catgttcctg ctgtccgtga ccgctggcgt gcactccag      60 gtgcagctgc agcagtctgg cgccgagctg gctaagcctg gcgcctccgt gaagatgtcc    120
tgcaaggcct ccggctacac cttcaccagc tactggatgc actgggtcaa gcagcggcct    180
ggccagggcc tggaatggat cggctacatc aacccctcca ccggctatac cgagtacaac    240
cagaagttca aggacaaggc caccctgacc gccgacaagt cctcctccac cgcctacatg    300
cagctgggct ccctgacctc cgaggactcc gccgtgtact actgcgccag aggcggctac    360
gacgacctgg atactgggg ccagggcacc acactgaccg tgtcctctgc ctccaccaag    420
ggcccttccg tgttcccctct ggccccttgc tcccggtcca cctctgagtc taccgccgct    480
ctgggctgcc tggtgaaaga ctacttcccc gagcccgtga ccgtgtcctg gaactccggc    540
gctctgacct ccggcgtgca caccttccct gccgtgctgc agtccagcgg cctgtactcc    600
ctgtcctccg tggtgaccgt gccttcctcc agcctgggca ccaagaccta cacctgtaac    660
gtggaccaca agccctccaa caccaaggtg gacaagcggg tggaatctaa gtacggccca    720
ccctgccccc cctgccctgc tcctgagttt ctgggcggac cctccgtgtt cctgttcccc    780
ccaaagccca aggatacct gatgatctcc cggacccccg aagtgacctg cgtggtggtg    840
gacgtgtccc aggaagatcc cgaggtccag ttcaattggt acgtggacgg cgtggaagtg    900
```

| | |
|---|---|
| cacaacgcca agaccaagcc cagagaggaa cagttcaact ccacctaccg ggtggtgtct | 960 |
| gtgctgacag tgctgcatca ggactggctg aacggcaaag agtacaagtg caaagtctcc | 1020 |
| aacaagggac tgccctccag catcgaaaag accatctcca aggccaaggg ccagccccgc | 1080 |
| gagcctcagg tgtacaccct gccacctagc caggaagaga tgaccaagaa ccaggtgtcc | 1140 |
| ctgacctgtc tggtgaaagg cttctacccc tccgacatcg ccgtggaatg ggagtctaac | 1200 |
| ggccagcccg agaacaacta caagaccaca cccctgtgc tggactccga cggctccttc | 1260 |
| ttcctgtact ctcggctgac agtggacaag tcccggtggc aggaaggcaa cgtcttctcc | 1320 |
| tgctccgtga tgcacgaggc cctgcacaac cactacaccc agaagtccct gtccctgagc | 1380 |
| ctgggcaagt gat | 1393 |

<210> SEQ ID NO 99
<211> LENGTH: 336
<212> TYPE: DNA
<213> ORGANISM: Homo sapiens

<400> SEQUENCE: 99

| | |
|---|---|
| gacattgtga taactcagga tgaactctcc aatcctgtca cttctggaga atcagtttcc | 60 |
| atctcctgca ggtctagtaa gagtctccta tataaggatg gaagacata cttgtattgg | 120 |
| tttctgcaga gaccaggaca atctcctcag ctcccgatct atttgatgtc cacccgtgca | 180 |
| tcaggagtct cagaccggtt tagtggcagt gggtcaggaa cagatttcac cctgaaaatc | 240 |
| agtagagtga aggctgagga tgtgggtgtg tattactgtc aacaacttgt agagtatccg | 300 |
| tacacgttcg agggggggac caagctggaa atcaaa | 336 |

<210> SEQ ID NO 100
<211> LENGTH: 351
<212> TYPE: DNA
<213> ORGANISM: Homo sapiens

<400> SEQUENCE: 100

| | |
|---|---|
| caggttcagc tgcagcagtc tggggctgag ctggcaaaac ctggggcctc agtgaagatg | 60 |
| tcctgcaagg cttctggcta cacctttact agctactgga tgcactgggt aaaacagagg | 120 |
| cctggacagg gtctggaatg gattggatac attaatccta gcactggtta tactgagtac | 180 |
| aatcagaagt tcaaggacaa ggccacattg actgcagaca atcctccag cacagcctac | 240 |
| atgcaactgg gcagcctgac atctgaggac tctgcagtct attactgtgc aagagggggg | 300 |
| tatgatgatc ttggctactg gggccaaggc accactctca cagtctcctc a | 351 |

<210> SEQ ID NO 101
<211> LENGTH: 330
<212> TYPE: DNA
<213> ORGANISM: Homo sapiens

<400> SEQUENCE: 101

| | |
|---|---|
| gacattgtga tgacccaatc tccagcttct ttggctgtgt ctcaagggca gagggccacc | 60 |
| atatcctgca gagccagtga agtgttgat agttatggca atagttttat gcactggtac | 120 |
| cagcagaaac caggacagcc acccaaactc cccatctatc ttgcttccaa cctagaatct | 180 |
| ggggtccctg ccaggttcag tggcagtggg tctaggacag acttcaccct caccattgat | 240 |
| cctgtggagg ctgatgatgc tgcaacctat tactgtcagc aaaataatga ggagctcacg | 300 |
| ttcggtgctg ggaccaagct ggagctgaaa | 330 |

<210> SEQ ID NO 102
<211> LENGTH: 351
<212> TYPE: DNA
<213> ORGANISM: Homo sapiens

<400> SEQUENCE: 102

| | | | | | |
|---|---|---|---|---|---|
| gaagtgaagc | ttctcgagtc | tggaggtggc | ctggtgcagc | ctggaggatc | cctgaaactc | 60 |
| tcctgtacaa | cctcaggatt | cgactttagt | agatactgga | tgagttgggt | ccggcaggct | 120 |
| ccagggaaag | ggctagaatg | gattggagaa | attaatccag | atagcagtac | gataaactat | 180 |
| acgccatctc | taaaggataa | attcatcatc | tccagagaca | acgccaaaaa | tacgctgtac | 240 |
| ctgcaaatga | gcaaagtgag | atctgaggac | acagcccttt | attactgtgc | aagaaggagc | 300 |
| tactggtact | tcgatgtctg | gggcgcaggg | acctcagtca | ccgtctcctc | a | 351 |

<210> SEQ ID NO 103
<211> LENGTH: 321
<212> TYPE: DNA
<213> ORGANISM: Homo sapiens

<400> SEQUENCE: 103

| | | | | | |
|---|---|---|---|---|---|
| gacattgtga | tgacacagtc | tcacaaattc | atgtccacat | cagaaggaga | cagggtcagc | 60 |
| atcacctgca | aggccagtca | ggatgtgggt | actgctgtag | cctggtatca | acagaaacca | 120 |
| ggccaatctc | ctaaactact | gatttactgg | gcatccaccc | ggcacactgg | agtccctgat | 180 |
| cgcttcacag | gcagtggatc | tgggacagat | ttcactctca | ccattagcaa | tgtgcagtct | 240 |
| gaagacttgg | cagattatat | ctgtcagcaa | tattgcagcc | atccgtacac | gttcggtgct | 300 |
| gggaccaagc | tggaaatcaa | a | | | | 321 |

<210> SEQ ID NO 104
<211> LENGTH: 348
<212> TYPE: DNA
<213> ORGANISM: Homo sapiens

<400> SEQUENCE: 104

| | | | | | |
|---|---|---|---|---|---|
| caagttcagc | tgcagcagtc | tggggcagaa | cctgtgaagc | caggggcctc | agtcaagttg | 60 |
| tcctgcacag | cttctggctt | caacattaaa | gacacctata | tgcactgggt | gaaacagagg | 120 |
| cctgaacagg | gcctggaatg | gattggaagg | attgatcctg | cgcatggcag | aactaaatat | 180 |
| gacccgaagt | tccagggcaa | ggccactata | acagcagaca | catcctccaa | cacagcctac | 240 |
| ctgcaactca | gcagcctgtc | atctgaggac | actgccgtct | attactgtgc | tttttactcc | 300 |
| tatgctattg | actactgggg | tcagggaacc | tcagtcaccg | tctcctca | | 348 |

<210> SEQ ID NO 105
<211> LENGTH: 321
<212> TYPE: DNA
<213> ORGANISM: Homo sapiens

<400> SEQUENCE: 105

| | | | | | |
|---|---|---|---|---|---|
| gatattgtga | tgactcagtc | tccatcctcc | ctgtctgcat | ctgtaggaga | cagagtcacc | 60 |
| atcacttgcc | gggcaagtca | ggccattggc | aatgatttag | cctggtatca | gcagagacca | 120 |
| gggaaagccc | ctaagcgcct | gatctatggt | gcatccactt | tgtccagtgg | ggtcccatca | 180 |
| cgattcagcg | gcagtggatc | tgggacagaa | ttcactctca | ccatcagcag | cctgcagcct | 240 |
| gatgattttg | caacttatta | ctgccaacaa | tataataatt | tcccctacac | ttttggcctg | 300 |
| gggaccaagg | tggaaatcaa | a | | | | 321 |

<210> SEQ ID NO 106
<211> LENGTH: 381
<212> TYPE: DNA
<213> ORGANISM: Homo sapiens

<400> SEQUENCE: 106
caggtgcagc tacagcagtg gggcgcaggg ctgttgaagc cctcggagac cctgtccctc    60
acctgcgctg tgcatggtgg gtccttcagt ggtaacttct ggagctgggt ccgccaacac   120
ccagggaagg gactggagtg gatcggggaa gtcaatcatc gtggaagcgc cacctacaac   180
ccgtcactca agagtcgagt caccatgtca gttgacacat ccaagaatca gttctccctg   240
caattgagct ctgtgaccgc cgcggacacg gctgtctatt actgtgcgag aaagcttcca   300
agacgacggg cggaggaccg accctcgagt ttacggccgt ttgactactg gggccaggga   360
accctggtca ccgtctcctc a                                             381

<210> SEQ ID NO 107
<211> LENGTH: 336
<212> TYPE: DNA
<213> ORGANISM: Homo sapiens

<400> SEQUENCE: 107
cagtctgtcg tgacgcagcc gccctcagtg tctggggccc cagggcagag ggtcaccatc    60
tcctgcactg ggagcagctc caacatcggg gcaggttatg atgtacactg gtaccagcag   120
cttccaggaa cagcccccaa actcctcatc tatggtaatg acaatcggcc ctcaggggtc   180
cctgaccgat tctctggctc caagtctggc acctcagcct ccctggccat cactgggctc   240
caggctgagg atgaggctga ttattactgc cagtcctatg acaacagcct gagtggctat   300
gctgtgttcg gaggaggcac ccagctgacc gtcctc                             336

<210> SEQ ID NO 108
<211> LENGTH: 390
<212> TYPE: DNA
<213> ORGANISM: Homo sapiens

<400> SEQUENCE: 108
caggtgcagc tggtggagtc tgggggaggc ttggtacagc ctggggggtc cctgagactc    60
tcctgtgcag cctctggatt caggttctcc agccacgaca tgcactgggt ccgccaagtt   120
ccaggaaaag gtctggagtg ggtctcacgt attgggactg ttggtgacac atactacgca   180
gactccgtga agggccggtt caccatctcc agagacaatt ccaagaacac gctgtttctg   240
caaatgaaca gcctgggagc cgaggacacg gccgtgtatt actgtgcgag agatggtacc   300
cgttattgta gtagaaccag ctgccacagc ggctactact actacggtat ggacgtctgg   360
ggccaaggga ccacggtcac cgtctcctca                                    390

<210> SEQ ID NO 109
<211> LENGTH: 321
<212> TYPE: DNA
<213> ORGANISM: Homo sapiens

<400> SEQUENCE: 109
gatattgtga tgacccagac tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240

```
gaagattttg caacttacta ctgtcaacag agttacagta ccccgtacac ttttggccag    300
gggaccaagg tggaaatcaa a                                              321
```

<210> SEQ ID NO 110
<211> LENGTH: 363
<212> TYPE: DNA
<213> ORGANISM: Homo sapiens

<400> SEQUENCE: 110

```
caggtgcagc tggtgcagtc tgggggaggc ttggtcaagc ctggagggtc cctgagactc    60
tcctgtgcag cctccggatt caccttcagt gaccactaca tggactgggt ccgccaggct    120
ccagggaagg ggctggagtg ggttggccgt attagaaaca agctaacagt tacaccaca    180 gaatacgccg cgtctgtgaa aggcagattc accatctcaa gagatgattc aaagaaaaca    240
ctgtatctgc aaatgaccag cctgaaaacc gacgacacgg ccctttatta ttgtgctaga    300
gatctggggg cctctgatgc ttttggtctc tggggccaag ggaccacggt caccgtctcc    360
tca                                                                  363
```

<210> SEQ ID NO 111
<211> LENGTH: 330
<212> TYPE: DNA
<213> ORGANISM: Homo sapiens

<400> SEQUENCE: 111

```
cagtctgtct tgacgcagcc gccctccgcg tccgggtctc ctggacagtc agtcaccatc    60
tcctgcactg gaaccagcag tgacgttggt ggttataact atgtctcctg gtaccaacaa    120
cacccaggca aagcccccaa actcttgatt tatgatgtca gtaatcggcc ctcagggggtt   180 tctagtcgct tctctggctc caagtctggc aactcggcct ccctgaccat ctctgggctc    240
caggctgagg acgaggctga ttattactgc agctcatata caagaaggag cactctggag    300
ttcggcggag ggaccaagct gaccgtccta                                     330
```

<210> SEQ ID NO 112
<211> LENGTH: 387
<212> TYPE: DNA
<213> ORGANISM: Homo sapiens

<400> SEQUENCE: 112

```
caggtgcagc tacagcagtg gggcgcagga ctgttgaagc cttcggggac cctgtccctc    60
acctgcgctg tctatggtgg gtccttcagt ggttactact ggagctggat ccgccagccc    120
ccagggaagg ggctggagtg gattgggggaa atcaatcata gtggaagcac caactacaac    180
ccgtccctca agagtcgagt caccatatca gtagacacgt ccaagaacca gttctccctg    240
aagctgagct ctgtgaccgc cgcggacacg gctgtgtatt actgtgcgag aaccatatgg    300
agcacccgac acgattttg gagtggttat tattcctcca actggttcga cccctggggc    360
cagggaaccc tggtcaccgt ctcctca                                        387
```

<210> SEQ ID NO 113
<211> LENGTH: 321
<212> TYPE: DNA
<213> ORGANISM: Homo sapiens

<400> SEQUENCE: 113

```
gaaacgacac tcacgcagtc tccagcattc atgtcggcga ctccaggaga caaaatctat    60
```

```
atctcctgca aagccagcca agacattgat gatgatatga actggtacca acagaaacca      120
ggagaagctg ctattttcat tattcaagaa gctactactc tcgttcctgg aatcccacct      180
cgattcagtg gcagcgggta tggaacagat tttaccctca caattaataa catggaatct      240
gaggatgctg catattactt ctgtccacaa caagataatg tcccctcac tttcggcgga       300 gggaccaagg tggatatcaa a                                                321
```

<210> SEQ ID NO 114
<211> LENGTH: 366
<212> TYPE: DNA
<213> ORGANISM: Homo sapiens

<400> SEQUENCE: 114

```
gaggtgcagc tggtggagtc tgggtctgac gtgaagaagc cggggggcctc agtgagggtc     60 tcctgcaaag tttccggata cagactcact gagtatccca tacactgggt tcgacaggcg     120
ccggggaaag gacttgagta catgggaggc tttgatcttg aaaatggtgt aacaaaggcc     180
gcaccgaggt tcaggggcag attcaccatg accgaggaca catctacaga ctctgtttat     240
atggagttga gagcctgac atctgaagac acggccgtct attattgtgt aaaggggccg      300
ggatacggtg cgttggtgac ctcctttacc tcctggggcc tgggaaccct ggtcaccgtc     360
tcctca                                                                 366
```

<210> SEQ ID NO 115
<211> LENGTH: 348
<212> TYPE: DNA
<213> ORGANISM: Homo sapiens

<400> SEQUENCE: 115

```
cagtctgtgt tgacgcagcc gccttctgca tcagcctccc tgggagcctc ggtcacactc      60
acctgcaccc tgagcagcgg ctacagtaat tataaagtgg actggtacca acagacacca     120
gggaagggcc cccggtttgt gatgcgagtg ggcactggtg ggactgtggg atccaagggg     180
gatggcatcc ctgatcgctt ctcagtcttg ggctcaggcc tgaatcggta cctgatcatc     240
aagaacatcc aggaagagga tgagactgac taccactgtg gggcagacca tggcagtggg     300
agcaacttcg tgtatgtctt cggaagtggg accaaggtca ccgtcccta                 348
```

<210> SEQ ID NO 116
<211> LENGTH: 363
<212> TYPE: DNA
<213> ORGANISM: Homo sapiens

<400> SEQUENCE: 116

```
caggtgcagc tgcaggagtc ggggggaggc ttggtacggc ctgggggggtc cctgagactc      60 tcctgtgcag cctctggatt caccttttagc agctatgcca tgacctgggt ccgccaggct    120
ccagggaagg gctggagtg gtctcagct attagtggta gtggtgatag cacatactac       180
gcagactccg tgaagggccg gttcaccatc tccagagaca attccaagaa cacgctgtat     240
ctgcaaatgg acagcctgag agtcgaggac acggctgtgt attactgtgc gagagatcgc    300
gatctcctgc acaaagatgg ttttgatatc tggggccaag gacaatggt caccgtctct     360 tca                                                                    363
```

<210> SEQ ID NO 117
<211> LENGTH: 321
<212> TYPE: DNA
<213> ORGANISM: Homo sapiens

<400> SEQUENCE: 117

```
gacatccaga tgacccagtc tccatcttcc gtgtctgcat ctgttggaga cagagtcacc     60
atcacttgtc ggccgagtca gggaattggc aagtactcag cctggtatca gcagaaacca    120
gggaaagccc ctgagctccc gatctatctt gcatccactt tgcaaagtgg ggtcccatca    180
aggttcagcg acagtggatc tgggacagaa ttcactctca caatcagcag cctgcagcct    240
gaagattttg caacttatta ctgtctacag cgtaatactt acccgtggac gttcggccaa    300
gggaccaagg tggaaatcaa a                                              321
```

<210> SEQ ID NO 118
<211> LENGTH: 351
<212> TYPE: DNA
<213> ORGANISM: Homo sapiens

<400> SEQUENCE: 118

```
caggtgcagc tgcaggagtc ggggggaggc gtggtccagc ctgggaggtc cctgaggctc     60
tcctgtgcgg cctctgggtt caccttcagt ggctatggca tgaactgggt ccgccaggct    120
ccaggcacgg ggctggagtg ggtggcaaca atatcatttg atggaactga taaatactat    180
gcagactccg tgaagggccg attcaccatc tccagagaca cgctgagaa cacgctctat     240
ctgcaaatga acagtctgag agccgaggac atggctgtgt attactgtgc aagagattgg    300
tcgtacgcga tggacgtctg gggccaaggg acaatggtca ccgtctcttc a             351
```

<210> SEQ ID NO 119
<211> LENGTH: 324
<212> TYPE: DNA
<213> ORGANISM: Homo sapiens

<400> SEQUENCE: 119

```
tcctatgtgc tgactcagcc accctcagtg tccgtgtccc caggacagac agccagcatc     60
acctgctctg gagataaatt ggaggataaa tacgcttgct ggtatcagca gaagccaggc    120
cagtcccctg tgctggtcat ctatcatgat tacaagcggc cctcagggat ccctgagcga    180
ttctctggct ccaactctgg gaacacagcc accctgacca tcagcagggt cgaaggcggg    240
gatgaggccg actattactg tcaggtgtgg gatagcggta gtgatgatca ggtcttcggc    300
ggagggacca agctgaccgt ccta                                           324
```

<210> SEQ ID NO 120
<211> LENGTH: 366
<212> TYPE: DNA
<213> ORGANISM: Homo sapiens

<400> SEQUENCE: 120

```
caggtgcagc tggtgcagtc tgggtctgac gtgaagaagc cggggggcctc agtgagggtc    60
tcctgcaaag tttccggata cagactcact gagtatccca tacactgggt tcgacaggcg   120
ccggggaaag gacttgagta catgggaggc tttgatcttg aaaatggtgt aacaaaggcc   180
gcaccgaggt tcaggggcag attcaccatg accgaggaca catctacaga ctctgtttat   240
atggagttga gagcctgac atctgaagac acggccgtct attattgtgt aaaggggccg    300
ggatacggtg cgttggtgac ctcctttacc tcctgggcc tggggaccac ggtcaccgtc   360
tcctca                                                              366
```

<210> SEQ ID NO 121

```
<211> LENGTH: 143
<212> TYPE: PRT
<213> ORGANISM: Homo sapiens

<400> SEQUENCE: 121

Thr Lys Ile Val Gly Thr Phe Asn Lys Lys Ser Lys Gly Tyr Thr Asp
1               5                   10                  15

Val Val Arg Ile Pro Glu Gly Ala Thr His Ile Lys Val Arg Gln Phe
            20                  25                  30

Lys Ala Lys Asp Gln Thr Arg Phe Thr Ala Tyr Leu Ala Leu Lys Lys
        35                  40                  45

Lys Asn Gly Glu Tyr Leu Ile Asn Gly Lys Tyr Met Ile Ser Thr Ser
    50                  55                  60

Glu Thr Ile Ile Asp Ile Asn Gly Thr Val Met Asn Tyr Ser Gly Trp
65                  70                  75                  80

Ser His Arg Asp Asp Phe Leu His Gly Met Gly Tyr Ser Ala Thr Lys
                85                  90                  95

Glu Ile Leu Ile Val Gln Ile Leu Ala Thr Asp Pro Thr Lys Pro Leu
            100                 105                 110

Asp Val Arg Tyr Ser Phe Phe Val Pro Lys Lys Ser Thr Pro Lys Val
        115                 120                 125

Asn Ser Val Thr Ser His Gly Ser Asn Lys Val Gly Ser His Thr
    130                 135                 140

<210> SEQ ID NO 122
<211> LENGTH: 17
<212> TYPE: PRT
<213> ORGANISM: Homo sapiens

<400> SEQUENCE: 122

Asn Ala Ala Thr Thr Leu Lys Asn Phe Cys Lys Trp Gln His Gln His
1               5                   10                  15

Asn

<210> SEQ ID NO 123
<211> LENGTH: 429
<212> TYPE: DNA
<213> ORGANISM: Homo sapiens

<400> SEQUENCE: 123
acaaagattg ttggaacctt taataagaaa agtaaggggt acactgacgt ggtgaggatt    60
cctgaagggg caacccacat aaaagttcga cagttcaaag ccaaagacca gactagattc   120
actgcctatt tagccctgaa aaagaaaaac ggtgagtacc ttatcaatgg aaagtacatg   180
atctccactt cagagactat cattgacatc aatggaacag tcatgaacta tagcggttgg   240
agccacaggg atgacttcct gcatggcatg ggctactctg ccacgaagga aattctaata   300
gtgcagattc ttgcaacaga ccccactaaa ccattagatg tccgttatag cttttttgtt   360
cccaagaagt ccactccaaa agtaaactct gtcactagtc atggcagcaa taaagtggga   420
tcacacact                                                          429

<210> SEQ ID NO 124
<211> LENGTH: 51
<212> TYPE: DNA
<213> ORGANISM: Homo sapiens

<400> SEQUENCE: 124
aacgctgcca ccacactcaa gaactttttgc aagtggcagc accaacacaa c            51
```

<210> SEQ ID NO 125
<211> LENGTH: 250
<212> TYPE: PRT
<213> ORGANISM: Homo sapiens

<400> SEQUENCE: 125

Asp Ile Val Ile Thr Gln Asp Glu Leu Ser Asn Pro Val Thr Ser Gly
1               5                   10                  15

Glu Ser Val Ser Ile Ser Cys Arg Ser Lys Ser Leu Leu Tyr Lys
            20                  25                  30

Asp Gly Lys Thr Tyr Leu Tyr Trp Phe Leu Gln Arg Pro Gly Gln Ser
        35                  40                  45

Pro Gln Leu Pro Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
                85                  90                  95

Val Glu Tyr Pro Tyr Thr Phe Gly Gly Gly Thr Lys Leu Glu Ile Lys
            100                 105                 110

Arg Ser Gly Gly Ser Thr Arg Gly Ser Gly Lys Pro Gly Ser Gly Glu
        115                 120                 125

Gly Ser Ser Gly Thr Gln Val Gln Leu Gln Gln Ser Gly Ala Glu Leu
    130                 135                 140

Ala Lys Pro Gly Ala Ser Val Lys Met Ser Cys Lys Ala Ser Gly Tyr
145                 150                 155                 160

Thr Phe Thr Ser Tyr Trp Met His Trp Val Lys Gln Arg Pro Gly Gln
                165                 170                 175

Gly Leu Glu Trp Ile Gly Tyr Ile Asn Pro Ser Thr Gly Tyr Thr Glu
            180                 185                 190

Tyr Asn Gln Lys Phe Lys Asp Lys Ala Thr Leu Thr Ala Asp Lys Ser
        195                 200                 205

Ser Ser Thr Ala Tyr Met Gln Leu Gly Ser Leu Thr Ser Glu Asp Ser
    210                 215                 220

Ala Val Tyr Tyr Cys Ala Arg Gly Gly Tyr Asp Asp Leu Gly Tyr Trp
225                 230                 235                 240

Gly Gln Gly Thr Thr Leu Thr Val Ser Ser
                245                 250

<210> SEQ ID NO 126
<211> LENGTH: 248
<212> TYPE: PRT
<213> ORGANISM: Homo sapiens

<400> SEQUENCE: 126

Asp Ile Val Met Thr Gln Ser Pro Ala Ser Leu Ala Val Ser Gln Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Pro Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

-continued

```
Pro Val Glu Ala Asp Asp Ala Ala Thr Tyr Tyr Cys Gln Gln Asn Asn
                85                  90                  95
Glu Glu Leu Thr Phe Gly Ala Gly Thr Lys Leu Glu Leu Lys Arg Ser
            100                 105                 110
Gly Gly Ser Thr Ser Gly Ser Gly Lys Pro Gly Ser Ser Glu Gly Ser
        115                 120                 125
Ser Gly Thr Glu Val Lys Leu Leu Glu Ser Gly Gly Gly Leu Val Gln
    130                 135                 140
Pro Gly Gly Ser Leu Lys Leu Ser Cys Thr Thr Ser Gly Phe Asp Phe
145                 150                 155                 160
Ser Arg Tyr Trp Met Ser Trp Val Arg Gln Ala Pro Gly Lys Gly Leu
                165                 170                 175
Glu Trp Ile Gly Glu Ile Asn Pro Asp Ser Ser Thr Ile Asn Tyr Thr
            180                 185                 190
Pro Ser Leu Lys Asp Lys Phe Ile Ile Ser Arg Asp Asn Ala Lys Asn
        195                 200                 205
Thr Leu Tyr Leu Gln Met Ser Lys Val Arg Ser Glu Asp Thr Ala Leu
    210                 215                 220
Tyr Tyr Cys Ala Arg Arg Ser Tyr Trp Tyr Phe Asp Val Trp Gly Ala
225                 230                 235                 240
Gly Thr Ser Val Thr Val Ser Ser
                245

<210> SEQ ID NO 127
<211> LENGTH: 244
<212> TYPE: PRT
<213> ORGANISM: Homo sapiens

<400> SEQUENCE: 127

Asp Ile Val Met Thr Gln Ser His Lys Phe Met Ser Thr Ser Glu Gly
1               5                   10                  15
Asp Arg Val Ser Ile Thr Cys Lys Ala Ser Gln Asp Val Gly Thr Ala
            20                  25                  30
Val Ala Trp Tyr Gln Gln Lys Pro Gly Gln Ser Pro Lys Leu Leu Ile
        35                  40                  45
Tyr Trp Ala Ser Thr Arg His Thr Gly Val Pro Asp Arg Phe Thr Gly
    50                  55                  60
Ser Gly Ser Gly Thr Asp Phe Thr Leu Thr Ile Ser Asn Val Gln Ser
65                  70                  75                  80
Glu Asp Leu Ala Asp Tyr Ile Cys Gln Gln Tyr Cys Ser His Pro Tyr
                85                  90                  95
Thr Phe Gly Ala Gly Thr Lys Leu Glu Ile Lys Arg Ser Gly Gly Ser
            100                 105                 110
Thr Ser Gly Ser Gly Lys Pro Gly Ser Gly Glu Gly Ser Arg Gly Thr
        115                 120                 125
Gln Val Gln Leu Gln Gln Ser Gly Ala Glu Pro Val Lys Pro Gly Ala
    130                 135                 140
Ser Val Lys Leu Ser Cys Thr Ala Ser Gly Phe Asn Ile Lys Asp Thr
145                 150                 155                 160
Tyr Met His Trp Val Lys Gln Arg Pro Glu Gln Gly Leu Glu Trp Ile
                165                 170                 175
Gly Arg Ile Asp Pro Ala His Gly Arg Thr Lys Tyr Asp Pro Lys Phe
            180                 185                 190
Gln Gly Lys Ala Thr Ile Thr Ala Asp Thr Ser Ser Asn Thr Ala Tyr
```

```
                195                 200                 205
Leu Gln Leu Ser Ser Leu Ser Ser Glu Asp Thr Ala Val Tyr Tyr Cys
    210                 215                 220

Ala Phe Tyr Ser Tyr Ala Ile Asp Tyr Trp Gly Gln Gly Thr Ser Val
225                 230                 235                 240

Thr Val Ser Ser

<210> SEQ ID NO 128
<211> LENGTH: 254
<212> TYPE: PRT
<213> ORGANISM: Homo sapiens

<400> SEQUENCE: 128

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ala Ile Gly Asn Asp
            20                  25                  30

Leu Ala Trp Tyr Gln Gln Arg Pro Gly Lys Ala Pro Lys Arg Leu Ile
        35                  40                  45

Tyr Gly Ala Ser Thr Leu Ser Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Asn Phe Pro Tyr
                85                  90                  95

Thr Phe Gly Leu Gly Thr Lys Val Glu Ile Lys Ser Gly Gly Ser Thr
            100                 105                 110

Ser Gly Ser Gly Lys Pro Gly Ser Gly Glu Gly Ser Ser Gly Thr Gln
        115                 120                 125

Val Gln Leu Gln Gln Trp Gly Ala Gly Leu Leu Lys Pro Ser Glu Thr
130                 135                 140

Leu Ser Leu Thr Cys Ala Val His Gly Gly Ser Phe Ser Gly Asn Phe
145                 150                 155                 160

Trp Ser Trp Val Arg Gln His Pro Gly Lys Gly Leu Glu Trp Ile Gly
                165                 170                 175

Glu Val Asn His Arg Gly Ser Ala Thr Tyr Asn Pro Ser Leu Lys Ser
            180                 185                 190

Arg Val Thr Met Ser Val Asp Thr Ser Lys Asn Gln Phe Ser Leu Gln
        195                 200                 205

Leu Ser Ser Val Thr Ala Ala Asp Thr Ala Val Tyr Tyr Cys Ala Arg
210                 215                 220

Lys Leu Pro Arg Arg Ala Glu Asp Arg Pro Ser Ser Leu Arg Pro
225                 230                 235                 240

Phe Asp Tyr Trp Gly Gln Gly Thr Leu Val Thr Val Ser Ser
                245                 250

<210> SEQ ID NO 129
<211> LENGTH: 262
<212> TYPE: PRT
<213> ORGANISM: Homo sapiens

<400> SEQUENCE: 129

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30
```

Tyr Asp Val His Trp Tyr Gln Gln Leu Pro Gly Thr Ala Pro Lys Leu
                35                  40                  45

Leu Ile Tyr Gly Asn Asp Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Asn Ser
                85                  90                  95

Leu Ser Gly Tyr Ala Val Phe Gly Gly Gly Thr Gln Leu Thr Val Leu
                100                 105                 110

Ser Gly Gly Ser Thr Ser Gly Ser Gly Lys Pro Gly Ser Gly Glu Gly
                115                 120                 125

Ser Ser Gly Thr Gln Val Gln Leu Val Glu Ser Gly Gly Gly Leu Val
 130                 135                 140

Gln Pro Gly Gly Ser Leu Arg Leu Ser Cys Ala Ala Ser Gly Phe Arg
145                 150                 155                 160

Phe Ser Ser His Asp Met His Trp Val Arg Gln Val Pro Gly Lys Gly
                165                 170                 175

Leu Glu Trp Val Ser Arg Ile Gly Thr Val Gly Asp Thr Tyr Tyr Ala
                180                 185                 190

Asp Ser Val Lys Gly Arg Phe Thr Ile Ser Arg Asp Asn Ser Lys Asn
                195                 200                 205

Thr Leu Phe Leu Gln Met Asn Ser Leu Gly Ala Glu Asp Thr Ala Val
 210                 215                 220

Tyr Tyr Cys Ala Arg Asp Gly Thr Arg Tyr Cys Ser Arg Thr Ser Cys
225                 230                 235                 240

His Ser Gly Tyr Tyr Tyr Gly Met Asp Val Trp Gly Gln Gly Thr
                245                 250                 255

Thr Val Thr Val Ser Ser
                260

<210> SEQ ID NO 130
<211> LENGTH: 248
<212> TYPE: PRT
<213> ORGANISM: Homo sapiens

<400> SEQUENCE: 130

Asp Ile Val Met Thr Gln Thr Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys Ser Gly Gly Ser Thr
                100                 105                 110

Ser Gly Ser Gly Lys Pro Gly Ser Gly Glu Gly Ser Ser Gly Thr Gln
                115                 120                 125

Val Gln Leu Val Gln Ser Gly Gly Gly Leu Val Lys Pro Gly Gly Ser

```
            130                 135                 140
Leu Arg Leu Ser Cys Ala Ala Ser Gly Phe Thr Phe Ser Asp His Tyr
145                 150                 155                 160

Met Asp Trp Val Arg Gln Ala Pro Gly Lys Gly Leu Glu Trp Val Gly
                165                 170                 175

Arg Ile Arg Asn Lys Ala Asn Ser Tyr Thr Thr Glu Tyr Ala Ala Ser
                180                 185                 190

Val Lys Gly Arg Phe Thr Ile Ser Arg Asp Asp Ser Lys Lys Thr Leu
            195                 200                 205

Tyr Leu Gln Met Thr Ser Leu Lys Thr Asp Asp Thr Ala Leu Tyr Tyr
        210                 215                 220

Cys Ala Arg Asp Leu Gly Ala Ser Asp Ala Phe Gly Leu Trp Gly Gln
225                 230                 235                 240

Gly Thr Thr Val Thr Val Ser Ser
                245

<210> SEQ ID NO 131
<211> LENGTH: 259
<212> TYPE: PRT
<213> ORGANISM: Homo sapiens

<400> SEQUENCE: 131

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Leu Ile Tyr Asp Val Ser Asn Arg Pro Ser Gly Val Ser Ser Arg Phe
    50                  55                  60

Ser Gly Ser Lys Ser Gly Asn Ser Ala Ser Leu Thr Ile Ser Gly Leu
65                  70                  75                  80

Gln Ala Glu Asp Glu Ala Asp Tyr Tyr Cys Ser Ser Tyr Thr Arg Arg
                85                  90                  95

Ser Thr Leu Glu Phe Gly Gly Gly Thr Lys Leu Thr Val Leu Ser Gly
            100                 105                 110

Gly Ser Thr Ser Gly Ser Gly Lys Pro Gly Ser Gly Glu Gly Ser Ser
        115                 120                 125

Gly Thr Gln Val Gln Leu Gln Gln Trp Gly Ala Gly Leu Leu Lys Pro
    130                 135                 140

Ser Gly Thr Leu Ser Leu Thr Cys Ala Val Tyr Gly Gly Ser Phe Ser
145                 150                 155                 160

Gly Tyr Tyr Trp Ser Trp Ile Arg Gln Pro Pro Gly Lys Gly Leu Glu
                165                 170                 175

Trp Ile Gly Glu Ile Asn His Ser Gly Ser Thr Asn Tyr Asn Pro Ser
            180                 185                 190

Leu Lys Ser Arg Val Thr Ile Ser Val Asp Thr Ser Lys Asn Gln Phe
        195                 200                 205

Ser Leu Lys Leu Ser Ser Val Thr Ala Ala Asp Thr Ala Val Tyr Tyr
    210                 215                 220

Cys Ala Arg Thr Ile Trp Ser Thr Arg His Asp Phe Trp Ser Gly Tyr
225                 230                 235                 240

Tyr Ser Ser Asn Trp Phe Asp Pro Trp Gly Gln Gly Thr Leu Val Thr
                245                 250                 255
```

Val Ser Ser

<210> SEQ ID NO 132
<211> LENGTH: 249
<212> TYPE: PRT
<213> ORGANISM: Homo sapiens

<400> SEQUENCE: 132

Glu Val Gln Leu Val Glu Ser Gly Ser Asp Val Lys Lys Pro Gly Ala
1               5                   10                  15

Ser Val Arg Val Ser Cys Lys Val Ser Gly Tyr Arg Leu Thr Glu Tyr
            20                  25                  30

Pro Ile His Trp Val Arg Gln Ala Pro Gly Lys Gly Leu Glu Tyr Met
        35                  40                  45

Gly Gly Phe Asp Leu Glu Asn Gly Val Thr Lys Ala Ala Pro Arg Phe
    50                  55                  60

Arg Gly Arg Phe Thr Met Thr Glu Asp Thr Ser Thr Asp Ser Val Tyr
65                  70                  75                  80

Met Glu Leu Lys Ser Leu Thr Ser Glu Asp Thr Ala Val Tyr Tyr Cys
                85                  90                  95

Val Lys Gly Pro Gly Tyr Gly Ala Leu Val Thr Ser Phe Thr Ser Trp
            100                 105                 110

Gly Leu Gly Thr Leu Val Thr Val Ser Ser Ser Gly Gly Ser Thr Ser
        115                 120                 125

Gly Ser Gly Lys Pro Gly Ser Gly Glu Gly Ser Ser Gly Thr Glu Thr
    130                 135                 140

Thr Leu Thr Gln Ser Pro Ala Phe Met Ser Ala Thr Pro Gly Asp Lys
145                 150                 155                 160

Ile Tyr Ile Ser Cys Lys Ala Ser Gln Asp Ile Asp Asp Asp Met Asn
                165                 170                 175

Trp Tyr Gln Gln Lys Pro Gly Glu Ala Ala Ile Phe Ile Ile Gln Glu
            180                 185                 190

Ala Thr Thr Leu Val Pro Gly Ile Pro Pro Arg Phe Ser Gly Ser Gly
        195                 200                 205

Tyr Gly Thr Asp Phe Thr Leu Thr Ile Asn Asn Met Glu Ser Glu Asp
    210                 215                 220

Ala Ala Tyr Tyr Phe Cys Pro Gln Gln Asp Asn Val Pro Leu Thr Phe
225                 230                 235                 240

Gly Gly Gly Thr Lys Val Asp Ile Lys
                245

<210> SEQ ID NO 133
<211> LENGTH: 2793
<212> TYPE: DNA
<213> ORGANISM: Homo sapiens

<400> SEQUENCE: 133
atgctgctcg ggtgggcgtc cctgctgctg tgcgcgttcc gcctgcccct ggccgcggtc      60
ggccccgccg cgacacctgc ccaggataaa gccgggcagc ctccgactgc tgcagcagcc     120
gcccagcccc gccggcggca gggggaggag gtgcaggagc gagccgagcc tcccggccac     180
ccgcaccccc tggcgcagcg gcgcaggagc aaggggctgg tgcagaacat cgaccaactc     240
tactccggcg gcggcaaggt gggctacctc gtctacgcgg cggccggag gttcctcttg      300 gacctggagc gagatggttc ggtgggcatt gctggcttcg tgcccgcagg aggcgggacg     360
agtgcgccct ggcgccaccg gagccactgc ttctatcggg gcacagtgga cgctagtccc     420

-continued

```
cgctctctgg ctgtctttga cctctgtggg ggtctcgacg gcttcttcgc ggtcaagcac    480
gcgcgctaca ccctaaagcc actgctgcgc ggaccctggg cggaggaaga aaaggggcgc    540
gtgtacgggg atgggtccgc acggatcctg cacgtctaca cccgcgaggg cttcagcttc    600
gaggccctgc cgccgcgcgc cagctgcgaa accccgcgt ccacaccgga ggcccacgag     660
catgctccgg cgcacagcaa cccgagcgga cgcgcagcac tggcctcgca gctcttggac    720
cagtccgctc tctcgcccgc tgggggctca ggaccgcaga cgtggtggcg gcggcggcgc    780
cgctccatct cccgggcccg ccaggtggag ctgcttctgg tggctgacgc gtccatggcg    840
cggttgtatg gccggggcct gcagcattac ctgctgaccc tggcctccat cgccaatagg    900
ctgtacagcc atgctagcat cgagaaccac atccgcctgg ccgtggtgaa ggtggtggtg    960
ctaggcgaca aggacaagag cctggaagtg agcaagaacg ctgccaccac actcaagaac   1020 tttttgcaagt ggcagcacca acacaaccag ctgggagatg accatgagga gcactacgat   1080
gcagctatcc tgtttactcg ggaggattta tgtgggcatc attcatgtga caccctggga   1140
atggcagacg ttgggaccat atgttctcca gagcgcagct gtgctgtgat tgaagacgat   1200
ggcctccacg cagccttcac tgtggctcac gaaatcggac atttacttgg cctctcccat   1260
gacgattcca aattctgtga agagaccttt ggttccacag aagataagcg cttaatgtct   1320
tccatcctta ccagcattga tgcatctaag ccctggtcca aatgcacttc agccaccatc   1380
acagaattcc tggatgatgg ccatggtaac tgtttgctgg acctaccacg aaagcagatc   1440
ctgggccccg aagaactccc aggacagacc tacgatgcca cccagcagtg caacctgaca   1500
ttcgggcctg agtactccgt gtgtcccggc atggatgtct gtgctcgcct gtggtgtgct   1560
gtggtacgcc agggccagat ggtctgtctg accaagaagc tgcctgcggt ggaagggacg   1620
ccttgtggaa aggggagaat ctgcctgcag ggcaaatgtg tggacaaaac caagaaaaaa   1680
tattattcaa cgtcaagcca tggcaactgg ggatcttggg gatcctgggg ccagtgttct   1740
cgctcatgtg gaggaggagt gcagtttgcc tatcgtcact gtaataaccc tgctcccaga   1800
aacaacggac gctactgcac agggaagagg gccatctacc gctcctgcag tctcatgccc   1860
tgcccaccca atggtaaatc atttcgtcat gaacagtgtg aggccaaaaa tggctatcag   1920
tctgatgcaa aaggagtcaa aacttttgtg gaatgggttc ccaaatatgc aggtgtcctg   1980
ccagcggatg tgtgcaagct gacctgcaga gccaagggca ctggctacta tgtggtattt   2040
tctccaaagg tgaccgatgg cactgaatgt aggccgtaca gtaattccgt ctgcgtccgg   2100
gggaagtgtg tgagaactgg ctgtgacggc atcattggct caaagctgca gtatgacaag   2160
tgcggagtat gtggaggaga caactccagc tgtacaaaga ttgttggaac ctttaataag   2220
aaaagtaagg gttacactga cgtggtgagg attcctgaag gggcaaccca cataaaagtt   2280
cgacagttca agccaaaga ccagactaga ttcactgcct atttagccct gaaaaagaaa    2340
aacggtgagt acccttatcaa tggaaagtac atgatctcca cttcagagac tatcattgac   2400
atcaatggaa cagtcatgaa ctatagcggt tggagccaca gggatgactt cctgcatggc   2460
atgggctact ctgccacgaa ggaaattcta atagtgcaga ttcttgcaac agacccacac   2520
aaaccattag atgtccgtta tagcttttt gttcccaaga agtccactcc aaaagtaaac   2580
tctgtcacta gtcatggcag caataaagtg ggatcacaca cttcgcagcc gcagtgggtc   2640
acgggcccat ggctcgcctg ctctaggacc tgtgacacag gttggcacac cagaacggtg   2700
cagtgccagg atggaaaccg gaagttagca aaaggatgtc ctctctccca aaggcctct    2760
```

```
gcgtttaagc aatgcttgtt gaagaaatgt tag                         2793
```

<210> SEQ ID NO 134
<211> LENGTH: 2514
<212> TYPE: DNA
<213> ORGANISM: Homo sapiens

<400> SEQUENCE: 134

```
atgtcccaga caggctcgca tcccgggagg ggcttggcag ggcgctggct gtggggagcc   60
caaccctgcc tcctgctccc cattgtgccg ctctcctggc tggtgtggct gcttctgcta  120
ctgctggcct ctctcctgcc ctcagcccgg ctggccagcc cctcccccg ggaggaggag   180
atcgtgtttc agagaagct caacggcagc gtcctgcctg gctcgggcgc ccctgccagg   240
ctgttgtgcc gcttgcaggc cttgggggag acgctgctac tagagctgga gcaggactcc   300
ggtgtgcagg tcgagggggct gacagtgcag tacctgggcc aggcgcctga gctgctgggt   360
ggagcagagc ctggcaccta cctgactggc accatcaatg gagatccgga gtcggtggca   420
tctctgcact gggatggggg agccctgtta ggcgtgttac aatatcgggg ggctgaactc   480
cacctccagc ccctggaggg aggcaccccct aactctgctg ggggacctgg ggctcacatc   540
ctacgccgga gagtcctgc cagcggtcaa ggtcccatgt gcaacgtcaa ggctcctctt   600
ggaagcccca gccccagacc ccgaagagcc aagcgctttg cttcactgag tagatttgtg   660
gagacactgg tggtggcaga tgacaagatg gccgcattcc acggtgcggg gctaaagcgc   720
tacctgctaa cagtgatggc agcagcagcc aaggccttca gcacccaag catccgcaat   780
cctgtcagct tggtggtgac tcggctagtg atcctggggt caggcgagga ggggccccaa   840
gtggggccca gtgctgccca gaccctgcgc agcttctgtg cctggcagcg gggcctcaac   900
accccctgagg actcggaccc tgaccacttt gacacagcca ttctgtttac ccgtcaggac   960
ctgtgtggag tctccacttg cgacacgctg gtatggctg atgtgggcac cgtctgtgac  1020
ccggctcgga gctgtgccat tgtggaggat gatgggctcc agtcagcctt cactgctgct  1080
catgaactgg gtcatgtctt caacatgctc catgacaact ccaagccatg catcagtttg  1140
aatgggcctt tgagcacctc tcgccatgtc atggcccctg tgatggctca tgtggatcct  1200
gaggagccct ggtccccctg cagtgcccgc ttcatcactg acttcctgga caatggctat  1260
gggcactgtc tcttagacaa accagaggct ccattgcatc tgcctgtgac tttccctggc  1320
aaggactatg atgctgaccg ccagtgccag ctgacctcg ggcccgactc acgccattgt  1380
ccacagctgc cgccgcctg tgctgccctc tggtgctctg gccacctcaa tggccatgcc  1440
atgtgccaga ccaaacactc gccctgggcc gatggcacac cctgcgggcc cgcacaggcc  1500
tgcatgggtg gtcgctgcct ccacatggac cagctccagg acttcaatat tccacaggct  1560
ggtggctggg gtccttgggg accatggggt gactgctctc ggacctgtgg gggtggtgtc  1620
cagttctcct cccgagactg cacgaggcct gtccccccgga atggtggcaa gtactgtgag  1680
ggccgccgta cccgcttccg ctcctgcaac actgaggact gcccaactgg ctcagccctg  1740
accttccgcg aggagcagtg tgctgcctac aaccaccgca ccgacctctt caagagcttc  1800
ccagggccca tggactgggt tcctcgctac acaggcgtgg ccccccagga ccagtgcaaa  1860
ctcacctgcc aggcccaggc actgggctac tactatgtgc tggagccacg ggtggtagat  1920
gggacccct gttcccccgga cagctccctg gtctgtgtcc agggccgatg catccatgct  1980
ggctgtgatc gcatcattgg ctccaagaag aagtttgaca gtgcatggt gtgcggaggg  2040
gacggttctg gttgcagcaa gcagtcaggc tccttcagga aattcaggta cggatacaac  2100
```

-continued

```
aatgtggtca ctatcccgc gggggccacc cacattcttg tccggcagca gggaaaccct    2160
ggccaccgga gcatctactt ggccctgaag ctgccagatg gctcctatgc cctcaatggt    2220
gaatacacgc tgatgccctc ccccacagat gtggtactgc ctggggcagt cagcttgcgc    2280
tacagcgggg ccactgcagc ctcagagaca ctgtcaggcc atgggccact ggcccagcct    2340
ttgacactgc aagtcctagt ggctggcaac ccccaggaca cacgcctccg atacagcttc    2400
ttcgtgcccc ggccgacccc ttcaacgcca cgccccactc cccaggactg gctgcaccga    2460
agagcacaga ttctggagat ccttcggcgg cgccctggg cgggcaggaa ataa          2514
```

<210> SEQ ID NO 135
<211> LENGTH: 257
<212> TYPE: PRT
<213> ORGANISM: Homo sapiens

<400> SEQUENCE: 135

Gln Val Gln Leu Gln Glu Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Val Glu Asp Thr Ala Val Tyr Tyr Cys
                85                  90                  95

Ala Arg Asp Arg Asp Leu Leu His Lys Asp Gly Phe Asp Ile Trp Gly
            100                 105                 110

Gln Gly Thr Met Val Thr Val Ser Ser Gly Gly Ser Thr Ser Gly
        115                 120                 125

Ser Gly Lys Pro Gly Ser Gly Glu Gly Ser Ser Gly Thr Gln Ser Val
    130                 135                 140

Leu Thr Gln Pro Pro Ser Ala Ser Ala Ser Leu Gly Ala Ser Val Thr
145                 150                 155                 160

Leu Thr Cys Thr Leu Ser Ser Gly Tyr Ser Asn Tyr Lys Val Asp Trp
                165                 170                 175

Tyr Gln Gln Thr Pro Gly Lys Gly Pro Arg Phe Val Met Arg Val Gly
            180                 185                 190

Thr Gly Gly Thr Val Gly Ser Lys Gly Asp Gly Ile Pro Asp Arg Phe
        195                 200                 205

Ser Val Leu Gly Ser Gly Leu Asn Arg Tyr Leu Ile Ile Lys Asn Ile
    210                 215                 220

Gln Glu Glu Asp Glu Thr Asp Tyr His Cys Gly Ala Asp His Gly Ser
225                 230                 235                 240

Gly Ser Asn Phe Val Tyr Val Phe Gly Ser Gly Thr Lys Val Thr Val
                245                 250                 255

Leu

<210> SEQ ID NO 136
<211> LENGTH: 244
<212> TYPE: PRT
<213> ORGANISM: Homo sapiens

<400> SEQUENCE: 136

```
Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met Asn Trp Val Arg Gln Ala Pro Gly Thr Gly Leu Glu Trp Val
        35                  40                  45

Ala Thr Ile Ser Phe Asp Gly Thr Asp Lys Tyr Tyr Ala Asp Ser Val
50                  55                  60

Lys Gly Arg Phe Thr Ile Ser Arg Asp Asn Ala Glu Asn Thr Leu Tyr
65                  70                  75                  80

Leu Gln Met Asn Ser Leu Arg Ala Glu Asp Met Ala Val Tyr Tyr Cys
                85                  90                  95

Ala Arg Asp Trp Ser Tyr Ala Met Asp Val Trp Gly Gln Gly Thr Met
            100                 105                 110

Val Thr Val Ser Ser Ser Gly Gly Ser Thr Ser Gly Ser Gly Lys Pro
        115                 120                 125

Gly Ser Gly Glu Gly Ser Ser Gly Thr Asp Ile Gln Met Thr Gln Ser
130                 135                 140

Pro Ser Ser Val Ser Ala Ser Val Gly Asp Arg Val Thr Ile Thr Cys
145                 150                 155                 160

Arg Pro Ser Gln Gly Ile Gly Lys Tyr Ser Ala Trp Tyr Gln Gln Lys
                165                 170                 175

Pro Gly Lys Ala Pro Glu Leu Pro Ile Tyr Leu Ala Ser Thr Leu Gln
            180                 185                 190

Ser Gly Val Pro Ser Arg Phe Ser Asp Ser Gly Ser Gly Thr Glu Phe
        195                 200                 205

Thr Leu Thr Ile Ser Ser Leu Gln Pro Glu Asp Phe Ala Thr Tyr Tyr
210                 215                 220

Cys Leu Gln Arg Asn Thr Tyr Pro Trp Thr Phe Gly Gln Gly Thr Lys
225                 230                 235                 240

Val Glu Ile Lys
```

<210> SEQ ID NO 137
<211> LENGTH: 250
<212> TYPE: PRT
<213> ORGANISM: Homo sapiens

<400> SEQUENCE: 137

```
Gln Val Gln Leu Val Gln Ser Gly Ser Asp Val Lys Lys Pro Gly Ala
1               5                   10                  15

Ser Val Arg Val Ser Cys Lys Val Ser Gly Tyr Arg Leu Thr Glu Tyr
            20                  25                  30

Pro Ile His Trp Val Arg Gln Ala Pro Gly Lys Gly Leu Glu Tyr Met
        35                  40                  45

Gly Gly Phe Asp Leu Glu Asn Gly Val Thr Lys Ala Ala Pro Arg Phe
50                  55                  60

Arg Gly Arg Phe Thr Met Thr Glu Asp Thr Thr Asp Ser Val Tyr
65                  70                  75                  80

Met Glu Leu Lys Ser Leu Thr Ser Glu Asp Thr Ala Val Tyr Tyr Cys
                85                  90                  95

Val Lys Gly Pro Gly Tyr Gly Ala Leu Val Thr Ser Phe Thr Ser Trp
            100                 105                 110

Gly Leu Gly Thr Thr Val Thr Val Ser Ser Ser Gly Gly Ser Thr Ser
```

```
            115                 120                 125
Gly Ser Gly Lys Pro Gly Ser Gly Glu Gly Ser Ser Gly Thr Ser Tyr
        130                 135                 140

Val Leu Thr Gln Pro Pro Ser Val Ser Val Ser Pro Gly Gln Thr Ala
145                 150                 155                 160

Ser Ile Thr Cys Ser Gly Asp Lys Leu Glu Asp Lys Tyr Ala Cys Trp
                165                 170                 175

Tyr Gln Gln Lys Pro Gly Gln Ser Pro Val Leu Val Ile Tyr His Asp
            180                 185                 190

Tyr Lys Arg Pro Ser Gly Ile Pro Glu Arg Phe Ser Gly Ser Asn Ser
        195                 200                 205

Gly Asn Thr Ala Thr Leu Thr Ile Ser Arg Val Glu Gly Gly Asp Glu
    210                 215                 220

Ala Asp Tyr Tyr Cys Gln Val Trp Asp Ser Gly Ser Asp Asp Gln Val
225                 230                 235                 240

Phe Gly Gly Gly Thr Lys Leu Thr Val Leu
                245                 250

<210> SEQ ID NO 138
<211> LENGTH: 20
<212> TYPE: PRT
<213> ORGANISM: Artificial Sequence
<220> FEATURE:
<223> OTHER INFORMATION: synthetic linker

<400> SEQUENCE: 138

Ser Gly Gly Ser Thr Ser Gly Ser Gly Lys Pro Gly Ser Gly Glu Gly
1               5                   10                  15

Ser Ser Gly Thr
            20

<210> SEQ ID NO 139
<211> LENGTH: 40
<212> TYPE: DNA
<213> ORGANISM: Artificial Sequence
<220> FEATURE:
<223> OTHER INFORMATION: synthetic primer

<400> SEQUENCE: 139
ttatcctcga gcggtaccca ggtgcagctg caggagtcsg                              40

<210> SEQ ID NO 140
<211> LENGTH: 39
<212> TYPE: DNA
<213> ORGANISM: Artificial Sequence
<220> FEATURE:
<223> OTHER INFORMATION: synthetic primer

<400> SEQUENCE: 140
ttatcctcga gcggtaccca ggtacagctg cagcagtca                               39

<210> SEQ ID NO 141
<211> LENGTH: 40
<212> TYPE: DNA
<213> ORGANISM: Artificial Sequence
<220> FEATURE:
<223> OTHER INFORMATION: synthetic primer

<400> SEQUENCE: 141
ttatcctcga gcggtaccca ggtgcagcta cagcagtggg                              40
```

<210> SEQ ID NO 142
<211> LENGTH: 39
<212> TYPE: DNA
<213> ORGANISM: Artificial Sequence
<220> FEATURE:
<223> OTHER INFORMATION: synthetic primer

<400> SEQUENCE: 142
ttatcctcga gcggtaccga ggtgcagctg ktggagwcy                    39

<210> SEQ ID NO 143
<211> LENGTH: 41
<212> TYPE: DNA
<213> ORGANISM: Artificial Sequence
<220> FEATURE:
<223> OTHER INFORMATION: synthetic primer

<400> SEQUENCE: 143
ttatcctcga gcggtaccca ggtccagctk gtrcagtctg g                 41

<210> SEQ ID NO 144
<211> LENGTH: 40
<212> TYPE: DNA
<213> ORGANISM: Artificial Sequence
<220> FEATURE:
<223> OTHER INFORMATION: synthetic primer

<400> SEQUENCE: 144
ttatcctcga gcggtaccca grtcaccttg aaggagtctg                   40

<210> SEQ ID NO 145
<211> LENGTH: 41
<212> TYPE: DNA
<213> ORGANISM: Artificial Sequence
<220> FEATURE:
<223> OTHER INFORMATION: synthetic primer

<400> SEQUENCE: 145
ttatcctcga gcggtaccca ggtgcagctg gtgsartctg g                 41

<210> SEQ ID NO 146
<211> LENGTH: 40
<212> TYPE: DNA
<213> ORGANISM: Artificial Sequence
<220> FEATURE:
<223> OTHER INFORMATION: synthetic primer

<400> SEQUENCE: 146
gattggtttg ccgctagctg aggagacrgt gaccagggtg                   40

<210> SEQ ID NO 147
<211> LENGTH: 40
<212> TYPE: DNA
<213> ORGANISM: Artificial Sequence
<220> FEATURE:
<223> OTHER INFORMATION: synthetic primer

<400> SEQUENCE: 147
gattggtttg ccgctagctg aggagacggt gaccagggtt                   40

<210> SEQ ID NO 148
<211> LENGTH: 39
<212> TYPE: DNA
<213> ORGANISM: Artificial Sequence
<220> FEATURE:
<223> OTHER INFORMATION: synthetic primer

```
<400> SEQUENCE: 148
gattggtttg ccgctagctg aagagacggt gaccattgt                    39

<210> SEQ ID NO 149
<211> LENGTH: 41
<212> TYPE: DNA
<213> ORGANISM: Artificial Sequence
<220> FEATURE:
<223> OTHER INFORMATION: synthetic primer

<400> SEQUENCE: 149
gattggtttg ccgctagctg aggagacggt gaccgtggtc c                 41

<210> SEQ ID NO 150
<211> LENGTH: 42
<212> TYPE: DNA
<213> ORGANISM: Artificial Sequence
<220> FEATURE:
<223> OTHER INFORMATION: synthetic primer

<400> SEQUENCE: 150
agcaagcggc gcgcatgccg acatccrgdt gacccagtct cc                42

<210> SEQ ID NO 151
<211> LENGTH: 42
<212> TYPE: DNA
<213> ORGANISM: Artificial Sequence
<220> FEATURE:
<223> OTHER INFORMATION: synthetic primer

<400> SEQUENCE: 151
agcaagcggc gcgcatgccg aaattgtrwt gacrcagtct cc                42

<210> SEQ ID NO 152
<211> LENGTH: 42
<212> TYPE: DNA
<213> ORGANISM: Artificial Sequence
<220> FEATURE:
<223> OTHER INFORMATION: synthetic primer

<400> SEQUENCE: 152
agcaagcggc gcgcatgccg atattgtgmt gacbcagwct cc                42

<210> SEQ ID NO 153
<211> LENGTH: 41
<212> TYPE: DNA
<213> ORGANISM: Artificial Sequence
<220> FEATURE:
<223> OTHER INFORMATION: synthetic primer

<400> SEQUENCE: 153
agcaagcggc gcgcatgccg aaacgacact cacgcagtct c                 41

<210> SEQ ID NO 154
<211> LENGTH: 43
<212> TYPE: DNA
<213> ORGANISM: Artificial Sequence
<220> FEATURE:
<223> OTHER INFORMATION: synthetic primer

<400> SEQUENCE: 154
gaagttatgg tcgaccctcc ggatttgatt tccaccttgg tcc               43

<210> SEQ ID NO 155
<211> LENGTH: 43
```

<212> TYPE: DNA
<213> ORGANISM: Artificial Sequence
<220> FEATURE:
<223> OTHER INFORMATION: synthetic primer

<400> SEQUENCE: 155
gaagttatgg tcgaccctcc ggatttgatc tccascttgg tcc        43

<210> SEQ ID NO 156
<211> LENGTH: 43
<212> TYPE: DNA
<213> ORGANISM: Artificial Sequence
<220> FEATURE:
<223> OTHER INFORMATION: synthetic primer

<400> SEQUENCE: 156
gaagttatgg tcgaccctcc ggatttgata tccactttgg tcc        43

<210> SEQ ID NO 157
<211> LENGTH: 43
<212> TYPE: DNA
<213> ORGANISM: Artificial Sequence
<220> FEATURE:
<223> OTHER INFORMATION: synthetic primer

<400> SEQUENCE: 157
gaagttatgg tcgaccctcc ggatttaatc tccagtcgtg tcc        43

<210> SEQ ID NO 158
<211> LENGTH: 42
<212> TYPE: DNA
<213> ORGANISM: Artificial Sequence
<220> FEATURE:
<223> OTHER INFORMATION: synthetic primer

<400> SEQUENCE: 158
agcaagcggc gcgcatgccc agtctgtsbt gacgcagccg cc        42

<210> SEQ ID NO 159
<211> LENGTH: 41
<212> TYPE: DNA
<213> ORGANISM: Artificial Sequence
<220> FEATURE:
<223> OTHER INFORMATION: synthetic primer

<400> SEQUENCE: 159
agcaagcggc gcgcatgcct cctatgwgct gacwcagcca c        41

<210> SEQ ID NO 160
<211> LENGTH: 42
<212> TYPE: DNA
<213> ORGANISM: Artificial Sequence
<220> FEATURE:
<223> OTHER INFORMATION: synthetic primer

<400> SEQUENCE: 160
agcaagcggc gcgcatgcct cctatgagct gayrcagcya cc        42

<210> SEQ ID NO 161
<211> LENGTH: 39
<212> TYPE: DNA
<213> ORGANISM: Artificial Sequence
<220> FEATURE:
<223> OTHER INFORMATION: synthetic primer

<400> SEQUENCE: 161

```
agcaagcggc gcgcatgccc agcctgtgct gactcaryc          39
```

<210> SEQ ID NO 162
<211> LENGTH: 42
<212> TYPE: DNA
<213> ORGANISM: Artificial Sequence
<220> FEATURE:
<223> OTHER INFORMATION: synthetic primer

<400> SEQUENCE: 162

```
agcaagcggc gcgcatgccc agdctgtggt gacycaggag cc       42
```

<210> SEQ ID NO 163
<211> LENGTH: 42
<212> TYPE: DNA
<213> ORGANISM: Artificial Sequence
<220> FEATURE:
<223> OTHER INFORMATION: synthetic primer

<400> SEQUENCE: 163

```
agcaagcggc gcgcatgccc agccwgkgct gactcagccm cc       42
```

<210> SEQ ID NO 164
<211> LENGTH: 42
<212> TYPE: DNA
<213> ORGANISM: Artificial Sequence
<220> FEATURE:
<223> OTHER INFORMATION: synthetic primer

<400> SEQUENCE: 164

```
agcaagcggc gcgcatgcct cctctgagct gastcaggas cc       42
```

<210> SEQ ID NO 165
<211> LENGTH: 40
<212> TYPE: DNA
<213> ORGANISM: Artificial Sequence
<220> FEATURE:
<223> OTHER INFORMATION: synthetic primer

<400> SEQUENCE: 165

```
agcaagcggc gcgcatgccc agtctgyyct gaytcagcct          40
```

<210> SEQ ID NO 166
<211> LENGTH: 41
<212> TYPE: DNA
<213> ORGANISM: Artificial Sequence
<220> FEATURE:
<223> OTHER INFORMATION: synthetic primer

<400> SEQUENCE: 166

```
agcaagcggc gcgcatgcca attttatgct gactcagccc c        41
```

<210> SEQ ID NO 167
<211> LENGTH: 43
<212> TYPE: DNA
<213> ORGANISM: Artificial Sequence
<220> FEATURE:
<223> OTHER INFORMATION: synthetic primer

<400> SEQUENCE: 167

```
gaagttatgg tcgaccctcc ggataggacg gtsascttgg tcc      43
```

<210> SEQ ID NO 168
<211> LENGTH: 43
<212> TYPE: DNA
<213> ORGANISM: Artificial Sequence

```
<220> FEATURE:
<223> OTHER INFORMATION: synthetic primer

<400> SEQUENCE: 168
gaagttatgg tcgaccctcc ggagaggacg gtcagctggg tgc                    43

<210> SEQ ID NO 169
<211> LENGTH: 40
<212> TYPE: DNA
<213> ORGANISM: Artificial Sequence
<220> FEATURE:
<223> OTHER INFORMATION: synthetic primer

<400> SEQUENCE: 169
cgctggattg ttattactcg cagcaagcgg cgcgcatgcc                        40

<210> SEQ ID NO 170
<211> LENGTH: 54
<212> TYPE: DNA
<213> ORGANISM: Artificial Sequence
<220> FEATURE:
<223> OTHER INFORMATION: synthetic primer

<400> SEQUENCE: 170
accgctcgag ccttcaccgg aacctggttt cccagaaccg ctggtcgacc ctcc        54

<210> SEQ ID NO 171
<211> LENGTH: 55
<212> TYPE: DNA
<213> ORGANISM: Artificial Sequence
<220> FEATURE:
<223> OTHER INFORMATION: synthetic primer

<400> SEQUENCE: 171
ggagggtcga ccagcggttc tgggaaacca ggttccggtg aaggctcgag cggta       55

<210> SEQ ID NO 172
<211> LENGTH: 38
<212> TYPE: DNA
<213> ORGANISM: Artificial Sequence
<220> FEATURE:
<223> OTHER INFORMATION: synthetic primer

<400> SEQUENCE: 172
ccaggcccag cagtgggttt gggattggtt tgccgcta                          38

<210> SEQ ID NO 173
<211> LENGTH: 39
<212> TYPE: DNA
<213> ORGANISM: Artificial Sequence
<220> FEATURE:
<223> OTHER INFORMATION: synthetic primer

<400> SEQUENCE: 173
tacctattgc ctacggcagc cgctggattg ttattactc                         39

<210> SEQ ID NO 174
<211> LENGTH: 40
<212> TYPE: DNA
<213> ORGANISM: Artificial Sequence
<220> FEATURE:
<223> OTHER INFORMATION: synthetic primer

<400> SEQUENCE: 174
tggtgatggt gagtactatc caggcccagc agtgggtttg                        40
```

<210> SEQ ID NO 175
<211> LENGTH: 42
<212> TYPE: DNA
<213> ORGANISM: Artificial Sequence
<220> FEATURE:
<223> OTHER INFORMATION: synthetic primer

<400> SEQUENCE: 175
agcaagcggc gcgcatgccc aggtgcagct ggtgcagtct gg        42

<210> SEQ ID NO 176
<211> LENGTH: 42
<212> TYPE: DNA
<213> ORGANISM: Artificial Sequence
<220> FEATURE:
<223> OTHER INFORMATION: synthetic primer

<400> SEQUENCE: 176
agcaagcggc gcgcatgccc aggtcaactt aagggagtct gg        42

<210> SEQ ID NO 177
<211> LENGTH: 42
<212> TYPE: DNA
<213> ORGANISM: Artificial Sequence
<220> FEATURE:
<223> OTHER INFORMATION: synthetic primer

<400> SEQUENCE: 177
agcaagcggc gcgcatgccg aggtgcagct ggtggagtct gg        42

<210> SEQ ID NO 178
<211> LENGTH: 42
<212> TYPE: DNA
<213> ORGANISM: Artificial Sequence
<220> FEATURE:
<223> OTHER INFORMATION: synthetic primer

<400> SEQUENCE: 178
agcaagcggc gcgcatgccc aggtgcagct gcaggagtcg gg        42

<210> SEQ ID NO 179
<211> LENGTH: 42
<212> TYPE: DNA
<213> ORGANISM: Artificial Sequence
<220> FEATURE:
<223> OTHER INFORMATION: synthetic primer

<400> SEQUENCE: 179
agcaagcggc gcgcatgccg aggtgcagct gttgcagtct gc        42

<210> SEQ ID NO 180
<211> LENGTH: 42
<212> TYPE: DNA
<213> ORGANISM: Artificial Sequence
<220> FEATURE:
<223> OTHER INFORMATION: synthetic primer

<400> SEQUENCE: 180
agcaagcggc gcgcatgccc aggtacagct gcagcagtca gg        42

<210> SEQ ID NO 181
<211> LENGTH: 47
<212> TYPE: DNA
<213> ORGANISM: Artificial Sequence
<220> FEATURE:
<223> OTHER INFORMATION: synthetic primer

<400> SEQUENCE: 181
gaagttatgg tcgaccctcc ggatgaggag acggtgacca gggtgcc                          47

<210> SEQ ID NO 182
<211> LENGTH: 47
<212> TYPE: DNA
<213> ORGANISM: Artificial Sequence
<220> FEATURE:
<223> OTHER INFORMATION: synthetic primer

<400> SEQUENCE: 182
gaagttatgg tcgaccctcc ggatgaagag acggtgacca ttgtccc                          47

<210> SEQ ID NO 183
<211> LENGTH: 47
<212> TYPE: DNA
<213> ORGANISM: Artificial Sequence
<220> FEATURE:
<223> OTHER INFORMATION: synthetic primer

<400> SEQUENCE: 183
gaagttatgg tcgaccctcc ggatgaggag acggtgacca gggttcc                          47

<210> SEQ ID NO 184
<211> LENGTH: 47
<212> TYPE: DNA
<213> ORGANISM: Artificial Sequence
<220> FEATURE:
<223> OTHER INFORMATION: synthetic primer

<400> SEQUENCE: 184
gaagttatgg tcgaccctcc ggatgaggag acggtgaccg tggtccc                          47

<210> SEQ ID NO 185
<211> LENGTH: 41
<212> TYPE: DNA
<213> ORGANISM: Artificial Sequence
<220> FEATURE:
<223> OTHER INFORMATION: synthetic primer

<400> SEQUENCE: 185
ttatcctcga gcggtaccga catccagatg acccagtctc c                                41

<210> SEQ ID NO 186
<211> LENGTH: 41
<212> TYPE: DNA
<213> ORGANISM: Artificial Sequence
<220> FEATURE:
<223> OTHER INFORMATION: synthetic primer

<400> SEQUENCE: 186
ttatcctcga gcggtaccga tgttgtgatg actcagtctc c                                41

<210> SEQ ID NO 187
<211> LENGTH: 41
<212> TYPE: DNA
<213> ORGANISM: Artificial Sequence
<220> FEATURE:
<223> OTHER INFORMATION: synthetic primer

<400> SEQUENCE: 187
ttatcctcga gcggtaccga aattgtgttg acgcagtctc c                                41

<210> SEQ ID NO 188

```
<211> LENGTH: 41
<212> TYPE: DNA
<213> ORGANISM: Artificial Sequence
<220> FEATURE:
<223> OTHER INFORMATION: synthetic primer

<400> SEQUENCE: 188
ttatcctcga gcggtaccga catcgtgatg acccagtctc c                          41

<210> SEQ ID NO 189
<211> LENGTH: 41
<212> TYPE: DNA
<213> ORGANISM: Artificial Sequence
<220> FEATURE:
<223> OTHER INFORMATION: synthetic primer

<400> SEQUENCE: 189
ttatcctcga gcggtaccga aacgacactc acgcagtctc c                          41

<210> SEQ ID NO 190
<211> LENGTH: 41
<212> TYPE: DNA
<213> ORGANISM: Artificial Sequence
<220> FEATURE:
<223> OTHER INFORMATION: synthetic primer

<400> SEQUENCE: 190
ttatcctcga gcggtaccga aattgtgctg actcagtctc c                          41

<210> SEQ ID NO 191
<211> LENGTH: 42
<212> TYPE: DNA
<213> ORGANISM: Artificial Sequence
<220> FEATURE:
<223> OTHER INFORMATION: synthetic primer

<400> SEQUENCE: 191
gattggtttg ccgctagcac gtttgatttc caccttggtc cc                         42

<210> SEQ ID NO 192
<211> LENGTH: 42
<212> TYPE: DNA
<213> ORGANISM: Artificial Sequence
<220> FEATURE:
<223> OTHER INFORMATION: synthetic primer

<400> SEQUENCE: 192
gattggtttg ccgctagcac gtttgatctc cagcttggtc cc                         42

<210> SEQ ID NO 193
<211> LENGTH: 42
<212> TYPE: DNA
<213> ORGANISM: Artificial Sequence
<220> FEATURE:
<223> OTHER INFORMATION: synthetic primer

<400> SEQUENCE: 193
gattggtttg ccgctagcac gtttgatatc cactttggtc cc                         42

<210> SEQ ID NO 194
<211> LENGTH: 42
<212> TYPE: DNA
<213> ORGANISM: Artificial Sequence
<220> FEATURE:
<223> OTHER INFORMATION: synthetic primer

<400> SEQUENCE: 194
```
gattggtttg ccgctagcac gtttgatctc caccttggtc cc        42

<210> SEQ ID NO 195
<211> LENGTH: 42
<212> TYPE: DNA
<213> ORGANISM: Artificial Sequence
<220> FEATURE:
<223> OTHER INFORMATION: synthetic primer

<400> SEQUENCE: 195
gattggtttg ccgctagcac gtttaatctc cagtcgtgtc cc        42

<210> SEQ ID NO 196
<211> LENGTH: 41
<212> TYPE: DNA
<213> ORGANISM: Artificial Sequence
<220> FEATURE:
<223> OTHER INFORMATION: synthetic primer

<400> SEQUENCE: 196
ttatcctcga gcggtaccca gtctgtgttg acgcagccgc c         41

<210> SEQ ID NO 197
<211> LENGTH: 41
<212> TYPE: DNA
<213> ORGANISM: Artificial Sequence
<220> FEATURE:
<223> OTHER INFORMATION: synthetic primer

<400> SEQUENCE: 197
ttatcctcga gcggtaccca gtctgccctg actcagcctg c         41

<210> SEQ ID NO 198
<211> LENGTH: 41
<212> TYPE: DNA
<213> ORGANISM: Artificial Sequence
<220> FEATURE:
<223> OTHER INFORMATION: synthetic primer

<400> SEQUENCE: 198
ttatcctcga gcggtacctc ctatgtgctg actcagccac c         41

<210> SEQ ID NO 199
<211> LENGTH: 41
<212> TYPE: DNA
<213> ORGANISM: Artificial Sequence
<220> FEATURE:
<223> OTHER INFORMATION: synthetic primer

<400> SEQUENCE: 199
ttatcctcga gcggtacctc ttctgagctg actcaggacc c         41

<210> SEQ ID NO 200
<211> LENGTH: 41
<212> TYPE: DNA
<213> ORGANISM: Artificial Sequence
<220> FEATURE:
<223> OTHER INFORMATION: synthetic primer

<400> SEQUENCE: 200
ttatcctcga gcggtaccca cgttatactg actcaaccgc c         41

<210> SEQ ID NO 201
<211> LENGTH: 41
<212> TYPE: DNA

<213> ORGANISM: Artificial Sequence
<220> FEATURE:
<223> OTHER INFORMATION: synthetic primer

<400> SEQUENCE: 201
ttatcctcga gcggtaccca ggctgtgctc actcagccgt c                41

<210> SEQ ID NO 202
<211> LENGTH: 42
<212> TYPE: DNA
<213> ORGANISM: Artificial Sequence
<220> FEATURE:
<223> OTHER INFORMATION: synthetic primer

<400> SEQUENCE: 202
gattggtttg ccgctagcac ctaggacggt gaccttggtc cc                42

<210> SEQ ID NO 203
<211> LENGTH: 42
<212> TYPE: DNA
<213> ORGANISM: Artificial Sequence
<220> FEATURE:
<223> OTHER INFORMATION: synthetic primer

<400> SEQUENCE: 203
gattggtttg ccgctagcac ctaggacggt cagcttggtc cc                42

<210> SEQ ID NO 204
<211> LENGTH: 42
<212> TYPE: DNA
<213> ORGANISM: Artificial Sequence
<220> FEATURE:
<223> OTHER INFORMATION: synthetic primer

<400> SEQUENCE: 204
gattggtttg ccgctagcac ctaaaacggt gagctggtc cc                42

<210> SEQ ID NO 205
<211> LENGTH: 40
<212> TYPE: DNA
<213> ORGANISM: Artificial Sequence
<220> FEATURE:
<223> OTHER INFORMATION: synthetic primer

<400> SEQUENCE: 205
cgctggattg ttattactcg cagcaagcgg cgcgcatgcc                   40

<210> SEQ ID NO 206
<211> LENGTH: 54
<212> TYPE: DNA
<213> ORGANISM: Artificial Sequence
<220> FEATURE:
<223> OTHER INFORMATION: synthetic primer

<400> SEQUENCE: 206
accgctcgag ccttcaccgg aacctggttt cccagaaccg ctggtcgacc ctcc   54

<210> SEQ ID NO 207
<211> LENGTH: 55
<212> TYPE: DNA
<213> ORGANISM: Artificial Sequence
<220> FEATURE:
<223> OTHER INFORMATION: synthetic primer

<400> SEQUENCE: 207
ggagggtcga ccagcggttc tgggaaacca ggttccggtg aaggctcgag cggta  55

<210> SEQ ID NO 208
<211> LENGTH: 38
<212> TYPE: DNA
<213> ORGANISM: Artificial Sequence
<220> FEATURE:
<223> OTHER INFORMATION: synthetic primer

<400> SEQUENCE: 208
ccaggcccag cagtgggttt gggattggtt tgccgcta                    38

<210> SEQ ID NO 209
<211> LENGTH: 39
<212> TYPE: DNA
<213> ORGANISM: Artificial Sequence
<220> FEATURE:
<223> OTHER INFORMATION: synthetic primer

<400> SEQUENCE: 209
tacctattgc ctacggcagc cgctggattg ttattactc                   39

<210> SEQ ID NO 210
<211> LENGTH: 40
<212> TYPE: DNA
<213> ORGANISM: Artificial Sequence
<220> FEATURE:
<223> OTHER INFORMATION: synthetic primer

<400> SEQUENCE: 210
tggtgatggt gagtactatc caggcccagc agtgggtttg                  40

<210> SEQ ID NO 211
<211> LENGTH: 27
<212> TYPE: DNA
<213> ORGANISM: Artificial Sequence
<220> FEATURE:
<223> OTHER INFORMATION: synthetic primer

<400> SEQUENCE: 211
tggctggaat tcacaaagat tgttgga                                27

<210> SEQ ID NO 212
<211> LENGTH: 30
<212> TYPE: DNA
<213> ORGANISM: Artificial Sequence
<220> FEATURE:
<223> OTHER INFORMATION: synthetic primer

<400> SEQUENCE: 212
gtcgacggat ccttaagtgt gtgatcccac                             30

<210> SEQ ID NO 213
<211> LENGTH: 64
<212> TYPE: DNA
<213> ORGANISM: Artificial Sequence
<220> FEATURE:
<223> OTHER INFORMATION: synthetic primer

<400> SEQUENCE: 213
aattcaacgc tgccaccaca ctcaagaact tttgcaagtg gcagcaccaa cacaactaac    60
tgca                                                         64

<210> SEQ ID NO 214
<211> LENGTH: 56
<212> TYPE: DNA

```
<213> ORGANISM: Artificial Sequence
<220> FEATURE:
<223> OTHER INFORMATION: synthetic sequence

<400> SEQUENCE: 214
gttagttgtg ttggtgctgc cacttgcaaa agttcttgag tgtggtggca gcgttg        56

<210> SEQ ID NO 215
<211> LENGTH: 28
<212> TYPE: DNA
<213> ORGANISM: Artificial Sequence
<220> FEATURE:
<223> OTHER INFORMATION: synthetic sequence

<400> SEQUENCE: 215
atccatggtc acaaagattg ttggaacc                                        28

<210> SEQ ID NO 216
<211> LENGTH: 33
<212> TYPE: DNA
<213> ORGANISM: Artificial Sequence
<220> FEATURE:
<223> OTHER INFORMATION: synthetic primer

<400> SEQUENCE: 216
atctcgagtt aagtgtgtga tcccacttta ttg                                  33
```